US008980561B1

(12) United States Patent
Cai et al.

(10) Patent No.: US 8,980,561 B1
(45) Date of Patent: Mar. 17, 2015

(54) NUCLEIC ACID DETECTION SYSTEM AND METHOD FOR DETECTING INFLUENZA

(75) Inventors: Hong Cai, Los Alamos, NM (US); Jian Song, Los Alamos, NM (US)

(73) Assignee: Los Alamos National Security, LLC., Los Alamos, NM (US)

( * ) Notice: Subject to any disclaimer, the term of this patent is extended or adjusted under 35 U.S.C. 154(b) by 498 days.

(21) Appl. No.: 11/894,908

(22) Filed: Aug. 22, 2007

Related U.S. Application Data

(60) Provisional application No. 60/839,537, filed on Aug. 22, 2006.

(51) Int. Cl.
*C12Q 1/68* (2006.01)
*C12P 19/34* (2006.01)

(52) U.S. Cl.
USPC .............................. 435/6.12; 435/6.1; 435/6.11

(58) Field of Classification Search
None
See application file for complete search history.

(56) References Cited

U.S. PATENT DOCUMENTS

| | | | |
|---|---|---|---|
| 3,667,607 A | 6/1972 | Brandt | |
| 4,235,601 A | 11/1980 | Deutsch et al. | |
| 4,683,195 A | 7/1987 | Mullis et al. | |
| 4,683,202 A | 7/1987 | Mullis | |
| 4,800,159 A | 1/1989 | Mullis et al. | |
| 4,960,691 A | 10/1990 | Gordon et al. | |
| 5,225,163 A | 7/1993 | Andrews | |
| 5,354,538 A | 10/1994 | Bunce et al. | |
| 5,578,467 A * | 11/1996 | Schuster et al. | 435/91.2 |
| 5,618,494 A | 4/1997 | Bunce et al. | |
| 5,716,819 A | 2/1998 | Chatterjee | |
| 5,736,188 A | 4/1998 | Alcock et al. | |
| 5,741,647 A | 4/1998 | Tam | |
| 5,922,617 A | 7/1999 | Wang et al. | |
| 6,007,999 A | 12/1999 | Clark | |
| 6,037,127 A * | 3/2000 | Ebersole et al. | 435/6.19 |
| 6,146,589 A | 11/2000 | Chandler | |
| 6,214,587 B1 | 4/2001 | Dattagupta et al. | |
| 6,261,779 B1 | 7/2001 | Barbera-Guillem et al. | |
| 6,300,069 B1 | 10/2001 | Missel et al. | |
| 6,468,749 B1 * | 10/2002 | Ulanovsky et al. | 435/6 |
| 6,471,916 B1 | 10/2002 | Noblett | |
| 6,555,349 B1 | 4/2003 | O'Donnell | |
| 6,743,399 B1 | 6/2004 | Weigl et al. | |
| 7,094,536 B2 | 8/2006 | Kurn | |
| 7,159,618 B2 | 1/2007 | Broyer et al. | |
| 7,186,508 B2 | 3/2007 | Lee et al. | |
| 7,195,872 B2 | 3/2007 | Agrawal et al. | |
| 7,273,590 B2 | 9/2007 | Yao et al. | |
| 8,173,078 B2 | 5/2012 | Yao et al. | |
| 2001/0019825 A1 | 9/2001 | Lee et al. | |
| 2002/0076825 A1 | 6/2002 | Cheng et al. | |
| 2002/0179445 A1 | 12/2002 | Alajoki et al. | |
| 2003/0008308 A1 | 1/2003 | Enzelberger et al. | |
| 2003/0064364 A1 | 4/2003 | Lockhart et al. | |
| 2003/0170686 A1 * | 9/2003 | Hoet et al. | 435/6 |
| 2003/0190608 A1 | 10/2003 | Blackburn | |
| 2004/0058378 A1 | 3/2004 | Kong et al. | |
| 2004/0110167 A1 * | 6/2004 | Gerdes et al. | 435/6 |
| 2005/0014192 A1 | 1/2005 | Kurn | |
| 2005/0032730 A1 * | 2/2005 | Von Der Mulbe et al. | 514/44 |
| 2005/0079492 A1 | 4/2005 | Burgess, Jr. et al. | |
| 2005/0136443 A1 | 6/2005 | Shigemori | |
| 2005/0227275 A1 | 10/2005 | Jung et al. | |
| 2005/0243321 A1 | 11/2005 | Cohen et al. | |
| 2005/0250141 A1 | 11/2005 | Lambert et al. | |
| 2006/0024813 A1 | 2/2006 | Warthoe | |
| 2006/0041058 A1 | 2/2006 | Yin et al. | |
| 2006/0127886 A1 | 6/2006 | Kaylor et al. | |
| 2006/0154286 A1 | 7/2006 | Kong et al. | |
| 2006/0160078 A1 | 7/2006 | Cardy et al. | |
| 2006/0239859 A1 | 10/2006 | Ohman et al. | |
| 2006/0286570 A1 | 12/2006 | Rowlen et al. | |
| 2007/0015166 A1 | 1/2007 | Nilsen | |
| 2007/0020768 A1 | 1/2007 | Rundstrom et al. | |
| 2007/0039835 A1 | 2/2007 | Rossier et al. | |
| 2008/0145835 A1 | 6/2008 | Alajem et al. | |
| 2008/0207892 A1 | 8/2008 | Iwaki | |
| 2008/0280285 A1 | 11/2008 | Chen et al. | |
| 2009/0053106 A1 | 2/2009 | Wu et al. | |
| 2009/0130719 A1 | 5/2009 | Handique | |

(Continued)

FOREIGN PATENT DOCUMENTS

| | | |
|---|---|---|
| CN | 1254844 A | 5/2000 |
| CN | 1654214 A | 4/2007 |

(Continued)

OTHER PUBLICATIONS

Buck et al., Design Strategies and Performance of Custom DNA Sequencing Primers, BioTechniques 27:528-536 (Sep. 1999).*
Sunen et al., Recovery and detection of enterovirus, hepatitis A virus and Norwalk virus in hardshell clams (*Mercenaria mercenaria*) by RT-PCR methods, Journal of Virological Methods 77 (1999) 179-187.*
Schwab et al., "Immunoaffinity concentration and purification of waterborne enteric viruses for detection by reverse transcriptase PCR," Appl. Environ. Microbiol., 1996, vol. 62, No. 6, pp. 2086-2094.*
Mumford et al., "Rapid single-tube immunocapture RT-PCR for the detection of two yam potyviruses," Journal of Virological Methods, 1997, vol. 69, pp. 73-79.*
"Microarray technology: An array of opportunities", Nature, vol. 416, Macmillan Magazines, Ltd., Apr. 25, 2002, 885-891.
Akane, Atsushi et al., "Identification of the Heme Compound Copurified with Deoxyribonucleic Acid (DNA) from Bloodstains, a Major Inhibitor of Polymerase Chain Reaction (PCR) Amplification1'", Journal of Forensic Sciences, vol. 39, No. 2, ASTM Internationa, Mar. 1994, 362-372.

(Continued)

*Primary Examiner* — Young J Kim
(74) *Attorney, Agent, or Firm* — Philip D. Askenazy; Peacock Myers, P.C.

(57) ABSTRACT

The invention provides a rapid, sensitive and specific nucleic acid detection system which utilizes isothermal nucleic acid amplification in combination with a lateral flow chromatographic device, or DNA dipstick, for DNA-hybridization detection. The system of the invention requires no complex instrumentation or electronic hardware, and provides a low cost nucleic acid detection system suitable for highly sensitive pathogen detection. Hybridization to single-stranded DNA amplification products using the system of the invention provides a sensitive and specific means by which assays can be multiplexed for the detection of multiple target sequences.

12 Claims, 20 Drawing Sheets

(56) References Cited

U.S. PATENT DOCUMENTS

| | | | |
|---|---|---|---|
| 2010/0203532 A1 | 8/2010 | Makrigiorgos |
| 2010/0248273 A1 | 9/2010 | Campbell et al. |
| 2010/0276005 A1 | 11/2010 | Allain et al. |
| 2011/0039261 A1 | 2/2011 | Hillebrand et al. |

FOREIGN PATENT DOCUMENTS

| | | |
|---|---|---|
| CN | 10140993 | 4/2009 |
| EP | 1972938 A1 | 9/2008 |
| GB | 2 261 284 A | 5/1993 |
| JP | 2006-520190 | 9/2006 |
| JP | 2007-503968 | 3/2007 |
| WO | 97/03207 | 1/1997 |
| WO | 00/29112 | 5/2000 |
| WO | 2004/009055 A1 | 10/2004 |
| WO | 2004/092342 A2 | 10/2004 |
| WO | 2006/122311 A2 | 11/2006 |
| WO | 2007083388 | 7/2007 |
| WO | 2009/103843 A2 | 8/2009 |
| WO | 2009/137509 A1 | 11/2009 |
| WO | 2010105074 A1 | 9/2010 |

OTHER PUBLICATIONS

Albretsen, Catrine et al., "Optimal Conditions for Hybridization with Oligonucleotides: A Study with myc-Oncogene DNA Probes", Analytical Biochemistry, vol. 170, Academic Press, Inc., 1988, 193-202.
An, Lixin et al., "Characterization of a Thermostable UvrD Helicase and Its Participation in Helicase-dependent Amplification", The Journal of Biological Chemistry, vol. 280, No. 32, American Society for Biochemistry and Molecular Biology, Inc., Aug. 12, 2005, 28952-28958.
Andreotti, Peter E. et al., "Immunoassay of infectious agents", BioTechniques Euro Edition, vol. 35, No. 4, Oct. 2003, 850-859.
Ausbel, et al., "Current Protocols in Molecular Biology", John Wiley & Sons, Inc., 1992, 15.6.1-15.6.4.
Baeumner, Antje J. et al., "A rapid biosensor for viable B. anthracis spores", Anal. Bioanal. Chem., vol. 380, 2004, 15-23.
Baeumner, Antje J. et al., "A Universal Nucleic Acid Sequence Biosensor with Nanomolar Detection Limits", Analytical Chemistry, vol. 76, No. 4, American Chemical Society, Feb. 15, 2004, 888-894.
Baeumner, Antje J. et al., "Biosensor for Dengue Virus Detection: Sensitive, Rapid, and Serotype Specific", Analytical Chemistry, vol. 74, No. 6, American Chemical Society, Mar. 15, 2002, 1442-1448.
Baeumner, Antje J., "Biosensors for environmental pollutants and food contaminants", Anal Bioanal Chem, vol. 377, 2003, 434-445.
Barany, Francis, "The Ligase Chain Reaction in a PCR World", Genome Research, vol. 1, Cold Spring Harbor Laboratory Press, Aug. 1991, 5-16.
Berthelet, Marc et al., "Rapid, direct extraction of DNA from soild for PCR analysis using polyvinylpyrrolidone spin columns", FEMS Microbiology Letter, vol. 138, Federation of European Microbiological Societies, 1996, 17-22.
Biagini, Raymond E. et al., "Rapid, Sensitive, and Specific Lateral-Flow Immunochromatographic Device to Measure Anti-Anthrax Protective Antigen Immunoglobulin G in Serum and Whole Blood", Clinical and Vaccine Immunology, vol. 13, No. 5, May 2006, 541-546.
Blake, R. D. et al., "Thermodynamic effects of formamide on DNa stability", Nucleic Acids Research, vol. 24, No. 11, Oxford University Press, 1996, 2095-2103.
Boom, R. et al., "Rapid and Simple Method for Purification of Nucleic Acids", Journal of Clinical Microbiology, vol. 28, No. 3, American Society for Microbiology, Mar. 1990, 495-503.
Boom, R. et al., "Rapid Purification of Hepatitis B Virus DNA from Serum", Journal of Clinical Microbiology, vol. 29, No. 9, American Society for Microbiology, Sep. 1991, 1804-1811.
Braasch, Dwaine A. et al., "Locked nucleic acid (LNA): fine-tuning the recognition of DNa and RNA", Chemistry & Biology, vol. 8, Elsevier Science Ltd., 2001, 731-735.
Bright, Rick A. et al., "Incidence of adamantane resistance among influenza A (H3N2) viruses isolated worldwide from 1994 to 2005: a cause for concern", Lancet, vol. 366, Sep. 22, 2005, 1175-1181.
Brlansky, R. H. et al., "Colonization of the Sharpshooter Vectors, *Oncometopia nigricans* and *Homalodisca coagulata*, by Xylem-LOimited Bacteria", Phytopathology, vol. 73, No. 4, The American Phytopathological Society, 1983, 530.535.
Brlansky, R. H. et al., "Transmission of the Citrus Variegated Chlorosis Bacterium *Xylella fastidiosa* with the Sharpshooter *Oncometopia nigricans*", Plant Disease, vol. 86, No. 11, American Phytopathological Society, Nov. 2002, 1237-1239.
Buhro, William E. et al., "Semiconductor nanocrystals: Shapematters", Nature Materials, vol. 2, No. 3, Nature Publishing Group, Mar. 2003, 138-139.
Capaldi, Stephen et al., "Signal amplification through nucleotide extension and excision on a dendritic DNA platform", Nucleic Acids Research, vol. 28, No. 7, Oxford University Press, 2000, i-vii.
Carter, Darren J. et al., "Lateral flow microarrays: a novel platform for rapid nucleic acid detection based on miniaturized lateral flow chromatography", Nucleic Acids Research, vol. 35, No. 10, 2007, 1-11.
Caruthers, Jonathan M. et al., "Helicase structure and mechanism", Curr Opin Struc Biol, vol. 12, 2002, 123-133.
Chang, Chung J. et al., "Culture and Serological Detection of the Xylem-Limited Bacterium Causing Citrus Variegated Chlorosis and Its Identification as a Strain of *Xylella fastidiosa*", Current Microbiology, vol. 27, Springer-Verlag New York, Inc., 1993, 137-142.
Chanteau, Suzanne et al., "Early diagnosis of bubonic plague using F1 antigen capture ELISA assay and rapid immunogold dipstick", Int. J. Med. Microbiol., vol. 290, No. 3, Urban & Fischer Verlag, 2000, 279-283.
Chanteau, Suzanne et al., "Early diagnosis of bubonic plague using F1 antigen capture ELISA assay and rapid immunogold dipstick", Int. J. Med. Microbiol., vol. 290, No. 3, Urgan & Fischer Verlag, 2000, 279-283.
Cheek, Brady J. et al., "Chemiluminescence Detection for Hybridization Assays on the Flow-Thru Chip, a Three-Dimensional Microchannel Biochip", Analytical Chemistry, vol. 73, No. 24, American Chemical Society, Dec. 15, 2001, 5777-5783.
Chin, Curtis D. et al., "Lab-on-a-chip devices for global health: Past Studies and future opportunities", Lab Chip, vol. 7, The Royal Society of Chemistry, 2007, 41-57.
Ciapina, L. P. et al., "A nested-PCR assay for detection of *Xylella fastidiosa* in citrus plants and sharpshooter leafhoppers", Journal of Applied Microbiology, vol. 96, Society for Applied Microbiology, 2004, 546-551.
Cirino, Nick M. et al., "Multiplex diagnostic platforms for detection of biothreat agents", Expert Rev. Mol. Diagn., vol. 4, No. 6, Future Drugs, Ltd., 2004, 841-857.
Collins, Ruairi, "Purification and characterization of *Thermus thermophilus* UvrD", Extremophiles, vol. 7, 2003, 35-41.
Compton, J., "Nucleic acid sequence-based amplification", Nature, vol. 350, Nature Publishing Group, Mar. 7, 1991, 91-92.
Cook, Alan F. et al., "Synthesis and hybridization of a series of biotinylated oligonucleotides", Nucleic Acids Research, vol. 16, No. 9, IRL Press Limited, Oxford, England, 1988, 4077-4095.
Cubero, J. et al., "Genetic Relationship among Worldwide Strains of *Xanthomonas* Causing Canker in *Citrus* Species and Design of New Primers for Their Identification by PCR", Applied and Environmental Microbiology, vol. 68, No. 3, American Society for Microbiology, Mar. 2002, 1257-1264.
Cubero, J. et al., "Quantitative PCR Method for Diagnosis of *Citrus* Bacterial Canker", Applied and Environmental Microbiology, vol. 67, No. 6, American Society for Microbiology, Jun. 2001, 2849-2852.
Davis, Michael J. et al., "Pierce's Disease of Grapevines: Isolation of the Causal Bacterium", Science, vol. 199, Jan. 6, 1978, 775-778.
Dawson, Erica D. et al., "Identification of A/H5N1 Influenza Viruses Using a Single Gene Diagnostic Microarray", Anal. Chem., vol. 79, American Chemical Society, 2007, 378-384.
Day, Philip J. et al., "Immobilization of polynucleotides on magnetic particles", Biochem. J., vol. 278, 1991, 735-740.

(56) References Cited

OTHER PUBLICATIONS

De Jong, Menno D. et al., "Oseltamivir Resistance during Treatment of Influenza A (H5N1) Infection", New England Journal of Medicine, vol. 353, No. 25, Massachusetts Medical Society, Dec. 22, 2005, 2667-2672.
Deiman, Birgit et al., "Characteristics and Applications of Nucleic Acid Sequence-Based Amplification (NASBA)", Molecular Biotechnology, vol. 20, Humana Press, Inc., 2002, 163-179.
Dineva, Magda A. et al., "Simultaneous Visual Detection of Multiple Viral Amplicons by Dipstick Assay", Journal of Clinical Microbiology, vol. 43, No. 8, American Society for Microbiology, Aug. 2005, 4015-4021.
Dobkin, Carl et al., "RNA Replication: Required Itermediates and the Dissociation of Template, Product, and QB Replicase", Biochemistry, vol. 18, American Chemical Society, 1979, 2038-2044.
Dong, Feng et al., "A coupled complex of T4 DNA replication helicase (gp41) and polymerase (gp43) can perform rapid and processive DNA strand-displacement synthesis", Proc. Natl. Acad. Sci. USA, vol. 93, Dec. 1996, 14456-14461.
Duck, P. et al., "Probe Amplifier System Based on Chimeric Cycling Oligonucleotides", Biotechniques, vol. 9, No. 2, 1990, 142-148.
Easterday, W. R. et al., "Use of Single Nucleotide Polymorphisms in the plxR Gene for Specific Identification of *Bacillus anthracis*", Journal of Clinical Microbiology, vol. 43, No. 4, American Society for Microbiology, Apr. 2005, 1995-1997.
Easterday, William R. et al., "Specific detection of *Bacillus anthracis* using a TaqMan mismatch amplification mutation assay", BioTechniques, vol. 38, No. 5, 2005, 731-735.
Edwards, Katie A. et al., "Optimization of DNA-tagged dye-encapsulating liposomes for lateral-flow assays based on sandwich hybridization", Anal. Bioanal. Chem., vol. 386, 2006, 1335-1343.
Elliott, K. et al., "Use of laser microdissection greatly improves the recovery of DNA from sperm on microscope slides", Forensic Science International, vol. 137, No. 1, Elsevier Ireland Ltd., 2003, 28-36.
Fong, Whalley K. et al., "Rapid Solid-Phase Immunoassay for Detection of Methicillin-Resistant *Staphylococcus aureus* Using Cycling Probe Technology", Journal of Clinical Microbiology, vol. 38, No. 7, American Society for Microbiology, Jul. 2000, 2525-2529.
Fukuta, Shiro et al., "Development of immunocapture reverse transcription loop-mediated isothermal amplification for the detection of tomato spotted wilt virus from chrysanthemum", Journal of Virological Methods, vol. 121, No. 1, Elsevier B.V., 2004, 49-55.
Gani, Raymond et al., "Potential Impact of Antiviral Drug Use during Influenza Pandemic", Emerging Infectious Diseases, vol. 11, No. 9,, Sep. 2005, 1355-1362.
Gill, Peter et al., "An investigation of the rigor of interpretation rules for STRs derived from less than 100 pg of DNA", Forensic Science International, vol. 112, Elsevier Science Ireland Ltd., 2000, 17-40.
Gill, Peter , "Application of Low Copy Number DNA Profiling", Croatian Medical Journal, vol. 42, No. 3, 2001, 228-232.
Glynou, Kyriaki et al., "Oligonucleotide-Functionalized Gold Nanopartices as Probes in a Dry-Reagent Strip Biosensor for DNA Analysis by Hybridization", Analytical Chemistry, vol. 75, No. 16, American Chemical Society, Aug. 15, 2003, 4155-4160.
Goheen, A. C. et al., "Association of a Rickettsialike Organism with Pierce's Disease of Grapevines and Alfalfa Swarf and Heat Therapy of the Disease in Grapevines", Phytopathology, vol. 63, Mar. 1973, 341-345.
Grainge, Ian et al., "Biochemical analysis of components of the pre-replication complex of *Archaeoglobus fulgidus*", Nucleic Acids Research, vol. 31, No. 16, Oxford University Press, 2003, 4888-4898.
Groody, E. P. , "Detection of Foodborne Pathogens Using DNA Probes and a Dipstick Format", Molecular Biotechnology, vol. 6, Humana Press, Inc., 1996, 323-327.
Guatelli, John C. et al., "Isothermal, in vitro amplification of nucleic acids by a multienzyme reaction modeled after retroviral replication", Proc. Natl. Acad. Sci. USA, vol. 87, Mar. 1990, 1874-1878.
Guo, Zhen et al., "Direct fluorescence analysis of genetic polymorphisms by hybridization with oligonucleotide arrays on glass supports", Nucleic Acids Research, vol. 22, No. 24, Oxford University Press, 1994, 5456-5465.
Harmon, Frank G. et al., "Biochemical Characterization of the DNA Helicase Activity of the *Escherichia coli* RecQ Helicase", The Journal of Biological Chemistry, vol. 276, No. 1, American Society for Biochemistry and Molecular Biology, Inc., 2001, 232-243.
Hartley, Harriet A. et al., "Biosensor for the specific detection of a single viable *B. anthracis* spore", Anal. Bioanal. Chem., vol. 376, 2003, 319-327.
Hartung, J. S. et al., "Detection of *Xanthomonas campestris* pv. Citri by the Polymerase Chain Reaction Method", Applied and Environmental Microbiology, vol. 59, No. 4, American Society for Microbiology, Apr. 1993, 1143-1148.
Hartung, John S. et al., "Rapid and Sensitive Colorimetric Detection of *Xanthomonas axonopodis* pv. citri by Immunocapture and a Nested-Polymerase Chain Reaction Assay", Phytopathology, vol. 86, No. 1, American Phytopathological Society, 1996, 95-101.
Heller, M. J. , "DNA microarray technology: devices, systems, and applications", Annu. Rev. Biomed. Eng., vol. 4, 2002, 129-153.
Hendson, Mavis et al., "Genetic Diversity of Pierce's Disease Strains and Other Pathotypes of *Xylella fastidiosa*", Applied and Environmental Microbiology, vol. 67, No. 2, American Society for Microbiology, Feb. 2001, 895-903.
Hill, B. L. et al., "Acquisition and Retention of *Xylella fastidiosa* by an Efficient Vector, *Graphocephala atropunctata*", Phytopathology, vol. 85, No. 2, American Phytopathological Society, 1997, 209-212.
Hill, B. L. et al., "Populations of *Xylella fastidiosa* in Plants Required for Transmission by an Efficient Vector", Phytopathology, vol. 87, No. 12, American Phytopathological Society, 1997, 1197-1201.
Hill, Karen K. et al., "Fluorescent Amplified Fragment Length Polymorphism Analysis of *Bacillus anthracis*, *Bacillus cereus*, and *Bacillus thuringiensis* Isolates", Applied and Environmental Microbiology, vol. 70, No. 2, American Society for Microbiology, Feb. 2004, 1068-1080.
Hopkins, D. I. , "*Xylella fastidiosa*: Xylem-Limited Bacterial Pathogen of Plants", Ann. Rev. Phytopathol., vol. 27, Annual Reviews Inc., 1989, 271-290.
Huber, Martin et al., "Accessing Single Nucleotide Polymorphisms in Genomic DNA by Direct Multiplex Polymerase Chain Reaction Amplification on Oligonucleotide Microarrays", Analytical Biochemistry, vol. 303, Elsevier Science (USA), 2002, 25-33.
Huckle, David , "Point-of-care diagnostices: will the hurdles be overcome this time?", Expert Review of Medical Devices, vol. 3.4, 2006, 421-426.
Ilyushina, Natalia A. et al., "Detection of amantadine-resistant variants among avian influenza viruses isolated in North America and Asia", Virology, vol. 341, Elsevier, Inc., 2005, 102-106.
Jacobi, V. et al., "Development of a multiplex immunocapture RT-PCR assay for detection and differentiation of tomato and tobacco mosaic tobamoviruses", Journal of Virological Methods, vol. 74, Elsevier Science B.V., 1998, 167-178.
Jacobsen, Nana et al., "Direct isolation of poly(A)+ RNA from 4 M guanidine thiocyanate-lysed cell extracts using locked nucleic acid-oligo(T) capture", Nucleic Acid Research, vol. 32, No. 7, Oxford University Press, 2004, 1031-1042.
Jobling, Mark A. et al., "Encoded Evidence: DNA in Forensic Analysis", Nature Reviews: Genetics, vol. 5, Oct. 2004, 739-751.
Kandimalla, Ekambar R. et al., "Design, biochemical, biophysical and biological properties of cooperative antisense oligonucleotides", Nucleic Acids Research, vol. 23, No. 17, Oxford University Press, 1995, 3578-3584.
Kaplan, Daniel L. et al., "DnaB from Thermus aquaticus Unwinds Forked Duplex DNA with an Asymmetric Tail Length Dependence", The Journal of Biological Chemistry, vol. 274, No. 11, American Society for Biochemistry and Molecular Biology, Inc., Mar. 12, 1999, 6889-6897.
Keohavong, Phouthone et al., "Fidelity of DNa polymerases in DNA amplification", Proc. Natl. Acad. Sci. USA, vol. 86, Dec. 1989, 9253-9257.
Kieleczawa, Jan et al., "DNA Sequencing by Primer Walking with Strings of Continguous Hexamers", Science, vol. 258, No. 5089, American Association for the Advancement of Science, Dec. 11, 1992, 1787-1791.

(56) References Cited

OTHER PUBLICATIONS

Kievits, Tim et al., "NASBA (TM) isothermal enzymatic in vitro nucleic acid amplification optimzed for the diagnosis of HIV-1 infection", Journal of Virological Methods, vol. 35, Elsevier Science Publishers B.V., 1991, 273-286.

Kilbourne, Edwin D. et al., "The total influenza vaccine failure of 1947 revisited: Major intrasubtypic antigenic change can explain failure of vaccine in a post-World War II epidemic", PNAS, vol. 99, No. 16, Aug. 6, 2002, 10748-10752.

Kimura, et al., "One-step immobilization ofr poly(dT)-modified DNA onto non-modified plastic substrates by UV irradiation for microarrays", Biochemical and Biophysical Research Communications, vol. 347, 2006, 477-484.

Koch, Walter H. , "Technology Platforms for Pahrmacogenomic Diagnostic Assays", Nature Reviews Drug Discovery, vol. 3, Sep. 2004, 749-761.

Kohn, J. , "An Immunochromatographic Technique", Immunology, vol. 15, 1968, 863-865.

Koonjul, Priyum K. , "Inclusion of polyvinylpyrrolidone in the polymerase chain reaction reverses the inhibitory effects of polyphenolic contamination of RHNA", Nucleic Acids Research, vol. 27, No. 3, Oxford University Press, 1999, 915-916.

Kornberg, et al., DNA Replication, 2nd Edition, WH Freeman and Company, New York, 1992, 298-299; 356-365.

Kozwich, Diane et al., "Development of a Novel, Rapid Integrated *Cryptosporidium parvum* Detection Assay", Applied and Environmental Microbiology, vol. 66, No. 7, American Society for Microbiology, Jul. 2000, 2711-2717.

Kwoh, D. Y. et al., "Transcription-based amplification system and detection of amplified human immunodeficiency virus type 1 with a bead-based sandwich hybridization format", Proc. Natl. Acad. Sci. USA, vol. 86, Feb. 1989, 117301177.

Landegren, Ulf et al., "A Ligase-Mediated Gene Detection Technique", Science, vol. 241, Aug. 26, 1988, 1077-1080.

Lane, Michael J. et al., "The thermodynamic advantage of DNA oligonucleotide 'stacking hybridization' reactions: energetics of a DNA nick", Nucleic Acids Research, vol. 25, No. 3, Oxford University Press, 1997, 611-616.

Leone, G. et al., "Direct detection of potato leafroll virus in potato tubers by immunocapture and the isothermal nuclic acid amplification method NASBA", Journal of Virological Methods, vol. 66, Elsevier Science B.V., 1997, 19-27.

Lim, Daniel V. et al., "Current and Developing Technologies for Monitoring Agents of Bioterrorism and Biowarfare", Clinical Microbiology Reviews, vol. 18, No. 4, American Society for Microbiology, Oct. 2005, 583-607.

Lockley, Andrew K. et al., "Colorimetric detection of immobilised PCR products generated on a solid support", Nucleic Acids Research, vol. 25, No. 6, Oxford University Press, 1997, 1313-1314.

Loens, K. et al., "Evaluation of NucliSens easyMAG for Automated Nucleic Acid Extraction from Various Clinical Specimens", Journal of Clinical Microbiology, vol. 45, No. 2, American Society for Microbiology, Feb. 2007, 421-425.

Lonnberg, Maria et al., "Chromatographic performance of a thin microporous bed of nitrocellulose", Journal of Chromatography B, vol. 763, Elsevier Science BV, 2001, 107-120.

Lowe, Mary et al., "Multiplexed, Particle-Based Detection of DNa Using Flow Cytometry with 3DNA Dendrimers for Signal Amplification", Cytometry Part A, vol. 60, No. 2, Wiley Intersciences, 2004, 135-144.

Mackay, I. M. , "Real-time PCR in the microbiology laboratory", Clin Microbiol Infect., vol. 10, European Society of Clinical Microbiology and Infectious Diseases, 2004, 190-212.

Malek, Larry et al., "Nucleic acid sequence-based amplification (NASBA)", Protocols for Nucleic Acid Analysis by Nonradioactive Probes, ed. Peter G. Isaac, Humana Press, Totowa, New Jersey, 1994, 253-260.

Michalet, Xavier et al., "Properties of Fluorescent Semiconductor Nanocrystals and their Application to Biological Labeling", Single Mol., vol. 2, No. 4, WILEY-VCH Verlag Berlin GmbH, 2001, 261-276.

Miyoshi, Daisuke et al., "Molecular Crowding Regulates the Structural Switch of the DNA G-Quadruplex", Biochemistry, vol. 41, American Chemical Society, Nov. 20, 2002, 15017-15024.

Monteiro, Lurdes et al., "Complex Polysaccharides as PCR Inhibitors in Feces: *Helicdobacter pylori* Model", Journal of Clinical Microbiology, vol. 35, No. 4, American Society for Microbiology, Apr. 1997, 995-998.

Nicholson, Karl G. et al., "Influenza", The Lancet, vol. 362, Nov. 22, 2003, 1733-1745.

O'Meara, Deirdre et al., "Capture of Single-Stranded DNa Assisted by Oligonucleotide Modules", Analytical Biochemistry, vol. 255, Academic Press, 1998, 195-203.

O'Meara, Deirdre et al., "Cooperative Oligonucleotides Mediating Direct Capture of Hepatitis C Virus RNa from Serum", Journal of Clinical Microbiology, vol. 36, No. 9, American Society for Microbiology, Sep. 1998, 2454-2459.

Palese, Peter et al., "Influenza vaccines: present and future", The Journal of Clinical Investigation, vol. 110, No. 1, Jul. 2002, 9-13.

Pannucci, James et al., "Virulence signatures: microarray-based approaches to discovery and analysis", Biosensors and Biolelectronics, vol. 20, Elsevier, B.V., 2004, 706-718.

Pastinen, Tomi et al., "A System for Specific, High-throughput Genotyping by Allele-specific Primer Extension on Microarrays", Genome Research, vol. 10, No. 7, Cold Spring Harbor Laboratory Press, 2000, 1031-1042.

Pemov, A. et al., "DNA analysis with multiplex microarray-enhanced PCR", Nucleic Acid Research, vol. 33, No. 2, Oxford University Press, 2005, 1-9.

Petrik, J. , "Diagnostic applications of microarrays", Transfusion Medicine, vol. 16, Blackwell Publishing, Ltd., 2006, 233-247.

Peytavi, Regos et al., "Microfluidic Device for Rapid (<15 min) Automated Microarray Hybridization", Clinical Chemistry, vol. 51, No. 19, 2005, 1836-1844.

Piepenburg, Olaf et al., "DNA Detection Using Recombination Proteins", PLoS Biology, vol. 4, No. 7, Jul. 2006, 1115-1121.

Pooler, M. R. et al., "Detection of *Xylella fastidiosa* in potential insect vectors by immunomagnetic separation and nested polymerase chain reaction", Letters in Applied Microbiology, vol. 25, Society for Applied Bacteriology, 1997, 1230126.

Pooler, Margaret R. et al., "Specifric PCR Detection and Identification of *Xylella fastidiosa* Strains Causing Citrus Variegated Chlorosis", Current Microbiology, vol. 31, Springer-Verlag New York, Inc., 1995, 377-381.

Pristoupil, T. I. , "Microchromatography and Microelectrophoresis on Nitrocellulose Membranes", Chromatographic Reviews, vol. 12, Elsevier Publishing Company, Amsterdam, Netherlands, 1970, 109-125.

Purcell, A. H. et al., "Fate of Pierce's Disease Strains of *Xylella fastidiosa* in Common Riparian Plants in Californiat", Plant Disease, vol. 83, No. 9, American Phytopathological Society, 1999, 825-830.

Purcell, Alexander H. et al., "Pierce's Disease Bacterium: Mechanism of Transmission by Leafhopper Vectors", Science, vol. 206, Nov. 16, 1979, 839-841.

Reinhartz, Avraham et al., "A novel rapid hybridization technique: paper chromatography hybridization assay (PACHA)", Gene, vol. 136, Elsevier Science Publishers B.V., 1993, 221-226.

Rodriguez, Jorge L. et al., "Detection and Diversity Assessment of *Xylella fastidiosa* in Field-Collected Plant and Insect Samples by Using 16S rRNA and gyrB Sequences", Applied and Environmental Microbiology, vol. 69, No. 1, American Society for Microbiology, Jul. 2003, 4249-4255.

Romero, Alicia et al., "Amplification and cloning of a long RNA virus genome using immunocapture-long RT-PCR", Journal of Virological Methods, vol. 66, No. 1, Elsevier Science B.V., 1997, 159-163.

Roper, Michael G. et al., "Advances in Polymerase Chain Reaction on Microfluidic Chips", Analytical Chemistry, vol. 77, No. 12, American Chemical Society, 2005, 3887-3894.

(56) References Cited

OTHER PUBLICATIONS

Rouse, Richard et al., "Microarray technology—an intellectual property retrospective", Pharmacogenomics, vol. 4, No. 5, Ashley Publications Ltd., 2003, 1462-2416.

Rule, Geoffrey S. et al., "Rapid method for visual identification of specific DNA sequences based on DNA-tagged liposomes", Clinical Chemistry, vol. 42, No. 8, 1996, 1206-1209.

Saiki, Randall K. et al., "Primer-Directed Enzymatic Amplification of DNA with a Thermostable DNA Poymerase", Science, vol. 239, Jan. 29, 1988, 487-491.

Sambrook, et al., Molecular Cloning: A Laboratory Manual, 3rd Edition, Cold Spring Harbor Laboratory Press, Cold Spring Harbor, New York, 2001, 9.47-9.55.

Schildkraut, Carl et al., "Dependence of the Melting Temperature of DNA on Salt Concentration", Biopolymers, vol. 3, 1965, 195-208.

Singh, Sanjay K. et al., "LNA (locked nucleic acids): synthesis and high-affinity nucleic acid recognition", Chem. Commun., vol. 4, 1998, 455-456.

Spiro, Alexander et al., "A Bead-Based Method for Multiplexed Identification and Quantitation of DNA Squences Using Flow Cytometry", Applied and Environmental Microbiology, vol. 66, No. 10, American Society for Microbiology, Oct. 2000, 4258-4265.

Stears, Robin L. et al., "A novel, sensitive detection system for high-density microarrays using dendrimer technology", Physiol. Genomics, vol. 3, American Physiological Society, 2000, 93-99.

Sterne, Max, "The use of Anthrax Vaccines Prepared from Avirulent (Uncapsulated) Variants of *Bacillus anthracis*", Onderstepoort Journal of Veterinary Science and Animal Industry, vol. 13, No. 2, Government Printer, Pretoria, Union of South Africa, Oct. 1939, 307-312.

Stiver, Grant, "The treatment of influenza with antiviral drugs", CMAJ, vol. 168, No. 1, Canadian Medical Association, Jan. 7, 2003, 49-57.

Tennikova, Tatiana B. et al., "An Introduction to Monolithic Disks as Stationary Phases for High Performance Biochromatography", J. High Resol. Chromatogr., vol. 23, No. 1, WILEY-VCH Verlag GmbH, 2000, 27-38.

Tennikova, Tatiana B. et al., "High-performance membrane chromatography: highly efficient separation method for proteins in ion-exchange, hydrophobic interaction and reversed-phase models", Journal of Chromatography, vol. 646, Elsevier Science Publishers B.V., 1993, 279-288.

Thommes, J. et al., "Membrane Chromatography—An Integrative Concept in the Downstream Processing of Proteins", Biotechnol. Prog., vol. 11, American Chemical Society and American Institute of Chemical Engineers, 1995, 357-367.

Tsai, Yu-Li et al., "Rapid Method for Separation of Bacterial DNA from Humic Substances in Sediments for Polymerase Chain Reaction", Applied and Environmental Microbiology, vol. 58, No. 7, American Society for Microbiology, Jul. 1992, 2292-2295.

Van Ness, Jeffrey et al., "Isothermal reactions for the amplification of oligonucleotides", PNAS, vol. 100, No. 8, Apr. 15, 2003, 4504-4509.

Vincent, Myriam et al., "Helicase-dependent isothermal DNa amplification", EMBO Reports, vol. 5, No. 8, European Molecular Biology Organization, 2004, 795-800.

Wahlestedt, Claes et al., "Potent and nontoxic antisense oligonucleotides containing locked nucleic acids", PNAS, vol. 97, No. 10, May 9, 2000, 5633-5638.

Walker, G. T. et al., "Isothermal in vitro amplification of DNA by a restriction enzyme/DNA apolymerase system", Proc. Natl. Acad. Sci.USA, vol. 89, Jan. 1992, 392-396.

Walker, G. T. et al., "Strand displacement amplification-an isothermal, in vitro DNA amplification technique", Nucleic Acid Research, vol. 20, No. 7, Oxford University Press, 1992, 1691-1696.

Webby, R. J. et al., "Are we ready for pandemic influenza?", Science, vol. 302, Nov. 28, 2003, 1519-1522.

Webster, Robert G. et al., "Potential Impact of Antiviral Drug Use during Influenza Pandemic", American Scientist, vol. 91, 2003, 122-129.

Wei, Cheng-Wey et al., "Using a microfluidic device for 1 ul DNA micrarray hybridization in 500 s", Nucleic Acids Research, vol. 33, No. 8, Oxford University Press, 2005, 1-11.

Wells, John M. et al., "Isolation, Culture, and Pathogenicity of the Bacterium Causing Phony Disease of Peach", Phytopathology, vol. 73, No. 6, American Phytopathological Society, 1983, 859-862.

Wetzel, T. et al., "A highly sensitive immunocapture polymerase chain reaction method for plum pox potyvirus detection", Journal of Virological Methods, vol. 39, Elsevier Science Publishers B.V., Jul. 1992, 27-37.

Wickenheiser, Ray A., "Trace DNA: A Review, Discussion of Theory, and Application of the Transfer of Trace Quantities of DNA Through Skin Contact", J Forensic Sci, vol. 137, No. 1, ASTM Int'l, 2002, 442-450.

Wilson, I G., "Inhibition and Facilitation of Nucleic Acid Amplification", Applied and Environmental Microbiology, vol. 63, No. 10, 1997, 3741-3751.

Yang, Samuel et al., "PCR-based diagnositcs for infectious diseases: uses, limitations, and future applications in acute-care settings", The Lancet Infectious Diseases, vol. 4, Jun. 2004, 337-348.

Young, Charles C. et al., "Polyvinylpyrrolidone-Agarose Gel Electrophoresis Purification of Polymerase Chain Reaction-Amplifiable DNA from Soils", Applied and Environmental Microbiology, vol. 59, No. 6, American Society for Microbiology, Jun. 1993, 1972-1974.

Zaytseva, Natalya V. et al., "Multi-analyte single-membrane biosensor for the serotype-specific detection of Dengue virus", Anal. Bioanal. Chem., vol. 380, 2004, 46-53.

Zijlmans, H.J.M.A.A. et al., "Detection of Cell and Tissue Surface Antigens Using Up-Converting Phosphors: A New Reporter Technology", Analytical Biochemistry, vol. 267, Academic Press, 1999, 30-36.

Zuiderwijk, Michel et al., "An amplication-free hybridization-based DNA assay to detect *Streptococcus pneumoniae* utilizing the up-convewrting phosphor technology", Clinical Biochemistry, vol. 36, The Canadian Society of Clinical Chemists, 2003, 401-403.

Aveyard, et al., "One step visual detection of PCR products with gold nanoparticles and a nucleic acid lateral flow (NALF) device", Chem. Commun., 2007, 4251-4253.

Carney, et al., "Present and future applications of gold in rapid assays", IVD Technology, Mar. 1, 2006, 1-8.

Corstjens, et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, 2001, 1885-1893.

Goldmeyer, et al., "Development of a Novel One-Tube Isothermal Reverse Transcription Thermophilic Helicase-Dependent Amplification Platform for Rapid RNA Detection", Journal of Molecular Diagnostics, Nov. 2007, 639-644.

Burns, et al., "An Integrated Nanoliter DNA Analysis Device", Science, Oct. 16, 1998, 484-487.

Cai, et al., "Oscillating Amplification Reaction for Nucleic Acids", U.S. Appl. No. 61/477,437, filed Apr. 20, 2011.

Cheng, et al., "Chip PCR. II Investigation of different PCR amplification systems in Microfabricated silicon-glass chips", Nucleic Acids Research, 1996, 380-385.

Findlay, et al., "Automated Closed-Vessel System for inVitro Diagnostics Based on Polymerase Chain Reaction", Clinical Chemistry, 1993, 1927-1933.

Fu, et al., "Controlled reagent transport in disposable 2D paper networks", Lab Chip, 2010, 918-920.

Liao, et al., "Miniature RT-PCT system for diagnosis of RNA-based viruses", Nucleic Acids Research, Oct. 12, 2005, 1-7.

Rao, et al., "Developing rapid, point-of-care, multiplex detection for use in lateral flow devices", Smart Medical and Biomedical Sensor Technology III, Proc. of SPIE, 2005.

(56) References Cited

OTHER PUBLICATIONS

Shoffner, et al., "Chip PCR. I. Surface passivation of microfabricated silicon-glass chips for PCR", Nucleic Acids Research, 1996, 375-379.

Wilding, et al., "PCR in a Silicon Microstructure", Clinical Chemistry, 1994, 1815-1818.

"Jikken Igaku Bessatsu Mokuteki De Eraberu PCR Jikken Protocol", Jan. 1, 2011, p. 50, Fig. 1B; p. 53, lines 1-12 (English translation of relevant passages attached).

Masny, et al., "Ligation mediated PCR performed at low denaturation temperatures-PCT melting profiles", Nucleic Acids Research, 2003, 1-6.

* cited by examiner

SEQUENCE LISTING

```
<160> NUMBER OF SEQ ID NOS: 56

<210> SEQ ID NO 1
<211> LENGTH: 24
<212> TYPE: DNA
<213> ORGANISM: Artificial
<220> FEATURE:
<223> OTHER INFORMATION: Synthetic primer

<400> SEQUENCE: 1
cagaagtgca tgcgtcgttc tttg                                          24

<210> SEQ ID NO 2
<211> LENGTH: 27
<212> TYPE: DNA
<213> ORGANISM: Artificial
<220> FEATURE:
<223> OTHER INFORMATION: Synthetic primer

<400> SEQUENCE: 2
agtgaatgat caattgcgac cgtactt                                       27

<210> SEQ ID NO 3
<211> LENGTH: 31
<212> TYPE: DNA
<213> ORGANISM: Artificial
<220> FEATURE:
<223> OTHER INFORMATION: Synthetic primer

<400> SEQUENCE: 3
tacatggtct tcccagataa tgcatcgctt g                                  31

<210> SEQ ID NO 4
<211> LENGTH: 26
<212> TYPE: DNA
<213> ORGANISM: Artificial
<220> FEATURE:
<223> OTHER INFORMATION: Synthetic primer

<400> SEQUENCE: 4
ccggatgagc attcaacata ccacgg                                        26

<210> SEQ ID NO 5
<211> LENGTH: 32
<212> TYPE: DNA
<213> ORGANISM: Artificial
<220> FEATURE:
<223> OTHER INFORMATION: Synthetic oligonucleotide

<400> SEQUENCE: 5
tttttttttt ttatattggt gggagtgtat ct                                 32
```

```
<210> SEQ ID NO 6
<211> LENGTH: 35
<212> TYPE: DNA
<213> ORGANISM: Artificial
<220> FEATURE:
<223> OTHER INFORMATION: Synthetic oligonucleotide

<400> SEQUENCE: 6
tttttttttt ttctttagcg gtagcagagg ctctt                                35

<210> SEQ ID NO 7
<211> LENGTH: 34
<212> TYPE: DNA
<213> ORGANISM: Artificial
<220> FEATURE:
<223> OTHER INFORMATION: Synthetic oligonucleotide

<400> SEQUENCE: 7
gcaggattta gtaatcgaat tttttttttt tttt                                 34

<210> SEQ ID NO 8
<211> LENGTH: 35
<212> TYPE: DNA
<213> ORGANISM: Artificial
<220> FEATURE:
<223> OTHER INFORMATION: Synthetic oligonucleotide

<400> SEQUENCE: 8
gggattgatg aggaaacagc attttttttt ttttt                                35

<210> SEQ ID NO 9
<211> LENGTH: 35
<212> TYPE: DNA
<213> ORGANISM: Artificial
<220> FEATURE:
<223> OTHER INFORMATION: Synthetic oligonucleotide

<400> SEQUENCE: 9
tacatggtct tcccagataa tttttttttt ttttt                                35

<210> SEQ ID NO 10
<211> LENGTH: 38
<212> TYPE: DNA
<213> ORGANISM: Artificial
<220> FEATURE:
<223> OTHER INFORMATION: Synthetic oligonucleotide

<400> SEQUENCE: 10
tgctagagaa ttaaatacat atattttttt tttttttt                             38

<210> SEQ ID NO 11
<211> LENGTH: 27
<212> TYPE: DNA
<213> ORGANISM: Artificial
<220> FEATURE:
<223> OTHER INFORMATION: Synthetic oligonucleotide

<400> SEQUENCE: 11
gtgccttgag actttttttt tttttt                                          27

<210> SEQ ID NO 12
<211> LENGTH: 40
<212> TYPE: DNA
<213> ORGANISM: Artificial
<220> FEATURE:
<223> OTHER INFORMATION: Synthetic oligonucleotide
```

```
<400> SEQUENCE: 12
ttcgaattac taaatcctgc agatacactc ccaccaatat                           40

<210> SEQ ID NO 13
<211> LENGTH: 47
<212> TYPE: DNA
<213> ORGANISM: Artificial
<220> FEATURE:
<223> OTHER INFORMATION: Synthetic oligonucleotide

<400> SEQUENCE: 13
gaatgctgtt tcctcatcaa tcccaagagc ctctgctacc gctaaag                   47

<210> SEQ ID NO 14
<211> LENGTH: 40
<212> TYPE: DNA
<213> ORGANISM: Artificial
<220> FEATURE:
<223> OTHER INFORMATION: Synthetic oligonucleotide

<400> SEQUENCE: 14
ttcgaattac taaatcctgc agatacactc ccaccaatat                           40

<210> SEQ ID NO 15
<211> LENGTH: 47
<212> TYPE: DNA
<213> ORGANISM: Artificial
<220> FEATURE:
<223> OTHER INFORMATION: Synthetic oligonucleotide

<400> SEQUENCE: 15
gaatgctgtt tcctcatcaa tcccaagagc ctctgctacc gctaaag                   47

<210> SEQ ID NO 16
<211> LENGTH: 27
<212> TYPE: DNA
<213> ORGANISM: Artificial
<220> FEATURE:
<223> OTHER INFORMATION: Synthetic primer

<400> SEQUENCE: 16
tcctgtcacc tctgactaag gggattt                                         27

<210> SEQ ID NO 17
<211> LENGTH: 26
<212> TYPE: DNA
<213> ORGANISM: Artificial
<220> FEATURE:
<223> OTHER INFORMATION: Synthetic primer

<400> SEQUENCE: 17
ragggcattt tggacaaagc gtctac                                          26

<210> SEQ ID NO 18
<211> LENGTH: 36
<212> TYPE: DNA
<213> ORGANISM: Artificial
<220> FEATURE:
<223> OTHER INFORMATION: Synthetic Primer

<400> SEQUENCE: 18
tttttttttt ragggcattt tggacaaagc gtctac                               36

<210> SEQ ID NO 19
<211> LENGTH: 38
```

```
<212> TYPE: DNA
<213> ORGANISM: Artificial
<220> FEATURE:
<223> OTHER INFORMATION: Synthetic primer

<400> SEQUENCE: 19
tttttttttt cctgtcacct ctgactaagg ggattttr                    38

<210> SEQ ID NO 20
<211> LENGTH: 26
<212> TYPE: DNA
<213> ORGANISM: Artificial
<220> FEATURE:
<223> OTHER INFORMATION: Synthetic primer

<400> SEQUENCE: 20
ragggcattt tggacaaagc gtctac                                 26

<210> SEQ ID NO 21
<211> LENGTH: 29
<212> TYPE: DNA
<213> ORGANISM: Artificial
<220> FEATURE:
<223> OTHER INFORMATION: Synthetic primer

<400> SEQUENCE: 21
tcctgtcacc tctgactaag gggattttr                              29

<210> SEQ ID NO 22
<211> LENGTH: 24
<212> TYPE: DNA
<213> ORGANISM: Artificial
<220> FEATURE:
<223> OTHER INFORMATION: Synthetic oligonucleotide

<400> SEQUENCE: 22
agatgagtct tctaaccgag gtcg                                   24

<210> SEQ ID NO 23
<211> LENGTH: 24
<212> TYPE: DNA
<213> ORGANISM: Artificial
<220> FEATURE:
<223> OTHER INFORMATION: Synthetic primer

<400> SEQUENCE: 23
tgcaaaaaca tcttcaagtc tctg                                   24

<210> SEQ ID NO 24
<211> LENGTH: 32
<212> TYPE: DNA
<213> ORGANISM: Artificial
<220> FEATURE:
<223> OTHER INFORMATION: Synthetic oligonucleotide

<400> SEQUENCE: 24
tttttttttt tttctatcgt cccgtcaggc cc                          32

<210> SEQ ID NO 25
<211> LENGTH: 24
<212> TYPE: DNA
<213> ORGANISM: Artificial
<220> FEATURE:
<223> OTHER INFORMATION: Synthetic oligonucleotide

<400> SEQUENCE: 25
```

```
gccgagatcg cgttttttttt tttt                                    24

<210> SEQ ID NO 26
<211> LENGTH: 35
<212> TYPE: DNA
<213> ORGANISM: Artificial
<220> FEATURE:
<223> OTHER INFORMATION: Synthetic oligonucleotide

<400> SEQUENCE: 26
tacatggtct tcccagataa ttttttttt ttttt                          35

<210> SEQ ID NO 27
<211> LENGTH: 38
<212> TYPE: DNA
<213> ORGANISM: Artificial
<220> FEATURE:
<223> OTHER INFORMATION: Synthetic oligonucleotide

<400> SEQUENCE: 27
tgctagagaa ttaaatacat atattttttt ttttttt                       38

<210> SEQ ID NO 28
<211> LENGTH: 52
<212> TYPE: DNA
<213> ORGANISM: Artificial
<220> FEATURE:
<223> OTHER INFORMATION: Synthetic oligonucleotide

<400> SEQUENCE: 28
cgcgatctcg gctttgaggg ggcctgacgg aacgatagag agaacatacg tt       52

<210> SEQ ID NO 29
<211> LENGTH: 27
<212> TYPE: DNA
<213> ORGANISM: Artificial
<220> FEATURE:
<223> OTHER INFORMATION: Synthetic primer

<400> SEQUENCE: 29
rcmgatctyg aggctctcat ggartgg                                  27

<210> SEQ ID NO 30
<211> LENGTH: 25
<212> TYPE: DNA
<213> ORGANISM: Artificial
<220> FEATURE:
<223> OTHER INFORMATION: Synthetic primer

<400> SEQUENCE: 30
gagcgtgaay acaaayccya aratc                                    25

<210> SEQ ID NO 31
<211> LENGTH: 23
<212> TYPE: DNA
<213> ORGANISM: Artificial
<220> FEATURE:
<223> OTHER INFORMATION: Synthetic oligonucleotide

<400> SEQUENCE: 31
ttcacgctca cttttttttt ttt                                      23

<210> SEQ ID NO 32
<211> LENGTH: 25
<212> TYPE: DNA
<213> ORGANISM: Artificial
```

```
<220> FEATURE:
<223> OTHER INFORMATION: Synthetic oligonucleotide

<400> SEQUENCE: 32
tttttttttt ttcgaggact gcagc                                              25

<210> SEQ ID NO 33
<211> LENGTH: 20
<212> TYPE: DNA
<213> ORGANISM: Artificial
<220> FEATURE:
<223> OTHER INFORMATION: Synthetic primer

<400> SEQUENCE: 33
gcraaagcag gggthyratc                                                    20

<210> SEQ ID NO 34
<211> LENGTH: 19
<212> TYPE: DNA
<213> ORGANISM: Artificial
<220> FEATURE:
<223> OTHER INFORMATION: Synthetic primer

<400> SEQUENCE: 34
cagagyttyc crttrtgtg                                                     19

<210> SEQ ID NO 35
<211> LENGTH: 24
<212> TYPE: DNA
<213> ORGANISM: Artificial
<220> FEATURE:
<223> OTHER INFORMATION: Synthetic oligonucleotide

<400> SEQUENCE: 35
gacagagcag gttttttttt tttt                                               24

<210> SEQ ID NO 36
<211> LENGTH: 25
<212> TYPE: DNA
<213> ORGANISM: Artificial
<220> FEATURE:
<223> OTHER INFORMATION: Synthetic oligonucleotide

<400> SEQUENCE: 36
tttttttttt ttcccaagac atact                                              25

<210> SEQ ID NO 37
<211> LENGTH: 20
<212> TYPE: DNA
<213> ORGANISM: Artificial
<220> FEATURE:
<223> OTHER INFORMATION: Synthetic primer

<400> SEQUENCE: 37
ggtgtytgga thggragrac                                                    20

<210> SEQ ID NO 38
<211> LENGTH: 21
<212> TYPE: DNA
<213> ORGANISM: Artificial
<220> FEATURE:
<223> OTHER INFORMATION: Synthetic primer

<400> SEQUENCE: 38
actcccrctr tatcctgacc a                                                  21
```

```
<210> SEQ ID NO 39
<211> LENGTH: 27
<212> TYPE: DNA
<213> ORGANISM: Artificial
<220> FEATURE:
<223> OTHER INFORMATION: Synthetic oligonucleotide

<400> SEQUENCE: 39
tgaaatgatt tgggattttt tttttt                                            27

<210> SEQ ID NO 40
<211> LENGTH: 24
<212> TYPE: DNA
<213> ORGANISM: Artificial
<220> FEATURE:
<223> OTHER INFORMATION: Synthetic oligonucleotide

<400> SEQUENCE: 40
tttttttttt tttggaacgg acag                                              24

<210> SEQ ID NO 41
<211> LENGTH: 27
<212> TYPE: DNA
<213> ORGANISM: Artificial
<220> FEATURE:
<223> OTHER INFORMATION: Synthetic primer

<400> SEQUENCE: 41
ggatcaayga ycgraayttc tggagrg                                           27

<210> SEQ ID NO 42
<211> LENGTH: 27
<212> TYPE: DNA
<213> ORGANISM: Artificial
<220> FEATURE:
<223> OTHER INFORMATION: Synthetic primer

<400> SEQUENCE: 42
ytytgtgcwg ctgtttgraa tttycct                                           27

<210> SEQ ID NO 43
<211> LENGTH: 25
<212> TYPE: DNA
<213> ORGANISM: Artificial
<220> FEATURE:
<223> OTHER INFORMATION: Synthetic oligonucleotide

<400> SEQUENCE: 43
agaatgtgca acattttttt ttttt                                             25

<210> SEQ ID NO 44
<211> LENGTH: 23
<212> TYPE: DNA
<213> ORGANISM: Artificial
<220> FEATURE:
<223> OTHER INFORMATION: Synthetic oligonucleotide

<400> SEQUENCE: 44
tttttttttt ttggcggaaa aca                                               23

<210> SEQ ID NO 45
<211> LENGTH: 26
<212> TYPE: DNA
<213> ORGANISM: Artificial
<220> FEATURE:
<223> OTHER INFORMATION: Synthetic primer
```

<400> SEQUENCE: 45
gatgtcaaaa atgcrrttgg vrtcct                                          26

<210> SEQ ID NO 46
<211> LENGTH: 27
<212> TYPE: DNA
<213> ORGANISM: Artificial
<220> FEATURE:
<223> OTHER INFORMATION: Synthetic primer

<400> SEQUENCE: 46
yctcatyacy gcytcyccaa gcgaatc                                         27

<210> SEQ ID NO 47
<211> LENGTH: 24
<212> TYPE: DNA
<213> ORGANISM: Artificial
<220> FEATURE:
<223> OTHER INFORMATION: Synthetic oligonucleotide

<400> SEQUENCE: 47
ggaggacttg aattttttt tttt                                             24

<210> SEQ ID NO 48
<211> LENGTH: 27
<212> TYPE: DNA
<213> ORGANISM: Artificial
<220> FEATURE:
<223> OTHER INFORMATION: Synthetic oligonucleotide

<400> SEQUENCE: 48 ttttttttt ttacagttcg agtctct                                          27

<210> SEQ ID NO 49
<211> LENGTH: 26
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 49
atggayacng tcaacagrac acayca                                          26

<210> SEQ ID NO 50
<211> LENGTH: 27
<212> TYPE: DNA
<213> ORGANISM: Artificial
<220> FEATURE:
<223> OTHER INFORMATION: Synthetic primer

<400> SEQUENCE: 50
ggyartggyc catcaatygg gttragt                                         27

<210> SEQ ID NO 51
<211> LENGTH: 24
<212> TYPE: DNA
<213> ORGANISM: Artificial
<220> FEATURE:
<223> OTHER INFORMATION: Synthetic oligonucleotide

<400> SEQUENCE: 51

```
aaaggggaag tgttttttttt tttt                                24

<210> SEQ ID NO 52
<211> LENGTH: 24
<212> TYPE: DNA
<213> ORGANISM: Artificial
<220> FEATURE:
<223> OTHER INFORMATION: Synthetic oligonucleotide

<400> SEQUENCE: 52
tttttttttt ttcagaaact gggg                                 24

<210> SEQ ID NO 53
<211> LENGTH: 27
<212> TYPE: DNA
<213> ORGANISM: Artificial
<220> FEATURE:
<223> OTHER INFORMATION: Synthetic primer

<400> SEQUENCE: 53
tayggrccag caytragyat caatgaa                              27

<210> SEQ ID NO 54
<211> LENGTH: 26
<212> TYPE: DNA
<213> ORGANISM: Artificial
<220> FEATURE:
<223> OTHER INFORMATION: Synthetic primer

<400> SEQUENCE: 54 tcycgttttyc gtttcatyac caryac                              26

<210> SEQ ID NO 55
<211> LENGTH: 24
<212> TYPE: DNA
<213> ORGANISM: Artificial
<220> FEATURE:
<223> OTHER INFORMATION: Synthetic oligonucleotide

<400> SEQUENCE: 55
agctaatgtg ctttttttttt tttt                                24

<210> SEQ ID NO 56
<211> LENGTH: 24
<212> TYPE: DNA
<213> ORGANISM: Artificial
<220> FEATURE:
<223> OTHER INFORMATION: Synthetic oligonucleotide

<400> SEQUENCE: 56
tttttttttt ttagtaacct tgca                                 24
```

NUCLEIC ACID DETECTION SYSTEM AND METHOD FOR DETECTING INFLUENZA

RELATED APPLICATIONS

This patent application claims the benefit of the filing date of U.S. Provisional patent application No. 60/839,537 filed Aug. 22, 2006 under 35 U.S.C. 119(e).

STATEMENT AS TO RIGHTS TO INVENTIONS MADE UNDER FEDERALLY SPONSORED RESEARCH OR DEVELOPMENT

This invention was made with government support under Contract No. DE-AC52-06NA25396, awarded by the United States Department of Energy. The government has certain rights in this invention.

BACKGROUND OF THE INVENTION

I. Influenza Viruses

Influenza viruses have a segmented genome of single-stranded negative-sense RNA and belong to the family Orthomyxoviridae. They have been isolated from a variety of animals, including humans, pigs, horses, sea mammals, and birds. In humans, influenza viruses cause a highly contagious acute respiratory disease that has been responsible for epidemic and pandemic disease in humans for centuries. In the $20^{th}$ century, influenza virus has already claimed millions of human lives in three different pandemics (40 million worldwide deaths during the Spanish flu by the influenza H1N1 strain in 1918; 70,000 American deaths in 1957 by the influenza H2N2 strain; and 34,000 American deaths in 1968 by the influenza H3N2 strain). Infection with Influenza viruses can lead to a wide spectrum of clinical disease from an asymptomatic infection to an acute, self-limiting influenza syndrome to severe sometimes fatal complications. The severity of disease depends generally on the age and health of the patient with most influenza-associated fatalities seen in the elderly or those who have underlying pulmonary or cardiac diseases.

Influenza A and B are the two types of influenza viruses that cause epidemic human disease. Influenza A viruses are further categorized into subtypes on the basis of two surface antigens: hemagglutinin and neuraminidase. Influenza B viruses are not categorized into subtypes. Since 1977, influenza A (H1N1) viruses, influenza A (H3N2) viruses, and influenza B viruses have circulated globally. In 2001, influenza A (H1N2) viruses that probably emerged after genetic reassortment between human A (H1N1) and A (H3N2) viruses began circulating widely. Both influenza A and B viruses are further separated into groups on the basis of antigenic characteristics. New influenza virus variants result from frequent antigenic change (i.e., antigenic drift) resulting from point mutations that occur during viral replication. Influenza B viruses undergo antigenic drift less rapidly than influenza A viruses.

Influenza A viruses are the major cause of human flu epidemics. Influenza A can be classified into subtypes based on the antigenic differences of two surface glycoproteins, hemagglutinin (HA) and neuraminidase (NA). Among 15 distinct HA subtypes and 9 NA subtypes discovered, only several of them (H1, H2, H3, N1, N2) are responsible for significant human epidemics. One reason behind the frequent epidemics is that Influenza A is subject to regular antigenic changes, brought about either by point mutations (genetic drift) in the genes coding for hemagglutinin or neuraminidase, or by re-assortment of genes from two distinct types of influenza (genetic shift). In both situations, prior immunity to influenza might not prevent infection with the new type, leading to localized epidemics or, in the case of genetic shift, a global pandemic of influenza.

Influenza A is also responsible for all Avian flu. Of particular interest are the highly pathogenic strains of avian influenza virus (AIV), which cause severe disease in many bird species, including domestic poultry. While most of avian flu is mild, there are some extremely virulent viruses in poultry with a mortality rate as high as 100% (Webby et al., 2003, Science 302: 1519). There have been 13 reported outbreaks of HPAI (Highly Pathogenic Avian Influenza) due to subtype H7 and 12 outbreaks due to subtype H5 since 1959. In early 2003, an outbreak of highly pathogenic H7N7 in the Netherlands (spreading to Belgium and Germany) resulted in the death or culling of about 30 million birds which caused significant economic loss and social panic. However, the biggest concern is the recent crossing of the species barrier to infect humans. In 1996, an avian influenza virus [A/England/268/96(H7N7)] was isolated from a woman with conjunctivitis, and a virus of the same subtype was isolated from a man with infectious hepatitis. The highly pathogenic H7N7 outbreak in the Netherlands of 2003 resulted in one human fatality and approximately 100 other confirmed human AIV infections. The most significant transmission took place in Hong Kong where an outbreak of HPAI subtype H5N1 occurred in chickens resulting in high mortality for infected birds in 1997 (Webster et al., 2003, Amer Scientists 91: 122; Palese et al., 2002, J. Clin. Invest. 110: 9). The same virus was then isolated from 18 individuals in Hong Kong, six of whom died. This was the first reported instance of an avian influenza virus H5N1 directly crossing the species barrier and infecting humans.

Since then, cases of influenza A (H5N1) infection have been reported in Cambodia, China, Indonesia, Thailand, Vietnam, and most recently, several cases in Turkey. As of Feb. 6, 2006, the WHO had confirmed 150 human H5N1 cases of which more than half have died (>50% mortality rate). Experts predict that another influenza pandemic is inevitable and possibly imminent due to the rapid evolution of emerging and re-emerging influenza strains. The severity of the next pandemic cannot be predicted, but modeling studies suggest that the impact of a pandemic on the United States could be substantial. In the absence of any control measures (vaccination or drugs), it has been estimated that in the United States a "medium-level" pandemic could cause 89,000 to 207,000 deaths, 314,000 and 734,000 hospitalizations, 18 to 42 million outpatient visits, and another 20 to 47 million people being sick. Between 15% and 35% of the U.S. population could be affected by an influenza pandemic, and the economic impact could range between $71.3 and $166.5 billion (http://www.cdc.gov/flu). The estimation on worldwide impact can easily be ten times the US figures.

Influenza B also causes frequent epidemics, though it is generally less virulent than Influenza A. Humans are the sole host of Influenza B. There are no distinguishable surface antigen markers for subtypes of Influenza B due to a lack of genetic shift. However, Influenza B does undergo antigenic changes, although at a much slower rate than Influenza A, via other insertion-deletion and reassortment mechanisms among circulation strains.

Annual immunization remains the best way to prevent infection in populations. Each year the influenza circulating strains are monitored by a global surveillance program to determine the vaccine composition for that year. Minor genetic drift occurring in the circulating viruses can reduce the effectiveness of the vaccine in preventing illness but, even then, partial immunity afforded by the vaccine will often attenuate the infection, reducing the occurrence of severe illness and complications (Kilbourne et al., 2002, Proc. Natl. Acad. Sci. USA 99: 10748; Palese et al., 2002, supra; Nicholson et al., 2003, Lancet (NA Ed.) 362: 1733). As for H5N1 pandemic prevention, the United States is unlikely to have access to the H5N1 vaccine until the 2008 flu season despite the recent effort of expediting the vaccine development and production.

To treat a regular influenza infection, four different antiviral medications (amantadine, rimantadine, oseltamivir and zanamivir are approved by the U.S. Food and Drug Administration (FDA). Amantadine and rimantadine belong to a group of neuraminidase inhibitors that are capable of blocking the ability of the virus to cleave itself from the host cell preventing further infection of neighboring cells. To prepare for a possible H5N1 pandemic, the US government is planning to spend ~$2 billion to stock sufficient Tamiflu™ dosages to cover 25% US population by 2010 (Gani et al., 2005, Emerging Infectious Diseases 11: 1355). These drugs usually work against influenza A viruses effectively if administered within 48 hours of symptom onset (Stiver, 2003, Canadian Med. Assoc. J. 168: 827). However, these drugs may not always be effective, as influenza virus strains can become resistant to one or more of these medications. For example, some of the 2004 H5N1 viruses isolated from poultry and humans are resistant to amantadine and rimantadine (de Jong et al., 2005, New England J. Med. 353: 2667; Ilyushina et al., 2005, Virology 341: 102). More recently, testing of seasonal influenza A (H3N2) isolates from individuals in the United States during the 2005-06 influenza season has shown that a high percentage of circulating viruses are resistant to amantadine and rimantadine (Bright et al., 2005, Lancet (NA Ed.) 366: 1175; Fauci, 2006, Avian Influenza Update, Nature Reviews Microbiol. 4: 9; Ilyushina et al., 2005, supra).

The fact that antivirals must be administered within 48 hours of symptom onset, combined with the rapid development of new drug-resistant strains and the inability of governments to meet population anti-viral needs in a pandemic situation, together highlight the urgent need for rapid and accurate point of care diagnosis in order to enable effective treatment and prevention of influenza. Towards this end, numerous laboratories have focused on facile methods for the rapid and sensitive detection of influenza viruses. Standard detection methodologies include virus isolation, culturing and serotyping. Unfortunately, these techniques often take days or weeks to complete, which is often far too late for therapeutic intervention. Alternative strategies which are employed include viral antigen detection and shell vial culturing, which give rapid results but are far less sensitive than conventional cell culturing (Dawson et al., 2007, Analytical Chemistry 79: 378-384.).

II. Nucleic Acid-Based Assays

Nucleic acid-based assays for pathogen detection and identification are unparalleled with respect to providing sensitivity, specificity and resolution. Nonetheless, technologies for nucleic acid detection continue to be relatively elaborate and often costly, limiting their utility for point of care diagnostics and deployment under field conditions where a supporting laboratory infrastructure is absent. Reliance on polymerase chain reaction (PCR) and fluorescent detection of amplified nucleic acids has contributed significantly to the complexity and cost of nucleic acid diagnostics. Retaining assay sensitivity while circumventing requirements for thermocyclers and fluorescence detection hardware remains a significant challenge.

In contrast to DNA-based assays, immunoassays have found widespread acceptance in low cost, easily used formats, perhaps the most notable of which is the chromatographic lateral flow immunoassay (Andreotti et al., 2003, Biotechniques 35(4): 850-859). Lateral flow assays, also known as hand-held assays or dipstick assays, are used for a broad range of applications where rapid antigen detection is required in an easily used, low cost format. Lateral flow immunoassays have been successfully employed for pathogen identification, diagnostics, and environmental and agriculture surveillance (Baeumner, 2003, Anal. Bioanal. Chem. 377(3): 434-435).

Several chromatographic lateral flow assays have been described for the detection of nucleic acid sequences. Early work made use of cumbersome enzymatic detection strategies that relied on time consuming manipulations of dipsticks following introduction of the sample (Reinhartz et al., 1993, Gene 136:221-226; Groody, 1996, Mol. Biotechnol. 6: 323-327). More recently, lateral flow-based detection of PCR products has been reported using standard immunological methods for lateral flow detection of antigen-labeled amplicons (Kozwich et al., 2000, Appl. Environ. Microbiol. 66(7): 2711-2717). Other lateral flow assays make use of PCR amplification and colorimetric detection using nanogold conjugates and biotin-streptavidin capture. While this approach provides rapid single-plex detection of amplification products, it remains linked to the hardware requirements of PCR (Glynou et al., 2003, Anal. Chem. 75: 4155-4160; Kunkel & Boyce-Jacino, WO 00/29112).

The appeal of lateral flow detection in the context of a PCR-based assay is limited by the fact that real-time PCR detection would offer similar hardware complexity compared to post-thermocycling introduction of PCR reactions onto a lateral flow detector with single amplicon detection capacity. This scheme requires each PCR reaction to be interrogated with a separate dipstick thus increasing sample handling and decreasing throughput. In addition to the hardware requirements of PCR, these devices have employed schemes poorly suited to multiplexed detection, further limiting their utility to single-plex PCR assays.

Strategies to eliminate PCR amplification have sought to either detect unamplified nucleic acid targets or to employ isothermal amplification techniques. Enabled by the use of up-converting phosphor reporters, unamplified *Streptococcus pneumoniae* DNA has been detected using a lateral flow assay format (Zuiderwijk et al., 2003, Clin. Biochem. 36(5): 401-403). Up-converting phosphor technology, while sensitive, remains dependent upon hardware required to detect phosphor emission (Zijlmans et al., 1999, Anal. Biochem. 267(1): 30-36).

The use of simple colorimetric detection schemes that circumvent the requirements for complex instrumentation require an upstream amplification strategy to attain suitable sensitivity. Isothermal nucleic acid amplification coupled with lateral flow detection has been reported for assays making use of cycling probe technology (CPT) and nucleic acid sequence-based amplification (NASBA), two isothermal amplification techniques (Fong et al., 2000, J. Clin. Microbiol. 38(7): 2525-2529; Baeumner et al., 2002, Anal. Chem. 74(6): 1442-1448; Hartley and Baeumner, 2003, Anal. Bioanal. Chem. 376: 319-327; Baeumner et al., 2004, Anal. Chem. 76: 888-894). While the work by Fong et al., made use of a lateral flow immunoassay for DNA detection, the NASBA amplified products generated in the work from Baeumner et al. were detected using a lateral flow system enabled by the use of liposome encapsulated dye and a sandwich hybridization assay similar that reported by Rule et al., 1996). Later refinements to the liposome detection scheme have demonstrated the utility of this approach for multianalyte detection (Zaytseva et al., 2004, Anal. Bioanal. Chem. 380: 46-53).

Numerous technologies for the amplification of nucleic acids are known. The polymerase chain reaction (PCR) presently dominates the field, and is supported by widespread use and a multiplicity of commercial platforms and products. However, PCR presents inherent limitations for applications in which simple, rapid nucleic acid assays are desired. PCR requires the use of a thermocycler, an expensive, electrified machine that is not easily adapted to environments outside of laboratories with technically trained personnel. In a typical reaction, a thermocycler can process a total of 10-200 μl reaction volumes, typically utilizing a 2-20 μl sample input. Because of the small volume involved in the reaction, micropipets, specialized PCR tubes, and special training are needed to perform PCR. Thus, clinical PCR assays for the detection of pathogenic agents are generally conducted by clinical reference laboratories. PCR also requires on the order of 30 minutes to 4 hours to accomplish (depending on the types of PCR instruments and reaction volume), the direct result of having to cycle between radically different temperatures.

Various "isothermal" amplification methods, which can be conducted at a constant temperature, have been developed and are in use. While eliminating the need for thermocycling, currently-available isothermal amplification technologies require varying degrees of technical expertise and some rely on multiple primers and other factors which negatively effect assay time, expense, sensitivity and specificity. Many of the isothermal amplification technologies described to date are slow, insensitive, and unreliable. In addition, many of the viable isothermal amplification technologies are run at temperatures far higher than ambient temperatures, and therefore require heating.

Strand displacement amplification, or SDA (Walker et al., 1992a, Nucl. Acids Res. 20: 1691-1696; Walker et al., 1992b, Proc. Natl. Acad. Sci. USA 89: 392-396), is one commercially-available isothermal amplification technology. SDA is based upon the ability of a restriction enzyme to nick one strand of a hemiphosphorothioated form of its double-stranded recognition site, combined with the ability of a polymerase to initiate synthesis at the nick and displace the downstream DNA strand. Although SDA has been improved to work well at 60° C., the reaction requires several hours to perform at ambient temperatures. Furthermore, the assay involves the incorporation of a thiated dNTP substrate into newly synthesized strands, which sometimes impedes replication and extension. Finally, the resulting amplification product is double-stranded DNA, requiring denaturation prior to detection by hybridization analysis.

Another recently described isothermal amplification technology is the EXPAR system (Van Ness et al., 2003, Proc. Natl. Acad. Sci USA 100(8): 4504-4509). Although this technology initially held promise, it is extremely unreliable, non-specific, and difficult to use. Relying on thermophilic polymerases and reaction conditions that must be perfectly controlled, this technology is hampered by problems including spontaneous primer-independent polymerization of non-specific amplification products. More importantly, EXPAR requires that a specific nicking agent recognition sequence be located on the target DNA in a way that permits specific priming. Rarely is this the case in the context of pathogen target detection, and therefore this technology is fundamentally limited.

Helicase Dependent Amplification (HDA) is a recently described isothermal nucleic acid amplification method which relies on a helicase enzyme to open double stranded DNAs, thus obviating the need for heat denaturation of double stranded targets (Vincent et al., 2004, EMBO Report 5: 795; An et al., 2005, J. Biol. Chem. 280: 28952). Detailed information concerning the use of HDA to detect DNA may be found in published United States Patent Application No. 20040058378. Detailed information concerning the use of HDA in detecting RNA species may be found in published United States Patent Application No. 20060154286.

Other isothermal amplification technologies include the Ligase Chain Reaction (LCR) (Landgren et al., 1988; Barany et al., 1991), Transcription-based Amplification System (Kwoh et al., 1989), Self-Sustained Sequence Replication (Guatelli et al., 1990), NASBA (Nucleic Acid Based Amplification) (Kievitis et al., 1991; commercially available from BioMerieux), and Q-beta Replicase (Dobkin et al., 1979, Biochemistry 18: 2038-2044).

Methods for the amplification of RNA have also been described. Principally, RNA amplification has relied upon the use of reverse-transcriptase-PCR (RT-PCR). RT-PCR is widely used and is supported by multiple commercial platforms and products. RT-PCR works by generating a single stranded DNA copy which is then exponentially amplified by PCR. However, RT-PCR is burdened by all of the limitations inherent to PCR, including the requirement for thermocycling and the double-stranded nature of the resulting amplification product. Methodologies which attempt to overcome the limitations of RT-PCR are generally based on the combined use of an RNA-dependent, DNA polymerase, and a DNA-dependent DNA polymerase. See, for example, U.S. application no. 20050014192, which describes an isothermal strand displacement type of RNA amplification methodology. HDA has also been adapted successfully for the detection of RNA species by combining HDA with a reverse transcriptase reaction to convert RNA into cDNA, which is then exponentially amplified by HDA (RT-HDA; see published US Patent Application 20060154286).

Therefore, there is a growing need for simpler, faster, more cost effective nucleic acid amplification methodologies, particularly those which may be conducted at ambient temperatures without the need for electrified and other specialized equipment or personnel. This need is acute with respect to the detection of pathogenic organisms in the context of biological terrorism and warfare, as well as in the context of clinical diagnosis of infectious diseases which require immediate identification in order to provide effective treatment to infected individuals. For example, as previously mentioned, infections by the highly virulent strains of the avian influenza virus must be treated within 48 hours of initial infection, thereby rendering useless any assay technology that cannot be performed rapidly and with reliable specificity and sensitivity. Similarly, there is a great need for field-deployable nucleic acid assays, both on the battlefield and in remote regions of the world. Here, too, the development of simple and reliable isothermal amplification technologies is a prerequisite to the development of such assays.

Ideally, a simple lateral flow device employing dry, stable detection reagents compatible with a multiplexed hybridization-based capture strategy would be coupled to an easily used, rapid isothermal amplification scheme that generates single-stranded DNAs suitable for direct hybridization to the capture and detection oligonucleotides of a sandwich assay.

SUMMARY OF THE INVENTION

The invention provides a rapid, sensitive and specific nucleic acid detection system which utilizes isothermal nucleic acid amplification in combination with a lateral flow chromatographic device, or DNA dipstick, for DNA-hybridization detection. The system of the invention requires no complex instrumentation or electronic hardware, and provides a low cost nucleic acid detection system suitable for highly sensitive pathogen detection. Hybridization to single-stranded DNA amplification products using the system of the invention provides a sensitive and specific means by which assays can be multiplexed for the detection of multiple target sequences.

A principal aspect of the invention relates to the rapid detection of infectious influenza and related flu-like viruses via amplification and detection of signature genomic RNA sequences using the nucleic acid detection system of the invention. The system may be divided into three general components: (a) extraction of target viral RNA from clinical specimens, (b) specific amplification of viral target sequences, and (c) detection of the amplified target sequences using a lateral flow DNA-hybridization, visual read-out device.

In one aspect, the invention provides a method for detecting the presence of an influenza virus target nucleic acid in a clinical sample, comprising: (a) isolating influenza virus particles which contain the target nucleic acid from the clinical sample using magnetic affinity capture; (b) releasing total nucleic acid from the influenza virus particles; (c) amplifying influenza target nucleic acid using reverse transcriptase in combination with helicase dependent amplification, using amplification primers specific to the influenza target nucleic acid, to generate a solution containing a DNA amplification product corresponding to the influenza target nucleic acid sequence; (d) hybridizing a detection oligonucleotide complementary to a first sequence of the influenza target nucleic acid to the DNA amplification product, which first sequence does not overlap with the amplification primer binding regions on the influenza target nucleic acid, which detection oligonucleotide is coupled to a detectable label, to generate a solution containing labeled DNA amplification product; (e) applying an aliquot of the solution containing the labeled DNA amplification product to a sample receiving zone of a lateral flow chromatographic device, wherein the lateral flow chromatographic device comprises a lateral flow matrix which defines a flow path and which comprises in series: (i) a sample receiving zone for receiving an aliquot of a fluid sample; and, (ii) a capture zone in lateral flow contact with said receiving zone, said capture zone comprising a microporous membrane, at least a portion of which contains at least one capture oligonucleotide immobilized thereto, which capture oligonucleotide is complementary to a second and distinct sequence of the influenza target nucleic acid; and, (f) detecting the presence of the influenza target nucleic acid by detecting the label at the site of the immobilized capture oligonucleotide.

In another aspect, the invention provides a method for detecting the presence of an influenza virus target nucleic acid in a clinical sample, comprising: (a) isolating influenza virus particles which contain the target nucleic acid from the clinical sample using magnetic affinity capture; (b) releasing total nucleic acid from the influenza virus particles; (c) amplifying influenza target nucleic acid using reverse transcriptase in combination with helicase dependant amplification, using amplification primers specific to the influenza target nucleic acid, to generate a solution containing a DNA amplification product corresponding to the influenza target nucleic acid sequence; (d) applying an aliquot of the solution containing the DNA amplification product to a sample receiving zone of a lateral flow chromatographic device, wherein the lateral flow chromatographic device comprises a lateral flow matrix which defines a capillary flow path and which comprises in series: (i) a sample receiving zone for receiving an aliquot of a fluid sample; (ii) a labeling zone in lateral flow contact with said sample receiving zone, wherein the labeling zone comprises a porous material containing at least one detection oligonucleotide diffusively bound thereto, which detection oligonucleotide is complementary to a first sequence of the influenza target nucleic acid and is coupled to a detectable label; and, (iii) a capture zone in lateral flow contact with said labeling zone, said capture zone comprising a microporous membrane, at least a portion of which contains at least one capture oligonucleotide immobilized thereto, which capture oligonucleotide is complementary to a second and distinct sequence of the influenza target nucleic acid; (e) allowing the solution to traverse through the labeling and capture zones, under conditions sufficient to enable the hybridization of the DNA amplification product to the detection and capture oligonucleotides; and, (f) detecting the presence of the target nucleic acid by detecting the label at the site of the immobilized capture oligonucleotide.

In another aspect, the invention provides a method for detecting the presence of a virus target nucleic acid in a clinical sample, comprising: (a) isolating virus particles which contain the target nucleic acid from the clinical sample by incubating the clinical sample with magnetic beads functionalized with at least one antibody capable of binding to the virus particles, and separating magnetic bead-bound virus particles from other elements present in the clinical sample by applying a magnetic field to the sample; (b) releasing total nucleic acid from the virus particles by (i) alkaline lysis followed by neutralization or (ii) heating; (c) amplifying virus target nucleic acid using helicase dependant amplification, in combination with reverse transcriptase where the virus target nucleic acid is RNA, using amplification primers specific to the virus target nucleic acid sequence, to generate a solution containing a DNA amplification product corresponding to the virus target nucleic acid sequence; (d) applying an aliquot of the solution containing the DNA amplification product to a sample receiving zone of, a lateral flow chromatographic device, wherein the lateral flow chromatographic device comprises a lateral flow matrix which defines a capillary flow path and which comprises in series: (i) a sample receiving zone for receiving an aliquot of a fluid sample; (ii) a labeling zone in lateral flow contact with said sample receiving zone, wherein the labeling zone comprises a porous material containing at least one detection oligonucleotide diffusively bound thereto, which detection oligonucleotide is complementary to a first sequence of the virus target nucleic acid and is coupled to a detectable label; and, (iii) a capture zone in lateral flow contact with said labeling zone, said capture zone comprising a microporous membrane, at least a portion of which contains at least one capture oligonucleotide immobilized thereto, which capture oligonucleotide is complementary to a second and distinct sequence of the virus target nucleic acid; and, (f) detecting the presence of the virus target nucleic acid by detecting the label at the site of the immobilized capture oligonucleotide.

The isolation of influenza virus particles may be achieved by first incubating the clinical sample with magnetic beads functionalized with at least one affinity ligand capable of binding to the influenza A virus particles, followed by separating magnetic bead-bound cells and/or particles from other elements present in the clinical sample by applying a magnetic field to the sample. Various affinity ligands are known and may be used in the practice of the method of the invention. Typically, an antibody is used. One or more wash steps may be added following the separation step. Total nucleic acid from the influenza virus particles is preferably achieved by alkaline lysis followed by neutralization, or by heating to release nucleic acid. This provides an initial gateway for establishing the specificity of the detection system, in that RNA extracted from isolated virus substantially eliminates contamination by genomic RNA (and DNA) from host cells or other organisms which may be present in the clinical specimen. In addition, these methods eliminate the need for centrifugation, which typical in nucleic acid extraction methodologies, thereby enabling highly simplified, downstream nucleic acid amplifications. In order to improve the efficiency and yields of the amplification reaction, in some embodiments primers incorporating a poly dA or poly dT sequence of between 5 and 20 bases in length are be used.

More specifically, in one embodiment, virion particles are first isolated from a clinical specimen (i.e., nasopharyngeal aspirate or wash) using immunomagnetic affinity capture. Briefly, magnetic microbeads (microspheres) functionalized with a binding ligand, such as an antibody, against one or more cell surface markers of the target virus are incubated with the clinical specimen. After target virus particles are bound to the beads, a magnetic field is used to separate the bead-bound virus from other elements present in the clinical sample (i.e., other viruses, bacteria, human cells and debris). Typically, one or more washes are performed to enhance the degree of purification (i.e., saline washes). Immunomagnetically-isolated (or enriched) target virion particles are then subjected to lysis using sodium hydroxide in order to liberate viral RNA. Following lysis, the lysis solution is neutralized. Alternatively, heat is used to lyse virus particles and release genomic RNA. RNAse inhibitors are typically included. These methods of lysing virion particles results in single stranded target viral RNA ready for amplification. All of the foregoing steps may be carried out in a single reaction chamber, an important feature of the invention, thus achieving one the primary requirements for POC and field applications.

Extracted RNA is then subjected to isothermal amplification. In a preferred embodiment, RNA is converted to cDNA using reverse transcriptase (RT), and target sequences in the cDNA are amplified by the helicase dependent amplification (HDA) method using target-specific primers. In one embodiment, both the RT and HDA reactions are carried out at the same time in a single reaction vessel, in the presence of an RNase H. The reaction vessel may be the same as the one utilized for RNA extraction, in which case, the components necessary for the RT and HDA reactions are provided or added to the extraction vessel. Alternatively, extracted RNA may be added to a separate reaction vessel containing the components necessary for the RT and HDA reactions.

Amplified DNA corresponding to target viral sequences is then detected using the invention's sandwich oligonucleotide lateral flow platform. Briefly, amplified target DNA is contacted with a first hybridization oligonucleotide complementary to a part of the amplified target DNA ("detection oligonucleotide" or "detection probe"). The detection probe is functionalized with a detectable marker, which in preferred applications is a dyed microsphere. If amplified target nucleic acid is present, a hybridization complex is formed between the target and the detection probe-microsphere. Subsequently, this complex moves across the lateral flow substrate material (i.e., nitrocellulose membrane) until it reaches a zone onto which a second hybridization oligonucleotide complementary to a distinct part of the amplified target DNA has been immobilized. This "capture oligonucleotide" (or "capture probe") will arrest the flow of the detection probe-microsphere complex via hybridization to target DNA, whereupon a visual, colorimetric indication is provided by the localized concentration of labeled microsphere on the pre-deposited capture probe zone.

In one embodiment, the amplified target DNA is added to a solution containing the dyed microsphere/bead-functionalized first hybridization oligonucleotide. Thereafter, the solution comprising the bead-oligo captured target DNA is added to the lateral flow device. Alternatively, a solution containing the amplified target DNA is added to a component of the lateral flow device which includes the bead-oligo complex in a pre-deposited, lyophilized form. When added in this manner (i.e., to a conjugate release pad or labeling zone component of the lateral flow device), the target DNA-containing solution acts to rehydrate the bead-oligo complex, whereupon the target DNA may be captured by the bead-detection oligonucleotide complex. Lateral flow transmits the hybridized target DNA-bead complexes to the immobilized capture oligonucleotide(s) on the device.

In another alternative procedure, bead-functionalized detection oligonucleotides are added to the RT/HDA reaction prior to termination of the HDA reaction. This approach provides the advantage of presenting the detection oligonucleotides to the amplified target DNA as the latter is being produced, thereby minimizing the extent to which amplified DNA can form duplexes or secondary structures that could interfere with hybridization to the detection oligo. Accordingly, this approach eliminates the need for a separate denaturation step prior to hybridization to detection oligo, and thus may be preferred for POC and field applications in which performing a denaturation step is impractical.

The system of the invention provides unprecedented assay speed and simplicity. The system neither requires thermocycling equipment for the amplification of DNA, nor the use of sophisticated instrumentation for obtaining assay results. The amplification component of the system is run at constant temperature and does not require small volume handling or technical sophistication. The detection component runs automatically following sample administration, and produces a visual result that can be seen by the naked eye in a matter of minutes.

DETAILED DESCRIPTION OF THE INVENTION

Figure 1:
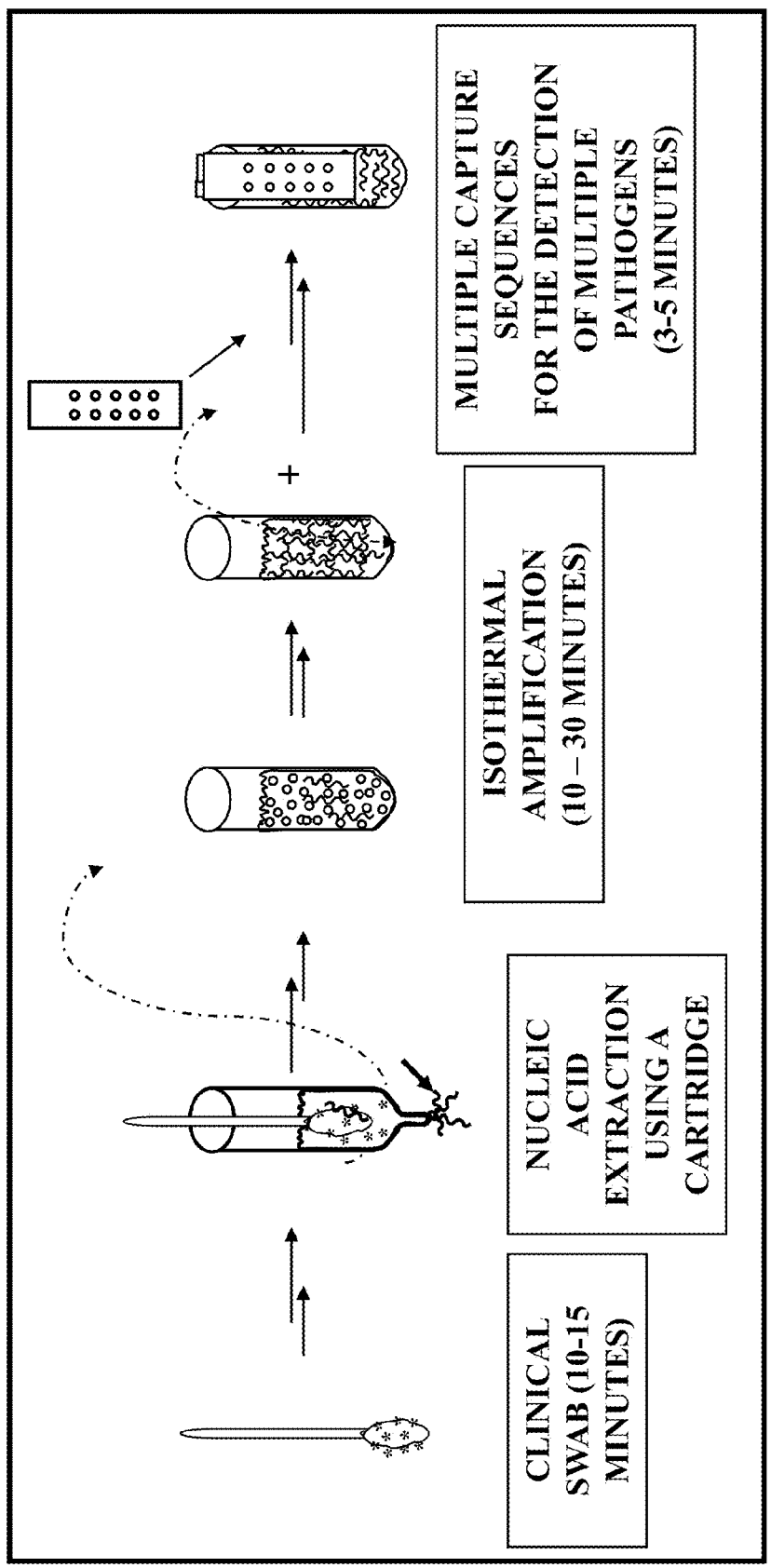
FIG. 1. Schematic illustration of sequence of events in nucleic acid assay of the invention (showing influenza example). (A) influenza capture and isolation from clinical sample, (B) viral genome extraction, (C) isothermal amplification, and (D) direct detection on the dipstick.

Unless otherwise defined, all terms of art, notations and other scientific terminology used herein are intended to have the meanings commonly understood by those of skill in the art to which this invention pertains, unless otherwise defined. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

Overview of the System

The nucleic acid dipstick detection system of the invention is designed to permit rapid assay of DNA or RNA signatures indicative of the presence of a target pathogenic organism or spore or disease condition or indicator. The system is rapid, sensitive, specific and amenable to both clinical medical diagnostics and field-based identification of biothreat agents. Various formats are contemplated, depending upon whether the application is designed for medical diagnosis or field identification.

The system has three primary components: (1) isolation of target microorganisms or cells using immunoaffinity purification and extraction of target nucleic acid therefrom, (2) rapid and sensitive isothermal amplification of nucleic acids using helicase dependent amplification (HDA), and (3) redundant capture of amplified target using (a) a label, such as a detectable particles (i.e., dyed microbeads) conjugated to an detection oligonucleotide complementary to one of two signature sequences on the amplified target ("detection oligonucleotide"), and (b) a membrane-immobilized "capture oligonucleotide" complementary to the other signature sequence on the target, such that capture of amplified target by the membrane-immobilized and bead-bound oligonucleotides brings labeled beads into contact with the membrane, displaying a visual or machine-readable optical signal generated by localized concentration of the label. Thus, the assay is in a sandwich-type nucleic acid format. Positive hybridization to two pathogen or other target signatures in order to produce a localized signal produces very high assay specificity. Both sensitivity and specificity are enhanced by the initial step of immunomagnetically-isolating target virions.

A principal objective of the invention is to provide a rapid, sensitive and specific assay for influenza and related viruses, which may be performed without the need for thermocyclers, centrifuges, and other technically demanding equipment, and which may be performed by individuals lacking technical skills, thus providing a platform that can be utilized in point of care environments and in field-deployment situations. The preferred assays of the invention utilize a combination of elements that produce detectable results consistent with the foregoing objectives.

In the first component of the detection system of the invention, the target organism(s) of interest are isolated, in order to provide for the extraction of an enriched or purified nucleic acid sample for subsequent amplification. In one embodiment, influenza virus is the target organism, and isolation of influenza virions is accomplished using immunomagnetic affinity purification methodologies known in the art. More specifically, as an example, where the target organism is influenza type A, magnetic microparticles are functionalized with antibody specific for a surface marker of influenza A. Such a marker may be relatively specific, but may result in the isolation of various strains of influenza A, which are then differentiated in the lateral flow nucleic acid component of the system. In some cases, depending upon the specific target organism, it may be possible to use antibody that is highly specific for the target, resulting in substantially pure virus following the immunomagnetic affinity isolation step. In other cases, species or strain-specific surface markers may not be available, thus necessitating the use of antibodies that are cross reactive for a number of related viruses or other pathogenic organisms. Indeed, in some cases, it may be desirable to utilize antibodies that are specific for a range of different yet related viruses or other pathogenic organisms. As one example, where the objective includes simultaneous detection and differentiation of a number of related viruses (i.e., all sub-types of a certain virus), polyclonal antibodies or antibodies which are otherwise broadly cross-reactive with all members of the target class may be employed. The use of such antibodies in an immunomagnetic affinity protocol will result in the isolation of a group of related viruses, which may then be distinguished on the basis of the post-nucleic acid extraction components of the invention's detection system, by virtue of various different primer pairs targeted to various different signature sequences, in the context of the specific sandwich oligonucleotide assay component of the invention.

In the second component of the detection system of the invention, amplification of target nucleic acid is achieved using the isothermal nucleic acid amplification method HDA. Amplified DNA is detected using a lateral flow chromatographic nucleic acid sandwich assay, as further described infra. Where the target microorganism contains an RNA genome, HDA is performed in combination with reverse transcription of RNA to cDNA, which is amplified by HDA. HDA is a recently described isothermal DNA amplification method that has been successfully adapted to the amplification of DNA and RNA target sequences, and is further described below. This aspect of the procedure is described in more detail by way of the Examples which follow.

Figure 2:
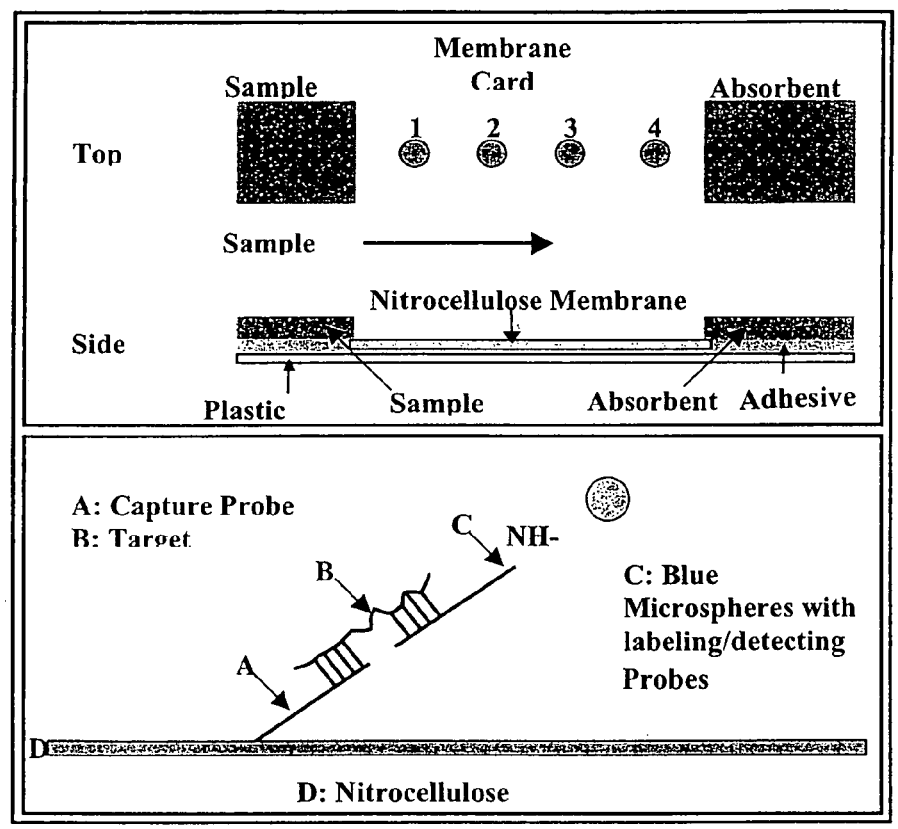
FIG. 2. Schematic diagram of the lateral flow chromatographic detection device used in one system of the invention. Top panel: Top and side views of the device assembly. Bottom panel: Depicts detection of a target sequence. Detection of the single-stranded pathogen amplification products is achieved with two target-specific oligonucleotide probes, (A) capture oligonucleotide probe immobilized on a nitrocellulose membrane, and (C) detection oligonucleotide probe conjugated to the surface of a detectable label such as dyed polystyrene microspheres. When a specific target sequence (B) is present, a sandwich complex is formed among the capture probe, target sequence, and detection probe resulting in a visible colored spot on the membrane.

The third component of the detection system of the invention comprises a lateral-flow chromatographic device capable of detecting amplified DNA using a combination of capture and detection oligonucleotides complementary to the amplified DNA. The lateral flow device is typically a multi-substrate chromatographic strip, also referred to herein as a "DNA dipstick". Schematic representations of such a device are shown in FIG. 2. The lateral flow device is capable of transporting nucleic acids within a liquid sample across different zones (substrates) within the device. In a simplified illustration, one embodiment of the lateral flow device is structurally organized into at least 3 zones, comprising in linear orientation: (a) a sample pad constructed from absorbent material onto which a liquid, nucleic acid-containing sample is deposited, (b) a conjugate release pad containing a least one oligonucleotide-fitted detection particle (e.g., microsphere, bead, quantum dot), and (c) a detection zone comprising a nitrocellulose or nylon membrane containing at least one immobilized capture oligonucleotide. In preferred embodiments, a fourth element comprises an absorbent material which is capable of facilitating the lateral flow of the liquid sample from the sample pad end of the device to and through the detection zone. In alternative embodiments, the conjugate release pad element is eliminated, and the amplified DNA sample to be assayed for the presence of a target nucleic acid is mixed with the oligonucleotide-fitted detection particle prior to placing the sample onto the sample pad.

Figure 3:
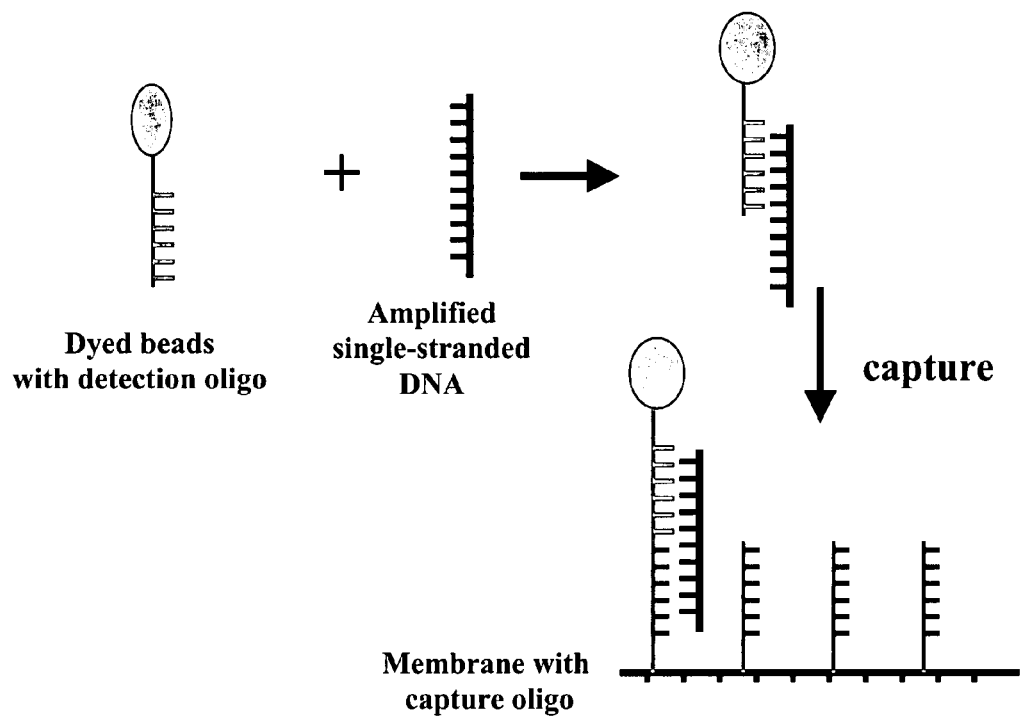
FIG. 3. Schematic diagram showing the relationship of the detection oligonucleotide-bead conjugates, capture oligonucleotides and target sequence capture.

The redundant capture feature of the invention results from the use of two oligonucleotides complementary to two different sequences on the target nucleic acid (see FIG. 3). More specifically, one oligonucleotide is complementary to one of two "signature" sequences on the target nucleic acid. Termed the "detection oligonucleotide" or "detection probe" herein, this oligonucleotide is conjugated to small detection particles, such as microspheres, microbeads and quantum dots that are detectably labeled (i.e., with colorimetric dyes). The detection particles display a visual or optically detectable, and localized, signal indicative of the presence of the target nucleic acid. In some embodiments, a dyed microbead-conjugated oligonucleotide is used to populate the conjugate release pad of the device. In other embodiments, a dyed microbead-conjugated oligonucleotide is mixed with a liquid DNA sample to be assayed. A second oligonucleotide, termed the "capture oligonucleotide" herein, is complementary to another, distinct "signature" sequence on the target nucleic acid, and is immobilized to the microporous membrane (i.e., nitrocellulose) of the device.

In the practice of a detection assay utilizing the system of the invention, the capture of amplified target nucleic acids by the membrane-immobilized and detection particle-bound oligonucleotides brings the detection particles into contact with the membrane, displaying a visual or machine-readable optical signal. Thus, the assay is a sandwich-type nucleic acid format, requiring positive hybridization to two distinct sequences on the target nucleic acid in order to produce a localized signal, resulting in very high assay specificity.

The system demonstrates exceptional assay sensitivity and specificity characteristics. For example, embodiments utilizing a lateral flow device containing oligonucleotide conjugated microbeads and nitrocellulose membrane-immobilized capture oligonucleotides, observed detection sensitivities are typically in the nanomolar to sub-nanomolar range (see Examples, infra). Embodiments utilizing oligonucleotide conjugated quantum dots in combination with nitrocellulose membrane-immobilized capture oligonucleotides may demonstrate somewhat higher detection sensitivities.

Components of the System and Detection Assays

The nucleic acid detection systems of the invention share a common assay progression which begins with isolating influenza virus particles which contain the target nucleic acid from the clinical sample using magnetic affinity capture. As used herein, the term "clinical sample" refers to a sample obtained from an individual that may contain a pathogenic organism of interest and/or a cell that may contain such a pathogenic organism of interest, genomic nucleic acid of the pathogen of interest, mRNA transcribed from such genomic nucleic acid, and/or proteins encoded thereby. For typical clinical applications, the clinical sample may be saliva, blood, nasal swab, throat swab, tear fluid, urine, or any other body fluid or sample containing or potentially containing a cell or spore harboring genetic material to be assessed. With respect to influenza viruses, an appropriate clinical sample includes without limitation nasal swab, nasopharyngeal aspirate or nasopharyngeal wash sample.

Magnetic affinity capture refers to methods which utilize the ability of a ligand binder-functionalized magnetic bead to bind to the surface of a particle or cell, thereby permitting the application of a magnetic filed to isolate the particle or cell of interest from other contents in a sample containing such particles or cells, and include for example immunomagnetic affinity capture methodologies. For example, a particle may be a virus particle, such as an influenza A virus particle, and the ligand-functionalized magnetic bead is magnetic bead coated or functionalized with an antibody which recognizes and binds to a surface antigen on the influenza A virus particle. Examples of such antibodies include polyclonal and monoclonal antibodies which recognize and bind to an influenza A HA or NA antigen, including those which are cross-reactive with HA and NA on multiple influenza subtype strains.

Thus, a clinical sample is incubated with magnetic beads functionalized with at least one affinity ligand capable of binding to target virus particles. The affinity ligand is typically an antibody capable of recognizing and binding to a surface antigen on the virus of interest. Magnetic bead-bound virus particles are then separated from other elements (i.e., other viruses, bacteria, human cells and debris) present in the clinical sample by applying a magnetic field to the sample. Typically, one or more washes are performed to enhance the degree of purification (i.e., saline washes).

An example of the use of immunomagnetic capture of influenza A is presented in Examples 2 and 4, infra. Briefly, polyclonal antibodies raised by standard immunization methods against influenza A Texas 1/77 strain were used to functionalize a suspension of magnetic beads coated with avidin. These anti-influenza A functionalized beads successfully captured the influenza A Sydney 5/97 strain. Isolated virion particles were lysed using a NaOH solution in order to extract flu RNA, and extracted RNA subjected to nucleic acid amplification, demonstrating that the quality of the RNA so extracted is sufficient for amplification and detection.

In addition to antibodies, various binding ligands known in the art may be used to functionalize magnetic beads in order to enable the functionalized beads to bind to a target cell or particle of interest. For example, a modified sialic acid, capable of recognizing and binding to an influenza HA surface antigen, may be used to functionalize magnetic beads which are then used to isolate influenza A particles.

Cells with may contain replicating virus, viral nucleic acid, mRNA and/or viral proteins may also be isolated as a source of amplifiable nucleic acid for conducting the assays of the invention. Indeed, cells infected with certain viruses are commonly known to contain cell-type specific or virally encoded surface antigens, which may be used as targets for magnetic affinity capture of such cells, which may then be used as a source of target nucleic acid.

Immunomagnetically-isolated (or enriched) target virion particles are then subjected to lysis using heat or alkaline (sodium hydroxide) lysis in order to release viral RNA. Following alkaline lysis, the lysis solution is neutralized. RNAse inhibitors may be included. These method of lysing virion particles results in single stranded target viral RNA ready for conversion to cDNA using reverse transcriptase, and amplification of the cDNA using helicase-dependent isothermal amplification (see infra). All of the foregoing steps may be carried out in a single reaction chamber, an important feature of the invention which enables simplified RNA extraction without the need for heat or centrifugation. Thus, this aspect of the invention achieves the needs of POC and field applications.

Extracted nucleic acids may be purified prior to amplification. A number of column type DNA and RNA purification devices are commercially available and may be employed for this purpose. Various other techniques for purifying DNA and RNA may be employed, including without limitation, electrophoresis, gradient separation, affinity purification, etc.

Following extraction of nucleic acids from samples of interest, target sequences are then amplified using an isothermal amplification protocol. As used herein, a "target sequence" is a nucleotide sequence within a target nucleic acid molecule which is to be amplified. Within the target sequence is a primer binding portion or site, to which primers are designed to hybridize in order to initiate DNA polymerization.

The selection of a particular target sequence for amplification will relate to the assay objectives. For example, where amplification is aimed at identifying a particular strain of an organism, the target sequence should be one of the unique genetic signatures which differentiates that strain from others to which it may be related. In some cases, this may be a single defining sequence. In other cases, a combination of target sequences may be required to reliably identify and differentiate the organism. The selection of target sequences which impart specificity to assays utilizing amplified genetic material involves considerations well known in the art, including for example, unique pathogen-specific sequences, toxins genes, virulence factors or specific signature sequence combinations.

In the practice of the invention, single or multiple target sequences may be amplified in a single reaction. When multiple target sequences are to be amplified, multiple artificial amplification templates are employed, as further described infra. As is well known, sequence analysis is used to avoid possible nonspecific interactions among different oligonucleotide amplification templates and amplification primers.

The use of isothermal amplification eliminates the need for thermocycling instrumentation, technically sophisticated users, and long amplification timeframes characteristic of PCR methods. In a specific embodiment, for the detection of RNA targets, reverse transcriptase (RT) conversion of RNA to cDNA is combined with HDA, in a single reaction vessel, as further described by way of the Examples which follow.

Detailed information concerning the use of HDA to detect DNA may be found in published United States Patent Application No. 20040058378. Detailed information concerning the use of HDA, in combination with RT, in detecting RNA species may be found in published United States Patent Application No. 20060154286. A thermophilic HDA kit is commercially available (tHDA Kit, New England Biolabs, Beverly, Mass., Catalog # H0100S).

HDA amplifies target sequences using two sequence specific primers flanking the fragment to be amplified and a mixture of enzymes for DNA strand separation and polymerization. In the first step of the HDA reaction, the helicase enzyme loads on to the template and traverses along the target DNA, disrupting the hydrogen bonds linking the two strands. Exposure of the single-stranded target region by helicase allows primers to anneal. The DNA polymerase then extends the 3' ends of each primer using free deoxynucleotides (dNTPs) to produce two DNA replicates. The two replicated DNAs independently enter the next cycle of HDA, resulting in exponential amplification of the target sequence.

Helicases use energy generated by the hydrolysis of nucleoside triphosphates (for example ATP) to break the hydrogen bonds holding the strands together in duplex DNA and RNA. Helicases are involved in every aspect of nucleic acid metabolism in the cell, including DNA replication, repair, recombination, transcription, and protein translation. Helicases can be grouped into two classes based on the mechanism of unwinding: those that translocate in a 5' to 3' direction and those that travel in the opposite 3' to 5' direction. The 5' to 3' helicases usually form hexameric ring structure and are mainly involved in DNA replication.

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W.H. Freeman and Company (2.sup.nd ed. (1992)), especially chapter 11). Any helicase that translocates along DNA or RNA in a 5' to 3' direction or in the opposite 3' to 5' direction may be used to perform HDA. This includes helicases obtained from prokaryotes, viruses, archaea, and eukaryotes or recombinant forms of naturally occurring enzymes, as well as analogues or derivatives having the specified activity. Examples of naturally occurring DNA helicases, described by Kornberg and Baker in chapter 11 of their book, DNA Replication, W.H. Freeman and Company (2.sup.nd ed. (1992)), include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful in HDA include RecQ helicase (Harmon and Kowalczykowski, J. Biol. Chem. 276:232-243 (2001)), thermostable UvrD helicases from *T. tengcongensis* (published United States Patent Application No. 20040058378) and *T. thermophilus* (Collins and McCarthy, Extremophiles. 7:35-41. (2003)), thermostable DnaB helicase from *T. aquaticus* (Kaplan and Steitz, J. Biol. Chem. 274:6889-6897 (1999)), and MCM helicase from archaeal and eukaryotic organisms ((Grainge et al., Nucleic Acids Res. 31:4888-4898 (2003)).

The characterization of a thermostable helicase used in the tHDA kit (New England Biolabs) is described in An at el., 2005, J. Biol. Chem 280: 28952. The thermostable UvrD helicase is from the class of the 3' to 5' translocators. These proteins exist as monomers or dimers and, unlike many other helicases, UvrD helicase is able to melt fully duplex molecules (DNA fragment with blunt ends) and nicked circular DNA molecules. UvrD is involved in the two major DNA repair pathways: methyl-directed mismatch repair and UvrABC-mediated nucleotide excision repair. In the methyl-directed mismatch DNA repair pathway, UvrD is recruited to unwind the DNA strand containing the DNA biosynthetic error.

Polymerases utilized in carrying out HDA are selected on the basis of processivity and strand displacement activity. Subsequent to melting and hybridization with a primer, the nucleic acid is subjected to a polymerization step. A DNA polymerase is selected if the nucleic acid to be amplified is DNA. When the initial target is RNA, a reverse transcriptase is used first to copy the RNA target into a cDNA molecule and the cDNA is then further amplified in HDA by a selected DNA polymerase. The DNA polymerase acts on the target nucleic acid to extend the primers hybridized to the nucleic acid templates in the presence of four dNTPs to form primer extension products complementary to the nucleotide sequence on the nucleic acid template.

Examples of DNA polymerases suitable for carrying out HDA include an exonuclease-deficient Klenow fragment of *E. coli* DNA polymerase I, an exonuclease deficient T7 DNA polymerase (Sequenase; USB, Cleveland, Ohio), Klenow fragment of *E. coli* DNA polymerase I, Large fragment of Bst DNA polymerase, KlenTaq DNA polymerase, T5 DNA polymerase (U.S. Pat. No. 5,716,819), and Pol III DNA polymerase (U.S. Pat. No. 6,555,349). DNA polymerases possessing strand-displacement activity, such as the exonuclease-deficient Klenow fragment of *E. coli* DNA polymerase I, Bst DNA polymerase Large fragment, and Sequenase, are preferred for Helicase-Dependent Amplification. T7 polymerase is a high fidelity polymerase having an error rate of $3.5 \times 10^5$ which is significantly less than Taq polymerase (Keohavong and Thilly, Proc. Natl. Acad. Sci.

USA 86, 9253-9257 (1989)). T7 polymerase is not thermostable however and therefore is not optimal for use in amplification systems that require thermocycling. In HDA, which can be conducted isothermally, T7 Sequenase is a one of the preferred polymerases for amplification of DNA.

Mesophilic helicases show improved activity in the presence of single-strand binding proteins (SSB). In these circumstances, the choice of SSB is generally not limited to a specific protein. Examples of single strand binding proteins are T4 gene 32 protein, *E. coli* SSB, T7 gp2.5 SSB, phage phi29 SSB (Kornberg and Baker, supra (1992)) and truncated forms of the aforementioned.

In addition to salt and pH, other chemical reagents, such as denaturation reagents including urea and dimethyl-sulfoxide (DMSO) can be added to the HDA reaction to partially denature or de-stabilize the duplex DNA. HDA reactions can be compared in different concentrations of denaturation reagents with or without SSB protein. In this way, chemical compounds can be identified which increase HDA efficiency and/or substitute for SSB in single-strand (ss) DNA stabilization. Most of the biomacromolecules such as nucleic acids and proteins are designed to function and/or form their native structures in a living cell at much high concentrations than in vitro experimental conditions. Polyethylene glycol (PEG) has been used to create an artificial molecular crowding condition by excluding water and creating electrostatic interaction with solute polycations (Miyoshi, et al., 2002, Biochemistry 41:15017-15024). PEG has also been added into helicase unwinding assays to increase the efficiency of the reaction (Dong, et al., 1996, Proc. Natl. Acad. Sci. USA 93:14456-14461). PEG or other molecular crowding reagents on HDA may increase the effective concentrations of enzymes and nucleic acids in HDA reaction and thus reduce the reaction time and amount of protein concentration needed for the reaction.

Topoisomerase can be used in long HDA reactions to increase the ability of HDA to amplify long target amplicons. When a very long linear DNA duplex is separated by a helicase, the swivel (relaxing) function of a topoisomerase removes the twist and prevents over-winding (Kornberg and Baker, 1992). For example, *E. coli* topoisomerase I (Fermentas, Vilnius, Lithuania) can be used to relax negatively supercoiled DNA by introducing a nick into one DNA strand. In contrast, *E. coli* DNA gyrase (topoisomerase II) introduces a transient double-stranded break into DNA allowing DNA strands to pass through one another.

To initiate a thermophillic HDA amplification reaction such as that employed in the BioHelix tHDA kit, a primer oligonucleotide which specifically hybridizes to the target sequence is employed, as is well known. In the design of a primer for use in the invention, standard considerations of primer design apply. When comprising natural nucleotide residues, the primer oligonucleotide is generally between about 20 and 35 nucleotides in length, preferably about 25 to 27 nucleotides long, is single stranded, and is contains a sequence complementary to the target sequence, such that the primer is capable of achieving stable hybridization to the target template while minimizing the potential for secondary hybridization to non-target sites. In some embodiments, the entire primer is complementary to the target sequence, while in other embodiments, a portion of the primer contains a complementary sequence. Amplicon length for HDA is preferably between 70 and 120 nucleotides. Amplicons containing a G+C content of approximately 40% are preferable. Primer Tm is preferably 60° C.-80° C., and more preferably 68-72° C.

As is known, primers should be designed to achieve stable and specific hybridization to the target sequence while avoiding the possibility of inter-primer hybridization, which may result in the formation of primer dimers or primer oligomers. Also, the potential formation of secondary structures within a primer should be minimized. Palindromic sequences, therefore, should generally be avoided as these sequences tend to form stable secondary structures which preclude stable hybridization to the template strand. Typically, stretches of identical bases should also be avoided. With respect to the template, primers should be selected for their ability to stably hybridize to the target region of the template, and thus selection of a suitable target region to which an acceptable primer may be designed should be taken into consideration. In this regard, generally, primers should not be designed to anneal to regions of secondary structure within the target sequence having a higher melting point than the primer.

Methods and tools for the design and synthesis of oligonucleotide primers are well known in the art. For example, various software tools are widely available to assist in the design of primers optimized for a particular set of circumstances, including for example, Primer Express™ software (Applied Biosystems, Foster City, Calif.), Primer3 (Whitehead Institute, Cambridge, Mass.), and Consed (David Gordon, Univ. Washington). Typical "primer picking" programs permit variable length and Tm parameters, and assist in avoiding the design of primers with palindromic sequences or other potential secondary structure problems, primers with complementarity to non-target regions of the template, etc.

Presented in Example 7, infra, is a step-wise approach for generating compatible sets of amplification primers, detection oligonucleotides and capture oligonucleotides for detecting various influenza A target nucleic acid sequences using the methods of the invention.

In a particular aspect of the invention, fork-generating primers are provided for increasing helicase loading to double-stranded DNA substrates. More specifically, primers containing a target-specific sequence and a 5' poly dA or poly dT sequence of between 5 and 40 bases in length are used to create a low melting temperature region in amplified DNA duplexes. In preferred embodiments, poly dT or dA sequences are 5 to 20 bases in length. The inclusion of poly dT or poly dA sequences results in localized melting of the A-T double strand in amplified ds DNA at the HDA reaction temperature (i.e., 60° C.), thereby generating a symmetrical "fork" secondary structure. The fork secondary structure, applicants have discovered, presents an ideal substrate for helicase loading, resulting in improved HDA efficiency and faster reaction times. These primers also enable the use of variable reverse transcriptase enzymes, including polymerases with RT activities. See Example 5, infra.

In performing an RT-HDA reaction, an enzyme which can digest the RNA portion of an RNA/cDNA duplex is employed in the reaction mixture. RNase H is an endoribonuclease that specifically hydrolyzes the phosphodiester bonds of RNA hybridized to DNA, but does not digest single or double-stranded RNA. Members of the RNase H family can be found in nearly all organisms, from archaea and prokaryote to eukaryota. RNase H cloned from *E. coli* may be obtained from commercial sources (i.e., New England Biolabs). RNase H activity is often associated with many naturally occurring reverse transcriptases. The RNase H activity may be provided by a separate enzyme, such as *E. coli* RNase H, or by an RNA-dependent DNA polymerase (i.e., reverse transcriptase). In one embodiment, RNase H (Ribonuclease H) is employed for this purpose. In combination with a high temperature RT-HDA reaction, a thermostable RNase H is used, such as Hybridase (EPICENTRE, Madison, Wis., USA). The use of RNase H in the RT-HDA reaction achieves the objective of producing single stranded template for subsequent amplification, whereby the helicase in the HDA reaction achieves the unwinding of polymerized DNA duplexes for exponential amplification.

Following amplification, a solution containing a DNA amplification product is assayed for the presence of the target nucleic acid using a lateral-flow chromatographic device which comprises a combination of capture and detection oligonucleotides complementary to specific targets in the amplified DNA.

The lateral flow chromatographic devices employed in the nucleic acid detection system of the invention is similar to devices in use for protein diagnostics such as home pregnancy kits. Briefly, the device is composed of a series of absorbent substrates which are used to transport DNA in a lateral manner to components containing certain reagents or materials required for the detection of amplified DNA (see schematic illustration in FIG. 2).

In a simplified illustration, one embodiment of the lateral flow device is structurally organized into at least 3 zones, comprising in linear orientation: (a) a sample pad or "sample receiving zone" constructed from absorbent material onto which a liquid, nucleic acid-containing sample is deposited (i.e., solution containing the labeled DNA amplification product), (b) a conjugate release pad or "labeling zone" containing a least one oligonucleotide-fitted label such as a detectable particle (e.g., microsphere, bead, quantum dot), and (c) a capture zone comprising a microporous membrane, such as a nitrocellulose or nylon membrane, containing at least one immobilized capture oligonucleotide. In preferred embodiments, a fourth element comprises an absorbent material which is capable of facilitating the lateral flow of the liquid sample from the sample pad end of the device to and through the detection zone. In alternative embodiments, the conjugate release pad element is eliminated, and the amplified DNA sample to be assayed for the presence of a target nucleic acid is mixed with the labeled detection oligonucleotide prior to placing the sample onto the sample pad.

The first substrate, or sample pad, comprises an absorbent material preferably composed of a matrix, with minimal nucleic acid binding properties, that will permit unobstructed migration of the nucleic acid analyte to subsequent stages of the apparatus without depletion. In a specific embodiment, the sample pad is composed of a cellulose fiber pad such as Millipore cellulose fiber sample pad material (Cat# CFSP223000).

The sample pad is situated within the device such that it is in physical contact with the conjugate release pad, a matrix composed of a material with minimal nucleic acid binding capacity and of a physical composition which allows dried detection particles to be liberated into solution with minimal residual binding to the matrix. Examples of such material are Millipore glass fiber conjugate pad (cat# GFCP203000) and Schleicher & Schuell Accuflow P polyester reagent release media. The Accuflow P substrate is a particularly suitable reagent release material for dyed microsphere-based detection. The sample pad may be laminated to the conjugate release pad such that the two matrices are in physical contact with a 1-2 mm overlap. The conjugate release pad in turn is laminated to the microporous membrane, which contains the capture zone, such that it overlaps and physically contacts the proximal region of the microporous membrane by 1-2 mm. In one embodiment, the microporous membrane is situated such that it is in physical contact with an absorbent pad at the distal end to facilitate sample transport through the microporous membrane should the sample volume exceed the wicking capacity of the microporous membrane itself.

In one embodiment, the microporous membrane is composed of a supported nitrocellulose membrane of sufficiently large pore structure to allow the unimpeded transport of detection reagent through the membrane matrix. Examples of suitable nitrocellulose materials for dyed microsphere mediated detection are Millipore HiFlow Plus HF09004, HF13504, Schleicher & Schuell Prima 60, Schleicher & Schuell Prima 85. The Millipore HF13504 nitrocellulose membrane has been demonstrated to provide rapid, specific and sensitive detection when patterned with appropriate detection oligonucleotides.

Microporous membranes are patterned with positive and negative control reagents and capture reagents in an array such that the physical position of each reagent is known. Positive control reagents may, for example, be composed of oligonucleotides complementary to detection oligonucleotides. For example, the use of an oligonucleotide complementary to the labeled detection oligonucleotide as a positive control allows direct hybridization of the detection oligonucleotide/label complex following lateral flow chromatography over the positive control. Negative controls for hybridization specificity can be incorporated into the device as is well known.

Capture oligonucleotides are composed of oligonucleotides synthesized such that the sequence is complementary to a region of the analyte target nucleic acid not overlapping with the region complementary to the detection oligonucleotide. Ideally, the predicted secondary structure of the analyte target nucleic acid is examined to identify those regions exhibiting reduced likelihood of participating in intramolecular hydrogen bonds. Such regions are preferable sites for detection and capture oligonucleotide binding (see, supra).

Negative and positive control reagents as well as capture reagents are patterned on to the detection membrane using any of a number of deposition techniques. Capture elements may take the form of lines, stripes, dots or human readable icons, letters or other forms or shapes deemed useful to the interpretation of device read-out.

The lateral flow device is enabled by the use of two classes of oligonucleotide referred to here as capture and detection oligonucleotides. The detection oligonucleotide is linked by any of a number of means to a label or detection reagent that, when concentrated by capture through hybridization, renders the capture zone optically distinguishable from the surrounding substrate and from additional capture zones where the detection reagent has not been sequestered. Examples of detection particles which provide an easily detectable signal include dyed microspheres (i.e., polystyrene microspheres), colloidal gold, nano-gold, fluorescent nanoparticles (e.g. Qdots™, QuantumDots, Inc.). In specific embodiments exemplified in the Examples, infra, carboxyl-polystyrene microspheres embedded with colorimetric dyes are utilized. The detection oligonucleotide is designed such that the melting temperature of the resulting oligonucleotide allows hybridization to its cognate sequence on the analyte under ambient conditions with sufficient rapidity to allow duplex formation to occur during lateral flow. Detection oligonucleotides with Tm of 50-70° C. have been shown to provide effective reagents for the detection of relevant analytes (using approximately 20-mer oligonucleotides).

Detection oligonucleotides are synthesized with suitable modifications to allow the efficient linkage to appropriate detection reagent. In some embodiments it is advantageous to include a spacer sequence consisting of 9 to 15 T residues proximal to the modified end of the oligonucleotide that will be coupled to the detection reagent. Chemistries of known suitability for use in the device include biotin/streptavidin through a biotin incorporated onto either the 5' or 3' end of the detection oligonucleotide and covalent cross-linking through a primary amine incorporated into either the 3' of 5' end of the detection oligonucleotide. Other methods that mediate the formation of a stable complex between the detection reagent and the detection oligonucleotide under assay conditions should also be suitable for use in the fabrication of the device.

The second class of oligonucleotide used in the device is the capture oligonucleotide. This reagent is immobilized on the microporous membrane, which is typically a nitrocellulose or nylon membrane, through the use of standard methods, including without limitation drying followed by ultraviolet light cross-linking using 0.5 Joules UV. The capture oligonucleotide is preferably designed such that the sequence is complementary to the analyte target nucleic acid at a region predicted to have little or no secondary structure. The length of the capture oligonucleotide is typically approximately 20 to 30 bases in length. In some embodiments it is advantageous to include a spacer sequence consisting of 9 to 15 T residues. Several pairs of detection and capture oligonucleotides useful in the detection of influenza A target sequences derived from seven of the eight influenza A genes are provided in the Examples, infra.

Detection and capture oligonucleotides can be synthesized using well known DNA synthesis chemistries. The incorporation of modified nucleic acids such as PNA (peptide nucleic acid) or LNA (locked nucleic acid) may be useful for the enhanced hybridization properties of these DNA derivatives. The use of PNA or LNA moieties in the preparation of detection and/or capture oligonucleotides will be useful in manipulating the desired melting temperature, and so may allow shorter oligonucleotides to be employed for detection and/or capture where sequence constraints preclude longer DNA oligonucleotides. Exemplary pairs of detection and capture oligonucleotides used in detecting various influenza A target sequences are presented in Example 6, infra.

The lateral flow chromatographic device used in the practice of the methods of the invention can make use of diverse detection modalities, including visual detection signals resulting from the capture and increased local concentration of an appropriate detection particle or other label. When colorimetric detection particles, such as dyed polystyrene microspheres, are used, the resulting colorimetric signal can be visualized by eye. Alternatively, for more quantitative and sensitive detection of signal, an electronic instrument capable of detecting colorimetric signals may be employed. Such instruments include standard flatbed scanners, dedicated lateral flow chromatographic strip readers (e.g. QuadScan, KGW Enterprises, Inc), or a simple CCD based devices fabricated for the detection of colorimetric signals such as those employed by commercially available immunochromatographic test strips (e.g. Clearblue Easy Digital Pregnancy Test).

Visualization by eye can be aided by the fabrication of the device in a manner that generates an easily recognized or interpreted shape on the dipstick surface. One example would be the patterning of a dipstick microarray with elements in a physical configuration that results in the appearance of a letter or symbol indicative of a positive or negative result (e.g. a "+" or "−" symbol).

Embodiments that employ fluorescent detection reagents such as fluorescent nanoparticles (e.g. Qdots, QuantumDots, Inc.) offer the potential increased sensitivity that results from the application of fluorescence detection technology. Such embodiments can be read using any of a number of ultraviolet light sources including hand held UV lamps, UV emitting LEDs, and light sources with sufficient emission in the UV to excite the nanoparticles. A simple filter can be used to enhance the visualization of nanoparticle fluorescence emissions. For example, a long pass filter with a cut off below the emission wavelength of the nanoparticle may be employed. In the case of excitation with a white light source, an additional filter to limit excitation to UVA and shorter wavelengths can be used (e.g., a 380 nm short pass filter).

The microporous membrane of the lateral flow chromatographic device may contain capture oligonucleotides printed monolithically in order to produce virtually any colorimetric pattern that can be visualized by the unaided human eye, such as bands, letters, numbers, symbols, and the like. If the sample contains both the first and second target sequences, colored beads with hybridized detection oligonucleotide-target nucleic acid will then hybridize to the immobilized capture oligonucleotide, and thereafter remain stably immobilized to the membrane at that physical location. Such "low density" components of the detection zone may be used to provide a rapid indication of the presence of a target sequence or sequences in the sample, visualized only be the unaided eye.

In addition, the detection zone may contain one or more "high density" components, capable of providing high resolution detail of the signatures of the sequences present in the sample nucleic acid. For example, an array of a number of distinct second detection oligonucleotides may be deposited in distinct physical locations on the membrane (i.e., an array of spots), each of which detection oligonucleotide is specifically complementary to a distinct target sequence. Such high-density arrays may be used to interrogate the sample for genotype signature sequences and the like. These array components may be read by methods well known in the art, including by scanning and computer assisted densitometry, the use of CCD cameras, etc.

Assay devices of the invention comprising such low and high density detection zones are termed "dual-density" systems, assays and devices. The principal design element of such dual-density devices is the provision of two levels of information obtained from a single sample. The low density component provides instantaneous visual information indicative of the presence or absence of a first level target sequence, and may be used to provide fundamental diagnostic information, such as the presence of a nucleic acid sequence indicative of a virus or bacteria in the sample. Because this information is provided by a colored band or other shape or symbol, the user is able to identify the presence of a target immediately and without the use of any instrumentation whatsoever.

The high density components may be assayed using standard instrumentation at any time following the assay. For example, the device may be stored or shipped for high density array analysis using appropriate instrumentation and/or expertise. Thus, as an example, such dual-density devices may be used by a consumer patient for determining whether a body fluid sample contains an influenza virus. A positive result indicates the need for having the high density component of the device analyzed by specialized personnel, in order to determine the influenza strain, subtype, or genotype, for example. The consumer patient is able to use the device to determine the need for profession medical attention. The medical professional is able to analyze the same device for more specific diagnostic information.

The lateral flow chromatographic device is designed to be useful for the detection of analyte target sequences amplified from samples containing target nucleic acids. Typically, the analytes are amplified, single-stranded DNAs corresponding to the target sequences. If the DNA amplification product is not rendered single-stranded before application to the device, heat may be used within the device to denature double stranded DNAs. In some embodiments, the amplified DNA is contacted with the detection olignucleotide(s) during the HAD reaction, thereby obviating the need for a separate denaturing step.

In one embodiment, a solution containing one or more target sequences to be detected by the device is introduced to the sample receiving zone of the device. This may be achieved by dipping the sample receiving zone end into the solution, or by dropping a quantity of the solution onto the sample receiving zone of the lateral flow device. The device is sufficiently robust that the composition of the buffer solution carrying the DNA amplification product is not critical, however, several practical considerations are taken into account to assure compatibility of the buffer with the device. Most significantly, the ionic strength of the sample buffer must be such that precipitation or aggregation of the detection particles does not occur. Similarly, sufficient ionic strength of the buffer is required to support hybridization during lateral flow. Impregnation of the sample pad and/or conjugate release pad with Triton-X100, SDS, BSA, ficol, and/or polyvinyl pyrolidone, or introduction of these components to the sample buffer itself, can stabilize the detection particles and block non-specific interactions between the detection particles and the detection membrane. While a range of concentrations of these reagents can be used successfully, buffers of proven efficacy include 0.1% ficol, 0.1% BSA, 1% Triton X-100, and 150 mM NaCl. This particular buffer supports mono-disperse detection particle suspensions. In one embodiment (see Example 1, infra), a buffer containing 0.75×SSC, 0.1% Ficoll, 0.1% Gelatin, 1% triton X-100 and 20 mM $Na_2PO_4$ gave the best signal with minimal background, and the combination of Hi-Flow Plus membrane 90 and 0.39 um microspheres providing optimal sensitivity and reasonable detection speed (~5 minutes).

Once on the sample pad, the analyte solution flows from the proximal (sample) end towards the distal (detection) end of the device. In one embodiment, detection oligonucleotide-functionalized dyed microbeads are embedded into the conjugate release pad component of the device, preferably in lyophilized form, ready to be rehydrated as the analyte solution travels into this area of the device. As the analyte solution moves across the conjugate release pad, the microbeads are rehydrated and are available for detection oligonucleotide hybridization to target sequences within the sample. Target sequences, when present, will become hybridized to the detection oligonucleotide and thus to the beads. This complex continues lateral flow migration to the detection membrane, where immobilized capture oligonucleotides hybridize to the target sequence, thus capturing the target sequence-bead complex. See FIG. 3 illustration.

The system of the invention and its components are further described by way of the following examples, none of which are intended to be limiting.

EXAMPLES

Example 1

Amplification and Detection of Bacillus Target DNA Using HDA and Lateral Flow Capture This example evaluates the performance of HDA in combination with the lateral flow detection platform of the invention, using Bacillus anthracis (Ba) as a model target, and demonstrates the feasibility, sensitivity and specificity of these component of the detection system of the invention applied to bacterial DNA targets.

Materials and Methods:

Conjugation of Labeling/Detecting Oligonucleotide Probes onto Dyed Microspheres:

Carboxyl-polystyrene microspheres embedded with blue dyes, with diameters from 0.08-0.39 µM, were purchased from Spherotech Inc. (Libertyville, Ill.). To label/detect target sequence (amplification product or synthetic target template oligomer), specific labeling/detecting probes carrying an amine modification group at their 5' end (complementary to the target sequence) were covalently conjugated to the carboxylated microspheres using a standard EDAC (1-ethyl-3-(3-dimethylaminopropyl) carbodiimide hydrochloride) crosslinking reaction. The gene-specific labeling/detecting oligonucleotides used for covalent coupling contained four components: (1) a 5' amine modification for amide coupling to the carboxyl-polystyrene microspheres; (2) a 12 carbon spacer to extend the oligonucleotide from the microspheres to increase the accessibility of oligonucleotide to its hybridization target; (3) an 12mer poly(dT) linker to further increase the freedom of probe for better hybridization efficiency; and (4) a 20-23 base hybridization sequence complementary to the 5' end of targets (e.g., Ba pag, protective antigen, or cap, capsid gene).

Amine-modified oligonucleotides were synthesized by Integrated DNA Technology Inc. (Coralville, Iowa). Before the conjugation reaction, a desalting process was performed by suspending the oligonucleotides in Milli-Q® water with the final concentration of 100 µM. Then the oligonucleotides were injected into a Slide-A-Lyzer 10K (PIERCE, Rockford, Ill.). The Slide-A-Lyzer containing oligonucleotide inside was placed into a beaker with milli-Q water for dialysis for 4 hours with stirring continuously at room temperature. After dialysis, 1.0M pH5.0 2-(N-morpholino) ethanesulfonic acid (MES; Sigma, St. Louis, Mo.) was added in to adjust the final concentration to 0.1M. The incubation continued by stirring overnight at room temperature. Conjugation of the desalted oligonucleotides to microspheres was carried out by mixing 40 µl Carboxyl-polystyrene blue microspheres at 5.0% (W/V) with 400 µl of 10 µM oligonucleotides followed by brief sonication (1 minute with output setting of 7) on a Sonifier Cell Disruptor 200 (Branson Ultrasonics Corporation, Danbury Conn.). Then, the conjugation reaction was initiated by adding ~3 mg EDAC (Invitrogen, Carlsbad, Calif.) to the microsphere/oligo mixture, followed by one hour incubation at room temperature on a multi-purpose rotator (Model 151, Bohemia, N.Y.). 4 µl of 20% SDS solution was then added to prevent microsphere aggregation. The unbound excess oligonucleotides were removed from the microspheres by a brief centrifugation at 7000 rpm (Eppendorf® 5415C, Eppendorf, Westbury, N.Y.) and discarding the supernatant. The trace amount of residual oligonucleotides were removed by two more subsequent washes with 0.1% SDS. Finally, the microspheres were resuspended in 400 µl of 0.1% SDS for storage.

Assembly of Nucleic Acid Lateral Flow Assay Strip:

Nitrocellulose membrane cards with clear polyester material backing, conjugation and absorption pads were purchased from MILLIPORE Corp, MA. Hi-Flow Plus membranes with lateral-flow rates of 65, 75, 90, 120, 135, 180, and 240 seconds across 4 centimeters of membrane were purchased to evaluate the optimal detection condition. As depicted in FIG. 1, lateral flow assay strip was assembled under the manufacture's instruction with the three parts: (1) sample pad (AP22) (20 mm×300 mm, B3HN43393); (2) hiflow plus membrane cards (type 6 cm×30 cm, SHF0900225 for HF090 or other membrane card with a different flow rate), and (3) absorbent pad (AP22) (17 mm×300 mm, B4JN49233). The ends of three parts were overlapped in order to ensure continuous flow of the hybridization reaction from the sample pad to the absorbent pad. In this example, four different gene capture probes were spotted on the membrane (see Table 1, below).

Immobilization of Capture Probes onto the Membrane by UV Crosslinking:

Capture oligonucleotides were synthesized with a 12mer poly (dT) linker at 3' ends and a 20-23 mer hybridization sequence complementary to the 3' end of target sequence (see Table 1). Capture probes of 0.2 µl at 200 µM were spotted onto nitrocellulose membrane strips using a P2 micropipetter onto preassembled strips. After drying at room temperature for 10 minutes, the strip was UV cross linked at 5000 µJulesx100 (UV Stratalinker 2400, Stratagene, La Jolla, Calif.).

NA Assay Detection of Synthetic Target Sequences and Isothermal Amplification Products:

A hybridization mixture of 400 µl containing 2× hybridization buffer, 10 µl labeled microspheres, and 2 µl synthetic target sequences or 30 µl denatured HDA amplicons were applied to the sample pad. The mixture migrated along the membrane strip through capillary action. Upon passing the capture spot immobilized with capture probes, a sandwich complex was formed among labeling/detecting probe, target sequence, and capture probe resulting in signals that can be visualized by eye or imaging. The images scanned by Epson 2580 Photo Perfection scanner were processed by Adobe® PhotoShop® image analysis software. The visual detection of target sequence ranged from 2 minutes to 30 minutes depending on the particular membrane, microspheres and concentration of target sequence. The typical assay used for the detection of the HDA amplification product was ~5 minutes.

Synthetic Target Sequences:

The synthetic target sequences used for optimization and positive controls were synthesized and purified by Integrated DNA Technology Inc. (see Table 1).

*Bacillus anthracis* (Ba) Genomic DNA Samples:

Genomic Ba DNA was provided by Dr. Richard A. Robison at Brigham Young University. The cell culture and genomic DNA purification was carried out in Dr. Robison's BSL-3 laboratory using standard protocols. The DNA concentration was quantified by standard UV absorption.

Helicase-Dependent DNA Amplification (HDA):

HDA reactions were conducted using the IsoAmp® tHDA kit (New England Biolabs, Inc. Ipswich, Mass.) according to the manufacturer's instructions.

Primers for HDA:

Specific primers to amplify Ba virulence genes pag and cap were designed using Oligo 6 primer analysis software (Molecular Biology Insights, Inc., Cascade, Colo.) (see Table 1) with high-stringency parameters and sequence BLAST analysis to reduce non-specific amplification in HDA. The reverse primers were labeled with biotin at the 5' end and HPLC purified. The primers were synthesized at Integrated DNA Technologies (IDT, Coralville, Iowa) and dissolved in 1×TE (10 mM Tris-HCl, 1 mM EDTA, pH 8.0). The primer pairs generated amplicons with 93 bp in length for pag and 103 bp for cap, respectively. The amplicons were confirmed by 8% acrylamide gel electrophoresis and assay detection.

Single-Plex HDA Reactions:

HDA reactions (25 µl) containing 10× annealing buffer, 200 nM each primer and amount of Ba genomic DNA were denatured for 2 minutes at 95° C. and promptly put on ice, followed by addition of 25.0 µl 2× tHDA master mix. The amplification reaction was continually incubated at 65° C. for 75 minutes and then subjected to a thermal (94 degree for 1 minute) or enzymatic denaturation step (e.g. 1 µl exonuclease λ for 20 minutes at room temperature) before application to the lateral flow assay.

Multiplexed HDA Amplification:

HDA was performed exactly as above, except two amplification primer pairs were added in the reaction. For further investigation of the amplification efficiency and specificity of HDA, HDA amplification of pag from Ba genomic DNA in excess of the environmental near neighbor *Bacillus thuringiensis* (Bt) genomic DNA at varying concentrations was performed.

TABLE 1

OLIGONUCLEOTIDES USED IN EXAMPLE 1

| | HDA amplification primers |
|---|---|
| Forward: HDAPagPF | 5'-CAGAAGTGCATGCGTCGTTCTTTG-3' [SEQ ID NO: 1] |
| Reverse: HDAPagPR | 5'-Biotin/AGTGAATGATCAATTGCGACCGTACTT-3' [SEQ ID NO: 2] |
| Forward: CapHDAP1F | 5'-TACATGGTCTTCCCAGATAATGCATCGCTTG-3' [SEQ ID NO: 3] |
| Reverse: CapHDAP2R | 5'-Biotin/CCGGATGAGCATTCAACATACCACGG-3' [SEQ ID NO: 4] |
| | Oligonucleotides for microsphere conjugation |
| Bead/HDAPag1 | 5'-$NH_2C_{12}$/TTTTTTTTTTTT/ATATTGGTGGGAGTGTATCT-3' [SEQ ID NO: 5] |
| Bead/HDACapCap2 | 5'-$NH_2C_{12}$/TTTTTTTTTTTT/CTTTAGCGGTAGCAGAGGCTCTT-3' [SEQ ID NO: 6] |
| | Oligonucleotides for membrane immobilization |
| Pag capture probe: | 5'-GCAGGATTTAGTAATCGAATTT/TTTTTTTTTTTT-3' [SEQ ID NO: 7] |
| Cap capture probe: | 5'-GGGATTGATGAGGAAACAGCATT/TTTTTTTTTTTT-3' [SEQ ID NO: 8] |
| Neg ctrl capture probe 1 (CapB) | 5'-TACATGGTCTTCCCAGATAA/TTTTTTTTTTTTTT-3' [SEQ ID NO 9] |
| Neg ctrl capture probe 2 (Cya) | 5'-TGCTAGAGAATTAAATACATATA/TTTTTTTTTTTTTT-3' [SEQ ID NO: 10] |
| Neg ctrl capture probe 3 (Flu) | 5'-GTGCCTTGAGAC/TTTTTTTTTTTTTTT-3' [SEQ ID NO: 11] |

TABLE 1-continued

OLIGONUCLEOTIDES USED IN EXAMPLE 1

| | |
|---|---|
| Pos ctrl capture probe 1 (Pag) | 5'-TTCGAATTACTAAATCCTGCAGATACACTCCCACCAATAT-3' [SEQ ID NO: 12] |
| Pos ctrl capture probe 2 (Cap) | 5'-GAATGCTGTTTCCTCATCAATCCCAAGAGCCTCTGCTACCGCTAAAG-3' [SEQ ID NO: 13] |

Synthetic target sequences for assay characterization

| | |
|---|---|
| Pag target sequence (FIG. 1) | 5'-TTCGAATTACTAAATCCTGCAGATACACTCCCACCAATAT-3' [SEQ ID NO: 14] |
| Cap target sequence (FIG. 4) | 5'-GAATGCTGTTTCCTCATCAATCCCAAGAGCCTCTGCTACCGCTAAAG-3' [SEQ ID NO: 15] |

Figure 4:
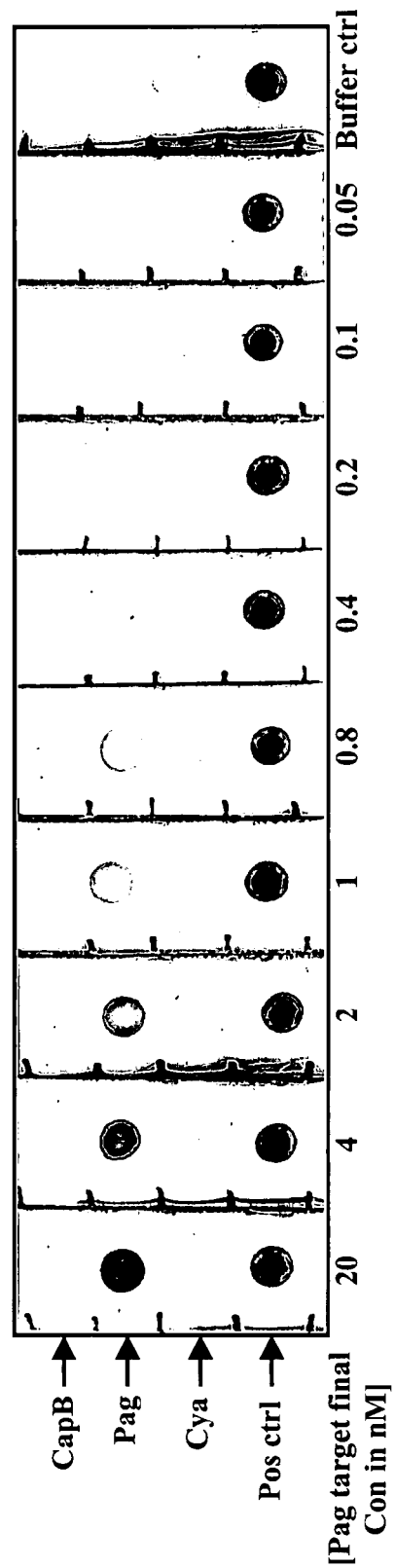
FIG. 4. Detection sensitivity of the assay described in Example 1 on synthetic Pag target sequence. Each assay was imprinted with four different gene capture probes, Cap B, Pag, Cya and Positive control sequence (complementary to the pag labeling/detection probe of the dyed microspheres). Hybridization reaction mix containing varying concentration of Pag target (from 0 to 20 nM final concentration, from right to left) and pag labeling/detecting probe tagged blue microspheres in 1× hybridization buffer was applied on individual assay, respectively (as described in Materials and Methods of Example 1).

Results:
Optimization of Lateral Flow Detection Assay:

Different membrane and microsphere components were tested for their sensitivity using the same synthetic model sequence Pag target sequence (see Table1, with bead/HDAPag1 labeling/detecting probe and Pag capture probe) under several commonly used hybridization buffer conditions. Results indicated that buffer containing 0.75×SSC, 0.1% Ficoll, 0.1% Gelatin, 1% triton X-100 and 20 mM $Na_2PO_4$ gave the best signal with minimal background, and the combination of Hi-Flow® Plus membrane 90 and 0.39 um microspheres providing optimal sensitivity and reasonable detection speed (~5 minutes). Under these optimal hybridization conditions, the sensitivity of detection was measured by applying hybridization reaction: mix containing varying concentrations of Pag target to assay. As shown in FIG. 4, as little as 20 fmoles of Pag target (0.1 nM, 200 µl) can be detected using the NA assay, achieving comparable sensitivity offered by a typical homogeneous fluorescence assay (e.g. Taqman assay). As shown in FIG. 4, there was no visible signal detected on the spots immobilized with CapB and Cya capture probes indicating the lack of false positives.

Figure 8:
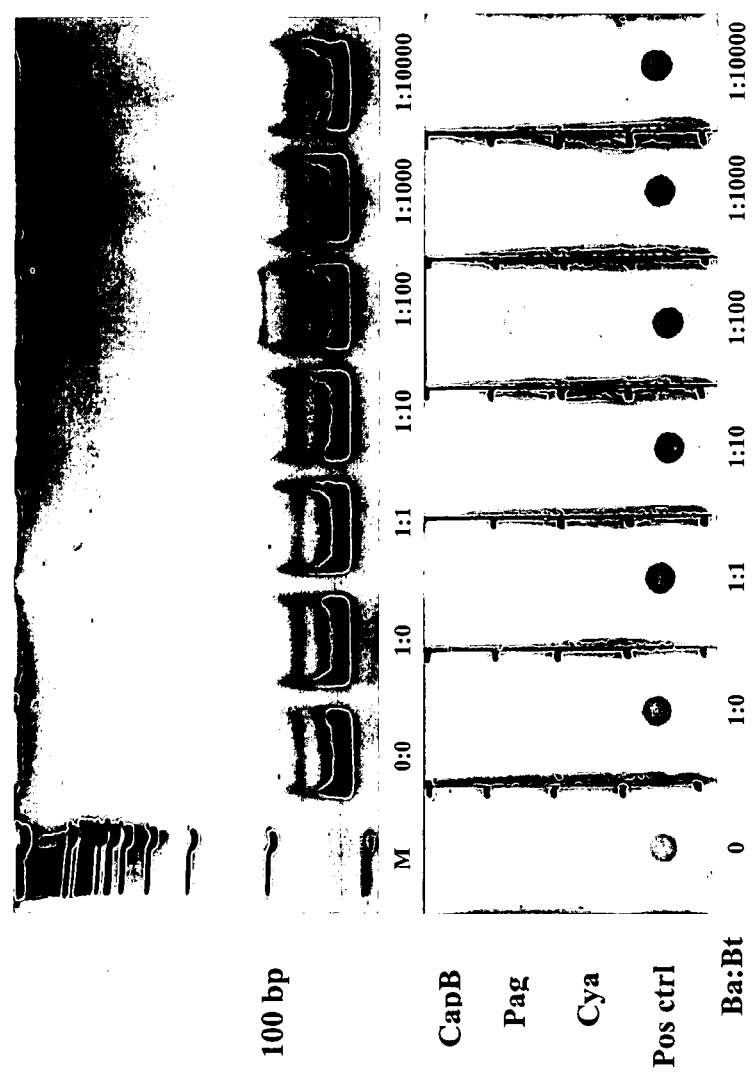
FIG. 8. Detection of rare target copies from highly heterogeneous sample mixture. In each mixture, the copy number of Ba genomic DNA was 100, while that of Bt genomic DNA was 0, 100, 1000, 10000, 100000 and 1000000 times of excess of the target DNA. Amplification target (30 µl) was denatured and was analyzed either by gel or assay detection. See Example 1.
Figure 9:
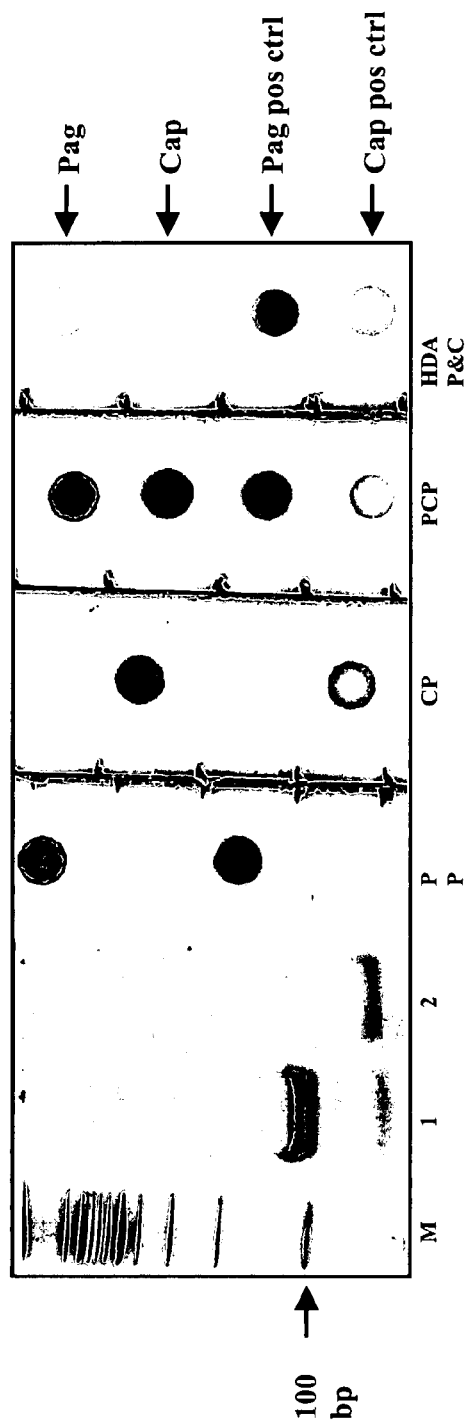
FIG. 9. Multiplexed amplification products analyzed by gel and NA assay. From Left, M: 100 bp DNA ladder (Promega); 1: multiplex HDA product; 2: HDA negative control; PP: Assay positive control for pag; CP: Assay positive control for cap; PCP: Assay positive control for pag and cap (by mixing Pag and Cap synthetic target sequences); HDA P&C: Assay test of HDA product of lane 1. See Example 1.

NA Assay Detection of Isothermal Amplification Products:

To further evaluate the utility of the NA assay on the direct detection of the crude amplification products, two HDA amplifications that generate amplicons with the sizes of 93 bp or 103 bp fragments for pag or cap, respectively, were conducted. The amplicons were divided into two aliquots with one aliquot applied to 8% nondenaturing acrylamide gel electrophoresis (left panels, FIG. 5) and the other aliquot applied to the NA assay (right panels, FIG. 8).

Figure 5:
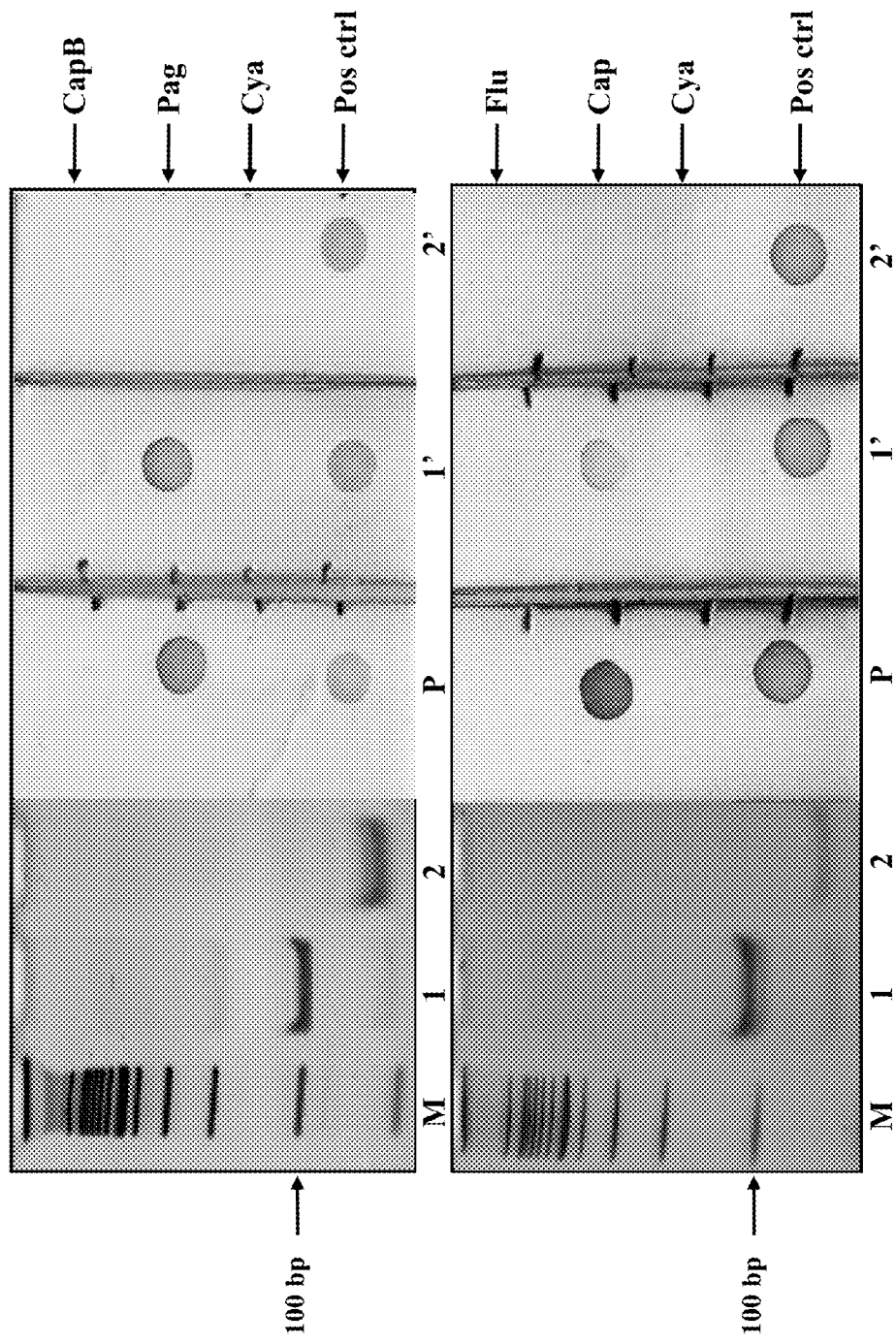
FIG. 5. Detection of Ba HDA isothermal amplification products using 8% nondenaturing acrylamide gel electrophoresis and assay described in Example 1. For each assay detection set, four capture probes were immobilized on the membranes, CapB, Pag, Cya and Pag positive control for Top panel, and Flu, Cap, Cya and Cap positive control for the bottom panel. Top panel for pag and bottom, panel for cap, respectively. In left gel image panels: M: 100 bp DNA ladder (Promega); Lane 1: HDA amplicon of pag or cap, respectively; Lane 2: HDA no-template negative control. Right assay image panels: P: A positive amplification control (using synthetic Pag and Cap target sequences); Lane 1', Assay detection of HDA amplicons of pag or cap, respectively; Lane 2', Assay detection of HDA no-template negative controls.

As shown in FIG. 5, the NA assay provided clear visible signals within 2 minutes (Lane 1's for pag and cap detection, right panel) as agreed by parallel gel electrophoresis results (Lane 1s, Left panel). In addition, no non-specific signals were observed in negative controls and other non-target spots (Lane 2 and 2's in FIG. 5) without further purification requirements.

Figure 6:
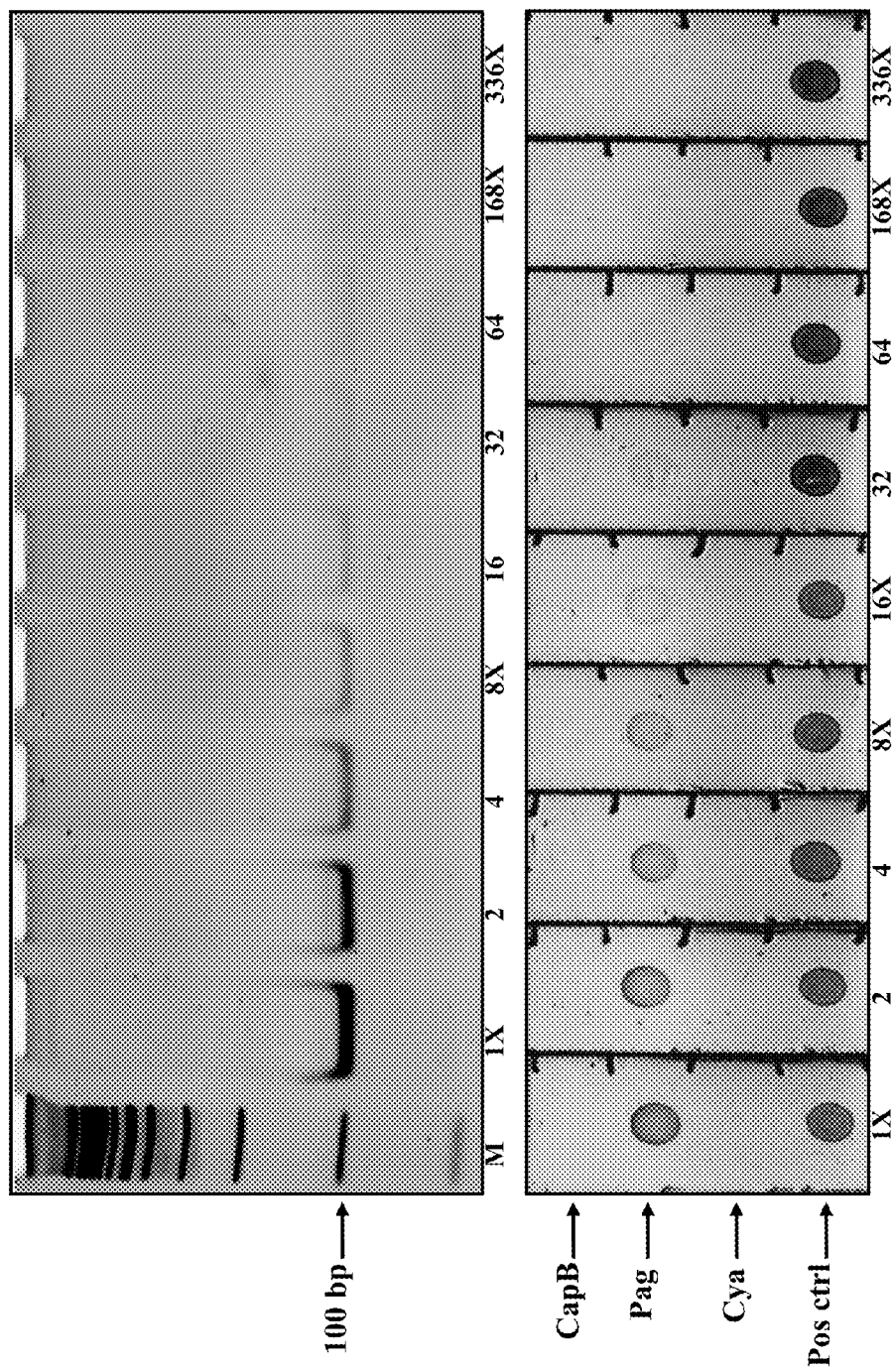
FIG. 6. Side-by-side comparison of gel electrophoresis-based and NA assay-based detection of pag amplification products. A serial dilution of Ba pag amplicon containing 200 (1×), 100 (2×), 50 (4×), 25 (8×), 12.5 (16×), 6.3 (32×), 3.2 (64×), 1.6 (128×), 0.8 (256×) ng final products was prepared using the procedure described in Materials and Methods of Example 1. Top panel: Image of 8% nondenaturing acrylamide gel electrophoresis of pag amplification product followed by Ethidium Bromide staining and UV image analysis. Bottom panel: NA assay detection of pag amplification products.
Figure 7:
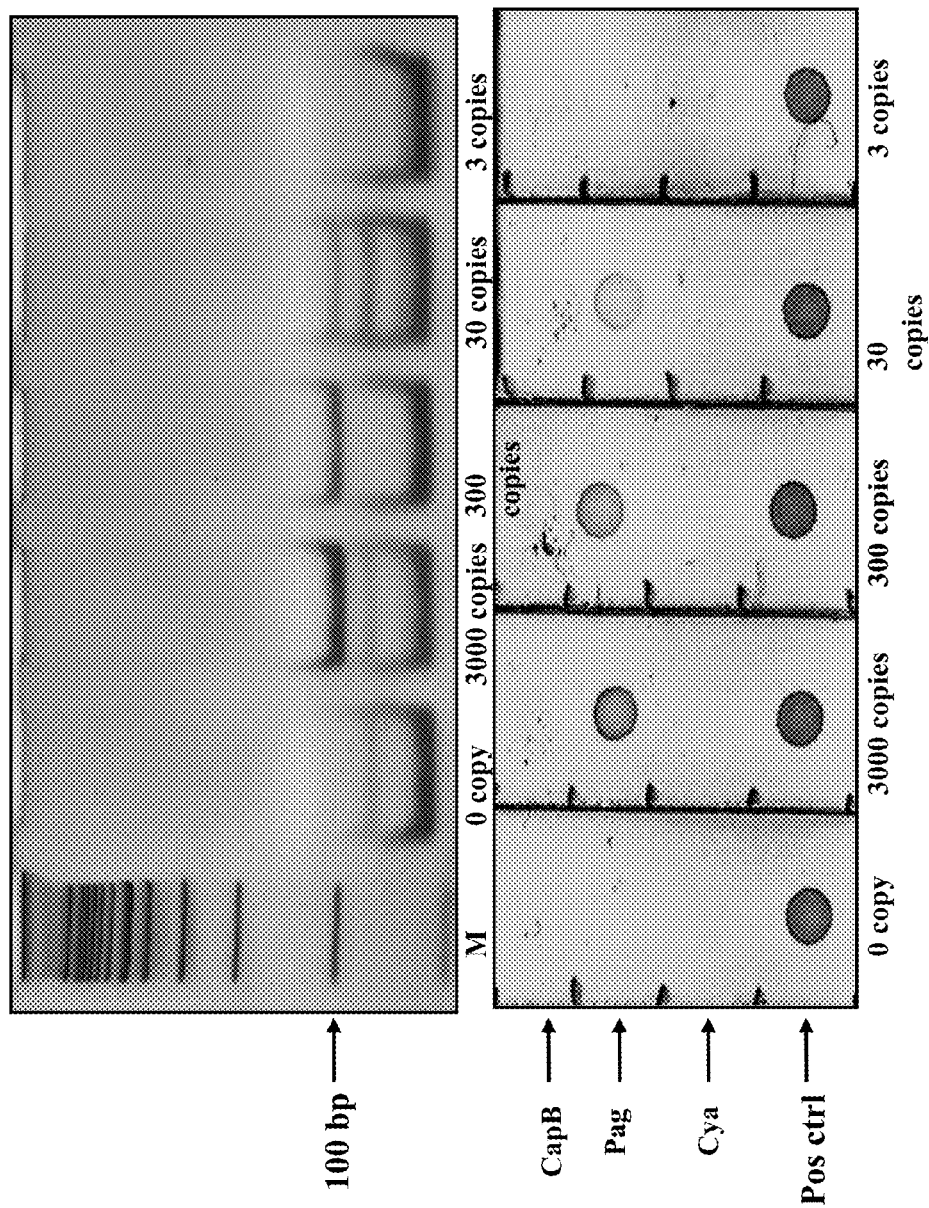
FIG. 7. Sensitivity assessment of HDA amplification and subsequent NA assay detection. Gel electrophoresis (Top panel) and assay detection (Bottom panel) of HDA amplicons amplified from varying starting copies of Ba genomic DNA target. See Example 1.

A side-by-side comparison to demonstrate the relative sensitivity of the NA assay vs. nondenaturing acrylamide gel electrophoresis detection on Ba pag HDA amplicons was also performed. For this comparison, an HDA amplification product solution was diluted to different final concentrations and loaded to gel and assay for side-by-side analysis (FIG. 6). Clear visual signal was observed using assay detection even when the amplicons were shown as a very faint band by gel analysis with a dilution factor of 32 fold (FIG. 7). These results demonstrate that comparable sensitivity is obtained with the NA assay.

Sensitivity Evaluation of HDA-Coupled NA Assay Detection:

The amplification sensitivity of HDA on Ba genomic DNA was investigated by carrying out HDA reactions with decreasing amounts of starting Ba genomic DNA, from 3000 copies to 3 copies. The amplification products were analyzed by gel electrophoresis and assay detection. As shown in FIG. 7, the yield of amplification product decreased as the starting genomic copy number was reduced, indicating the sensitivity of the assay to the initial starting material. The results also showed that as little as 30 copies of Ba genomic DNA was efficiently amplified and detected using gel and assay analysis (FIG. 7). These results were extremely reproducible using the NA assay system.

To further demonstrate the specificity and sensitivity of the HDA-coupled assay for rare target detection in a highly heterogeneous field sample, a series of complex genomic DNA mixtures were prepared by mixing 100 copies of Ba genomic DNA with 1 to 10000 times of excess Bt genomic DNA (a near neighbor of Ba), and subjected to HDA reactions. The amplification products were analyzed by both gel and assay detection. No significant signal differences were observed among different sample mixtures on gel and NA assay, suggesting that HDA-based NA assay detection was highly efficient and specific for rare Ba target amplification, and less sensitive to the varying amount Bt genomic background (FIG. 8).

Multiplexed HDA Amplification and NA Assay Detection:

To investigate the potential multiplexing capability of HDA amplification and NA assay detection, two HDA primer pairs (the same as used for amplifying pag and cap above) were tested in a multiplexed HDA reaction. The HDA products were analyzed by 8% nondenaturing gel electrophoresis and NA assay (FIG. 9). Because the two amplicons were close in length, two discrete bands could not be resolved by gel (FIG. 9, left panel). However, two amplicons were clearly detected by the two positive signals appearing on Pag and Cap capture spots in the lateral flow NA assay (FIG. 9, right panel, HDA lane). The signal intensity difference of cap and pag in the assay results reflected the differing amplification efficiencies of cap and pag, as demonstrated by the single-plex results discussed above (see FIG. 5). These results show that the HDA-based NA assay system may be applied in multiplexed situations.

Example 2

Extraction and Amplification of Influenza RNA from Immunomagnetically Captured Virus This example shows the effective extraction of amplifiable RNA from influenza A virus using a combination of immunomagnetic affinity capture of influenza A virus and NaOH lysis. Extracted RNA was subjected to RT-PCR as an indicator of the quality of the RNA so extracted.

Materials and Methods:

Influenza A strain, A/Sydney/5/97 (H3N2 strain). Negative control, MDCK cells (not infected with virus). Positive control, viral RNA extracted from partially purified A/Sydney/5/97 using Qiagen kit RNeasy (~10⁶ pfu).

For the first set of experiments, the bead-avidin/biotin-antiflu antibody system was used to isolate virus from media, isolated virion preparation was stored at −70° C. Frozen virion preparation was purified by filtration through a 0.2 μm filter post-infection of MDCK cells, so the samples contained a significant amount of cell debris. No other handling of the virus was performed prior to addition to the bead mixture.

5, 25, and 100 μL of ~$10^6$-$10^7$ pfu/mL A/Sydney/5/97 (H3N2) was added directly to 200 ng of anti-influenza A (polyclonal from goat, raised against Influenza A/Texas/1/77 (H3N2)) in 500 μL 10 mM PBS, pH 7.2 and rotated at room temperature for 2 hours. To this solution was added 20 μL of a 10 mg/mL suspension of magnetic beads-avidin and rotated overnight at 4° C. For the negative control throughout, the mock viral culture was used in equal volumes and treated in an identical manner.

The beads were then washed twice with 200 μL of a 10 mM PBS/BSA (0.1% w/v) then twice with 200 μL of $H_2O$, and resuspended in 50 μL water. To a PCR tube containing all the components necessary for RT-PCR (using the Taqman® Kit) was added 5 μL of the bead suspension to final volume of 20 μL. The remaining 45 μL of the bead-flu suspension was treated with 15 μL of a 0.1 N NaOH solution at room temperature for 10 minutes then neutralized to pH 7.0 with 15 μL of a 0.1 N HCl solution. To a PCR tube containing all the components necessary for RT-PCR was added 7.5 μL of the lysed virus-bead solution (no beads were added) to a final volume of 20 μL. The mock was treated in an identical manner for both the bead suspension and NaOH lysis.

Figure 10:
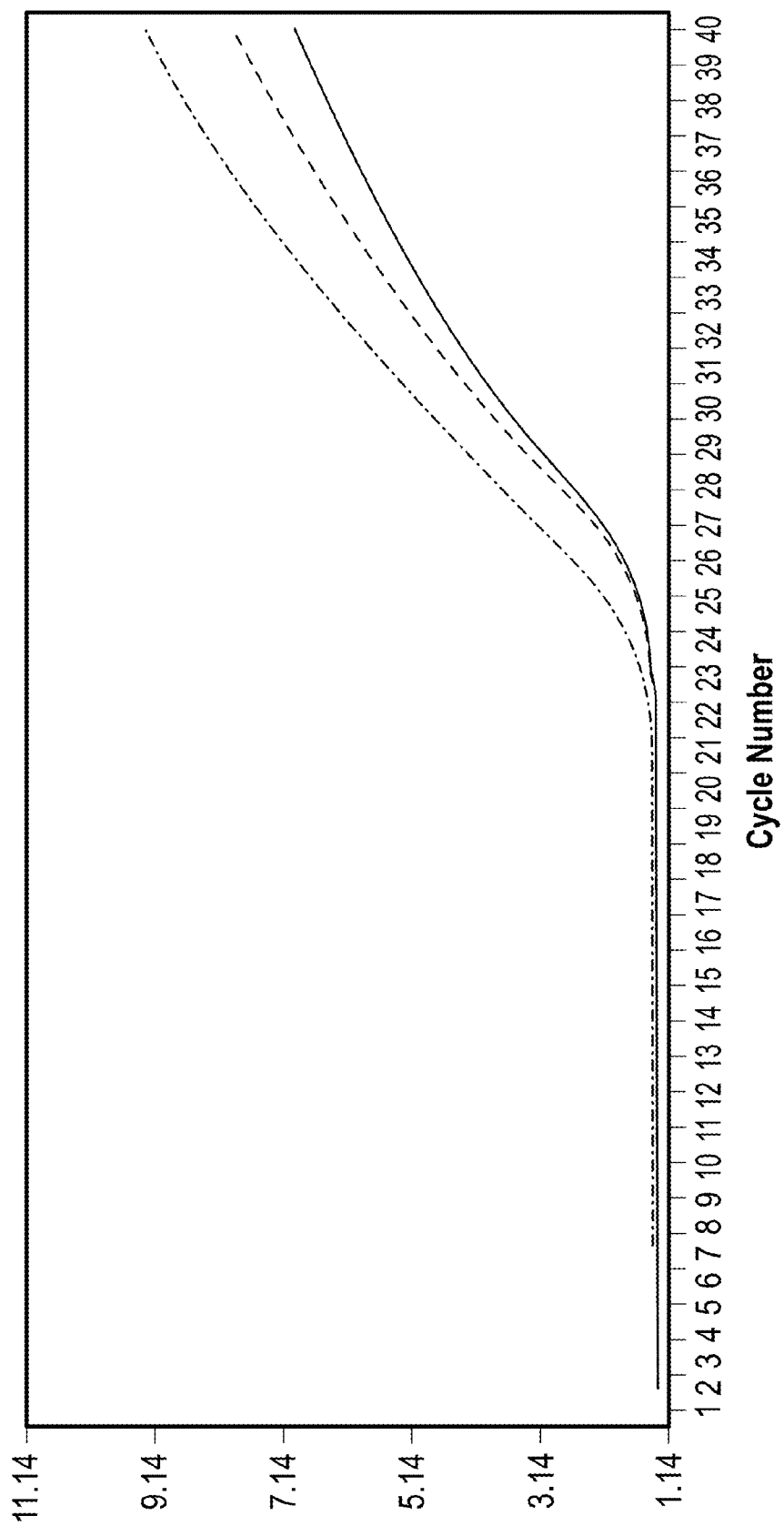
FIG. 10. Amplification plots of RT-PCR reactions on influenza viral RNA extracted from immunomagnetically-captured virions using NaOH lysis. See Example 2.
Figure 11:
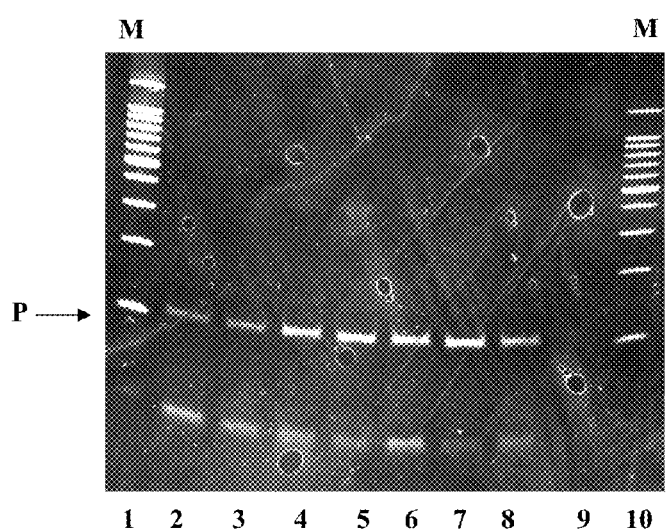
FIG. 11. SDS-PAGE analysis of RT-HDA reactions on influenza A RNA. Lanes 1-3: virus+beads (5, 25 and 100 µL virus, respectively). Lanes 4-6: virus+lysis (5, 25 and 100 µL virus, respectively). Lane 7, positive control (RNeasy).

RT-PCR was performed with the Taqman® Kit (Applied Biosystems Inc.) using the primers and probe approved by the CDC for real-time reverse transcriptase-PCR of influenza A.
Results:

The results of the RT-PCR are shown in FIG. 10. PCR products visualized by SDS-PAGE analysis are shown in FIG. 11.

A typical run consisted of one step at 48° C. for 30 minutes, one step at 95° C., then 40 cycles of 95° C. for 15 seconds and 60° C. for one minute. When the beads were added directly to the PCR tube, the initial heating step at 48° C. was sufficient to release the vRNA into solution for the RT-step (see FIG. 11, lanes 1-3). At approximately the same viral load for both the heating and NaOH-lysis methods the amplified product crossed the fluorescent signal threshold only three cycles apart, indicating the initial concentration of vRNA present for the RT-step were similar. Analysis of the amplified products by SDS-PAGE indicate only the expected fragment at ~100 bp was observed, thus demonstrating the specificity of the designed primers and the absence of non-specific sequence amplification. The band observed at ~50 bp is due to the formation of primer-dimers.

Example 3

Figure 12:
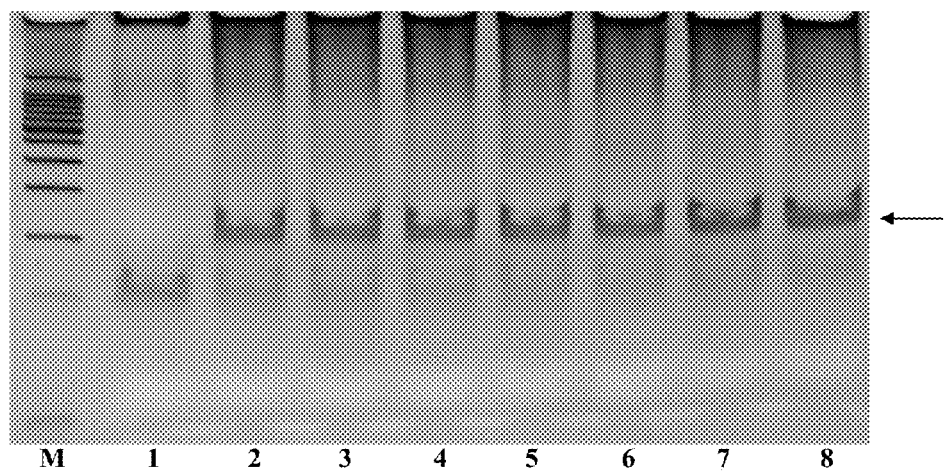
FIG. 12. rBst RT-HDA amplification, agarose gel showing amplification products from: lane 1: Flu rBst RT & HDA negative control; lanes 2, 3: Flu rBst RT 60 minutes; lane 4: Flu rBst RT 50 minutes; lane 5: Flu rBst RT 40 minutes; lane 6: Flu rBst RT 30 minutes; lane 7: Flu rBst RT 20 minutes; lane 8: Flu rBst RT 10 minutes.
Figure 13:
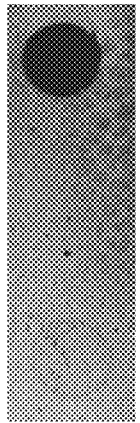
FIG. 13. Shows results of detection of amplified influenza RNA using combined RT-HDA reaction followed by capture with detection oligonucleotide functionalized dyed microbeads and detection on nitrocellulose lateral flow membrane printed with influenza-specific capture oligonucleotides. Top circle: influenza-specific, bottom circle, negative control.

Amplification of Influenza RNA Using Isothermal RT-HDA and Detection Using Lateral Flow Nucleic Acid Assay This example demonstrates successful amplification and detection of influenza A viral RNA using isothermal RT-HDA in combination with lateral flow detection.
Materials and Methods:

Single-step RT-HDA reaction: A single reaction in a volume of 20 μl containing 10×HDA annealing buffer in IsoAmp® tHDA kit (Biohelix®, Beverly, Mass.), 100 nM influenza A-specific primers, influenza A RNA, 500 mM dNTPmix (Invitrogen, Carlsbad, Calif.), 5 mM $MgCl_2$, 0.01M DTT, 40 units of RNaseOUT™ (Invitrogen, Carlsbad, Calif.), and 10 units of rBst DNA polymerase, Large Fragment (IsoTherm™) (EPICENTRE, Madison, Wis., USA), was prepared and incubated at 65° C. for 10 minutes. Then, 5 units of Hybridase (Thermostable RNaseH) (EPICENTRE, Madison, Wis., USA), was added to the reaction followed by 20 minutes incubation at 65° C. The HDA reaction was initiated by adding 10×HDA annealing buffer in 25 μl of 2×tHDA mastermix (both from Biohelix®, Beverly, Mass.). The total volume of the combined rBst RT and HDA reactions was 50 μl. The rBst RT and HDA reaction was continually incubated at 65° C. for 90 minutes before application to the lateral flow assay strip. In one experiment, dyed microbeads functionalized with capture oligonucleotide complementary to one part of the target sequence were added directly to the combined RT-HDA reaction mixture 10 minutes prior to the termination of the RT-HDA incubation. After termination of the reaction, the mixture was loaded onto a lateral flow detection strip printed with detection oligonucleotide complementary to a unique region of the amplified target nucleic acid.
Results:

The amplification results of the combined RT-HDA reactions is presented in FIG. 12, showing effective amplification of the target nucleic acid. The results of the lateral flow assay are shown in FIG. 13, and demonstrate specific identification of the target sequence.

Example 4

Immunomagnetic Capture of Influenza a Virions and Heat Extraction of Viral RNA

This example shows the effective extraction of amplifiable RNA from influenza A virus using a combination of immunomagnetic affinity capture of influenza A virus and heat-lysis. Extracted RNA was subjected to RT-PCR as an indicator of the quality of the RNA so extracted.
Materials and Methods:
General Materials:

Carboxy-coated magnetic beads (1 μm) were purchased from BioClone, Inc. All antibodies were purchased from BioDesign, Int. (Saco, Me.) and used without further purification. EDAC, S-NHS, and buffer components were purchased from Fisher Scientific, Inc. The PAb-coated magnetic beads were either transferred manually on a magnetic holder or transferred automatically on an ABI KingFisher96 robot.
Immobilization of Anti-Flu Polyclonal Antibodies to Magnetic Beads:

Anti-influenza-A polyclonal antibodies (PAb) were immobilized to carboxy-coated magnetic beads using a standard two-step protocol for covalently attaching antibodies to the beads, as follows. In order to assure surface saturation of the surface as a single monolayer approximately 5-10 fold excess PAb was necessary. Briefly, 10 mg of magnetic beads were washed twice with MES, pH 6.0 and resuspended in the same buffer. To the suspension were added EDAC and S-NHS, and the mixture was allowed to react in the dark with rotation at room temperature for one hour, at which time additional EDAC was added and allowed to react in a similar manner. The supernatant was removed, beads washed twice with the same buffer, then resuspended in phosphate buffer, pH 7.5. Immediately thereafter, a PAb solution was added and allowed to react overnight at room temperature in the dark with gentle rotation. The following day, ethanolamine-HCl, pH 8.0 was added to quench the reaction. The beads were washed extensively with conjugation buffer then resuspended at a final concentration of 10 mg/mL in PBS/BSA and stored at 4° C.

Capture of Virus Particles:

PAb-coated magnetic beads were added to blocking buffer (PBS/Tween/BSA) and mixed by rotation. The beads were transferred to the same buffer containing serial 10-fold dilutions of the appropriate viral strain (either purified virus or virus diluted into flu-negative human nasopharyngeal aspirate solution) and allowed to bind to influenza virus particles for 30 minutes. The beads were washed twice with PBS/Tween, twice in PBS/BSA, then resuspended in 50 µL ddH$_2$O.

Extraction of Viral RNA:

Influenza viral RNA was extracted by heating the virus-PAb-magnetic bead at 95° C. for 3 min or 60° C. for 30 min. Either treatment was sufficient to release at least 90% of the viral genome as determined by real time RT-PCR when compared to total RNA isolation using commercial kits (Ambion®, Inc., MagMax™ Viral Isolation Kit and Qiagen Total RNA Isolation Kit). The reactions were performed and analyzed in a 7300 Real Time PCR System (ABI) under the following conditions: 15 min at 45° C. and 10 min at 95° C., followed by 50 cycles of 15 s at 95° C. and 45 s at 60° C.

For the quantitative assay, the threshold cycles of spiked clinical samples were directly compared to a standard curve generated by RT-PCR of known numbers of influenza A RNA transcripts. The results are presented as influenza A copies (or individual particles) per 10 µL of the original serially diluted virus stock. All samples were run in triplicate.

Results:

As few as 10 copies of matrix gene RNA was detected by RT-PCR using the Ambion Flu M gene detection kit. The specificity of influenza A towards the differentially coated PAb magnetic beads was determined using 10-fold serial dilutions of partially purified influenza spiked (both H3N2 and H1N1 strains) into either PBS or human nasopharyngeal aspirates (NPA). The NPA samples were previously determined to be negative for influenza A by both the supplier and by our own analysis. The Pab-functionalized magnetic beads were able to recognize both the H3N2 and H1N1 influenza A strains. Minimization of non-specific binding of influenza A to non-anti influenza A PAb-coated magnetic beads was accomplished when a mild detergent was introduced into the blocking buffer in the presence of high concentrations of BSA. Optimization led to a complete sequence of blocking, binding, washing and elution.

The pulldown efficiency was determined by RT-PCR using a commercial kit (Ambion, Inc.) against a standard of known quantity. The standard was a ssRNA oligonucleotide identical to the target sequence in influenza A, specifically a highly conserved ~100 base region at the N-terminus of segment 7, which encodes the matrix (M) gene. We assessed the efficiency of the pulldown based on the total number of viral particles. This was necessary since typical influenza A preparations often contain as much as 90% non-infectious particles, which would be expected to be detected by RT-PCR but not by the plaque assay. Based on our standard curve, a positive result contained a threshold value (Ct) <35-36.

When 10-fold serial dilutions of influenza A were spiked into either PBS or NPA, the PAb-functionalized magnetic beads were able to recover, on average, approximately 3-9% of the total virus originally spiked into the solution. This number represents the lower limit of total viral particles that were recognized by the PAb-coated magnetic beads. Since the standard of total viral particles was based on total viral RNA present in the original sample, it is very likely a large percentage of the virus was not recognized by the PAb-coated magnetic beads due to free viral RNA present in the original sample and/or incorrect folding of the viral coat proteins. Of importance was the observation of very little loss of sensitivity when tested on clinical samples, which could cause problems due to increased viscosity and the presence of potential inhibitors of the RT-PCR. Results of the pulldown are presented in Table 2. The results are reported as total copies of viral RNA/viral particles spiked into either PBS or NPA. Typically, 10 µL of 10-fold serial dilutions were spiked into 50 µL of either PBS or NPA then added to 150 µL of binding buffer. For each extraction, 10 µL of an approximate 10 mg/mL PAb-coated magnetic beads were sufficient for maximizing virus isolation. For % recovery, the value reported represents the average pulldown efficiency of each virus strain for the clinical samples.

TABLE 2

INFLUENZA PARTICLE RECOVERY FROM NPA AND PBS

| Initial copies of viral genomic RNA/extraction | Output by RT-PCR H3N2 (PBS/NPA) | Output by RT-PCR H1N1 (PBS/NPA) | % Recovery (H3N2/H1N1) |
|---|---|---|---|
| $10^6$ | $6 \times 10^4 / 5 \times 10^4$ | $9 \times 10^4 / 6 \times 10^4$ | 5%/6% |
| $10^5$ | $8 \times 10^3 / 4 \times 10^3$ | $4 \times 10^3 / 6 \times 10^3$ | 4%/6% |
| $10^4$ | $4 \times 10^2 / 3 \times 10^2$ | $7 \times 10^2 / 5 \times 10^2$ | 3%/5% |
| $10^3$ | $7 \times 10^1 / 5 \times 10^1$ | $8 \times 10^1 / 6 \times 10^1$ | 5%/6% |

Example 5

One-Step RT-HDA Amplification of Influenza a RNA Using Poly dT Fork-Generating Primers Materials and Methods:

General Materials: The enzymes and reagents for the HDA were purchased from BioHelix, Inc (Beverly, Mass.). Isotherm DNA polymerase (rBst) and Hybridase thermostable RNaseH for rBst RT step were purchased from Epicentre (Madison, Wis.), and the other reagents (MgCl$_2$, DTT, dNTP mix and RNaseOUT) were purchased from Invitrogen (Carlsbad, Calif.). Protein concentrations were determined by the method of Bradford. RNA/DNA concentrations were determined by absorbance at 260 nm. Viral stocks were grown on MDCK cells and the number of infectious particles determined by plaque assay (pfu/mL).

Primers:

Three sets of primers were used:
1) MP_2 Primers:

5'-TCCTGTCACCTCTGACTAAGGGGATTT-3'   [SEQ ID NO: 16]

5'-RAGGGCATTTTGGACAAAGCGTCTAC-3'   [SEQ ID NO: 17]

2) Poly dT Primers:

[SEQ ID NO: 18]
5'-TTTTTTTTTTRAGGGCATTTTGGACAAAGCGTCTAC-3'

[SEQ ID NO: 19]
5'-TTTTTTTTTTCCTGTCACCTCTGACTAAGGGGATTTTR-3'

3) Poly dI Primers:

```
                                          [SEQ ID NO: 20]
5'-||||||||||RAGGGCATTTTGGACAAAGCGTCTAC-3'
```

```
                                          [SEQ ID NO: 21]
5'-||||||||||TCCTGTCACCTCTGACTAAGGGGATTTTR-3'
```

RT-HDA Reaction Mixtures and Protocol:

Each RT-HDA reaction contained the following reagents from the Biohelix IsoAmp II tHDA kit: 5 μL 10× Annealing Buffer, 1.75 μL MgSO$_4$ (100 mM stock), 4 μL NaCl, (500 mM stock), 3.5 μL dNTP mix, and 3.5 μL enzyme mix. In addition, each reaction contained 2 μL Influenza-A RNA template (Puerto Rico 8/34; 5×10$^5$ copies/4 stock), 5 μL Fwd. primer (1 μM stock), 5 μL Rev. primer (1 μM stock), 0.5 μL Thermoscript™ reverse transcriptase (2 U/μL, Invitrogen) or otherwise stated, and nuclease-free H$_2$O to a final volume of 50 μL. Serial 10-fold dilutions of Influenza-A Puerto Rico strain RNA were made in order to vary the copy number from 10$^3$-10$^4$ copies per reaction. Using a similar protocol, a positive tHDA control was run alongside the RT-HDA reactions. This reaction used a DNA template, and thus required no reverse transcriptase. All reagents were added according to the above protocol excepting the following discrepancies: 0.75 μL of each primer, 1 μL DNA template, and 2 μL MgSO$_4$ (100 mM stock). Positive DNA template and primers were included in IsoAmp II tHDA kit and used as directed. These reactions were incubated at 65° C. using a thermocycler for 90 min or otherwise stated. Labeling of the amplification product were achieved An aliquot of 20 μL from each reaction was loaded onto a 10% polyacrylamide TBE gel and run for 100 min at 100 V.

Figure 14:
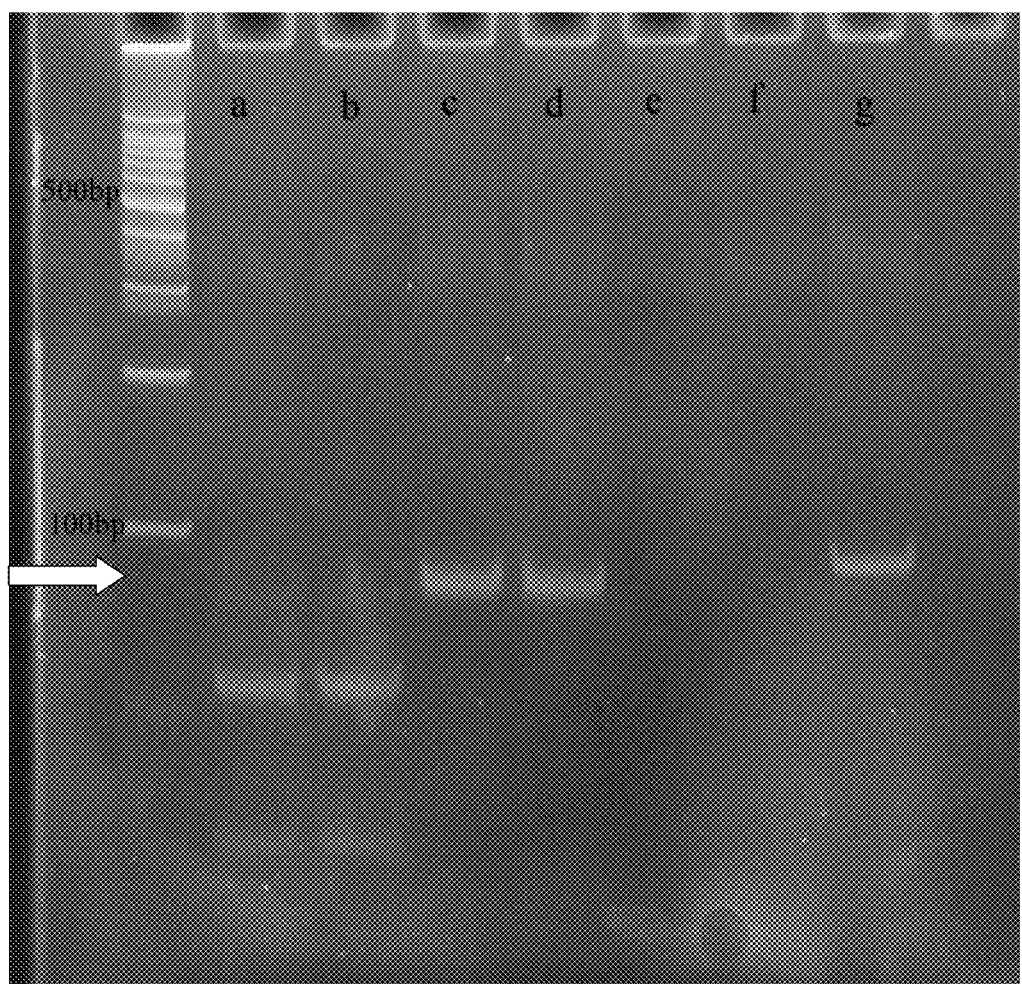
FIG. 14. Gel analysis of one-step flu RT-HDA amplification products using Thermoscript™ reverse transcriptase (RT) and HDA enzymes (polymerases and helicases). Lane a: MP-2 primers, with $10^4$ copies of template RNA; b: MP-2 primers, with $10^3$ copies of template RNA; c: poly dT primers, with $10^4$ copies of template RNA; d: poly dT primers, with $10^3$ copies of template RNA; e: poly dI primers, with $10^4$ copies of template RNA; f: poly dI primers, with $10^3$ copies of template RNA; g: positive tHDA control primer and template set. The flu amplification product bands are indicated by the arrow; lower bands are primers or primer dimmers.

Results:

Poly dT Fork-Generating Primers Result in High-Efficiency RT-HDA:

The results of this study are presented in FIG. 14. The poly dT primer sets supported a much more efficient amplification reaction, as demonstrated by the significantly higher yields of amplification product in Lane c and d, compared with amplification supported by the unmodified primer set, which only yielded very faint product bands and two other non-specific primer dimmer bands (Lane a and b). These results clearly demonstrate that low melting point, fork-generating primers facilitate more efficient helicase-mediated amplification reactions, most likely due to more efficient helicase loading at poly dT ends. Interestingly, the use of 5' random sequence primer and poly I primer did not produce any specific amplification products (FIG. 14. Lane c-f), in a good agreement with the previous report that UvrD-like helicases do not prefer primer substrates with 5' overhangs.

Figure 15A:
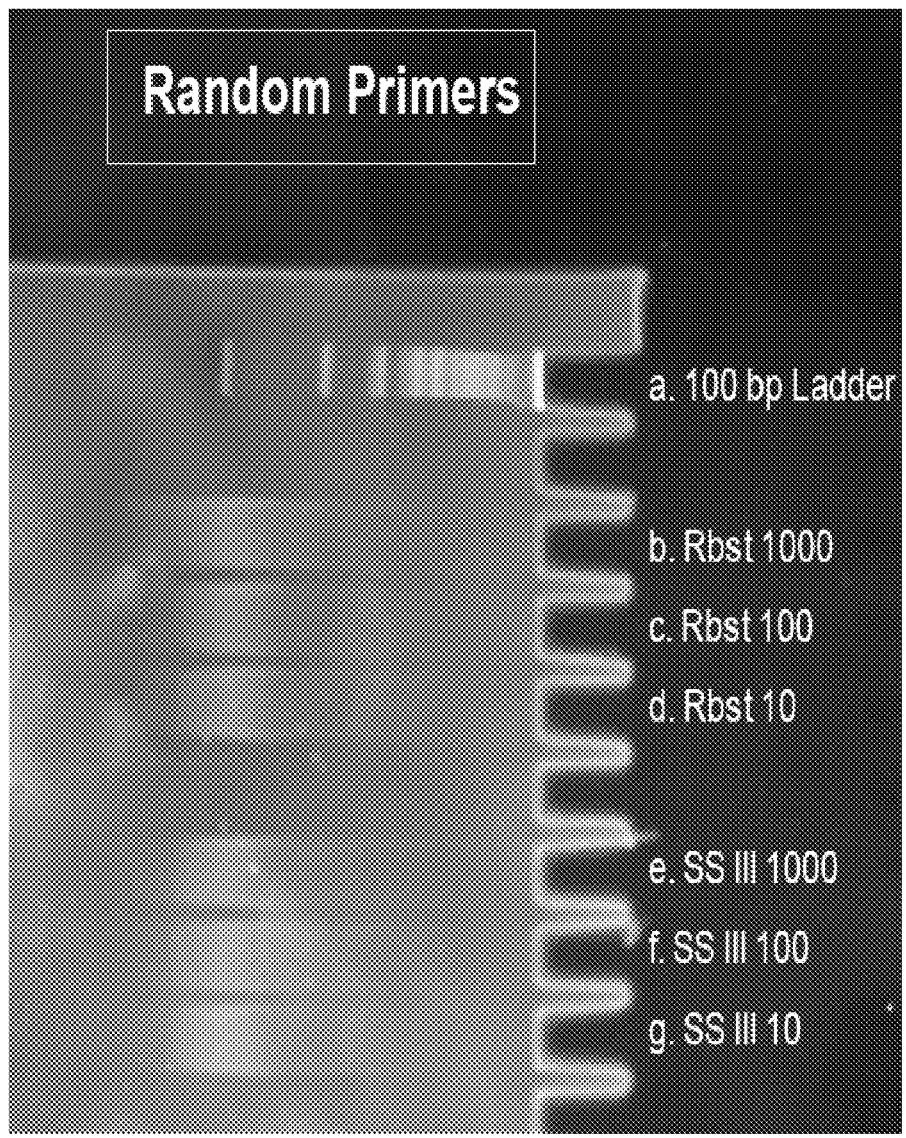
FIG. 15. Gel electrophoresis analysis of flu RT-HDA amplification products using Superscript III (SS III, Invitrogen) and rBst pol (Epicentre) as reverse transcriptase (RT) together with HDA enzymes (polymerases and helicases). Panel (A), (B) and (C) RT-HDA reaction using random flu primer set, regular MP-2 primer set and poly dT primer sets as described in Example 5, infra. The 100 bp size standards, positive, negative controls, the RTs and the flu template RNA copies are labeled next to each lane. The flu amplification product bands are indicated by the arrow; lower bands are primers, primer dimmers, or non specific amplification smears.
Figure 15B:
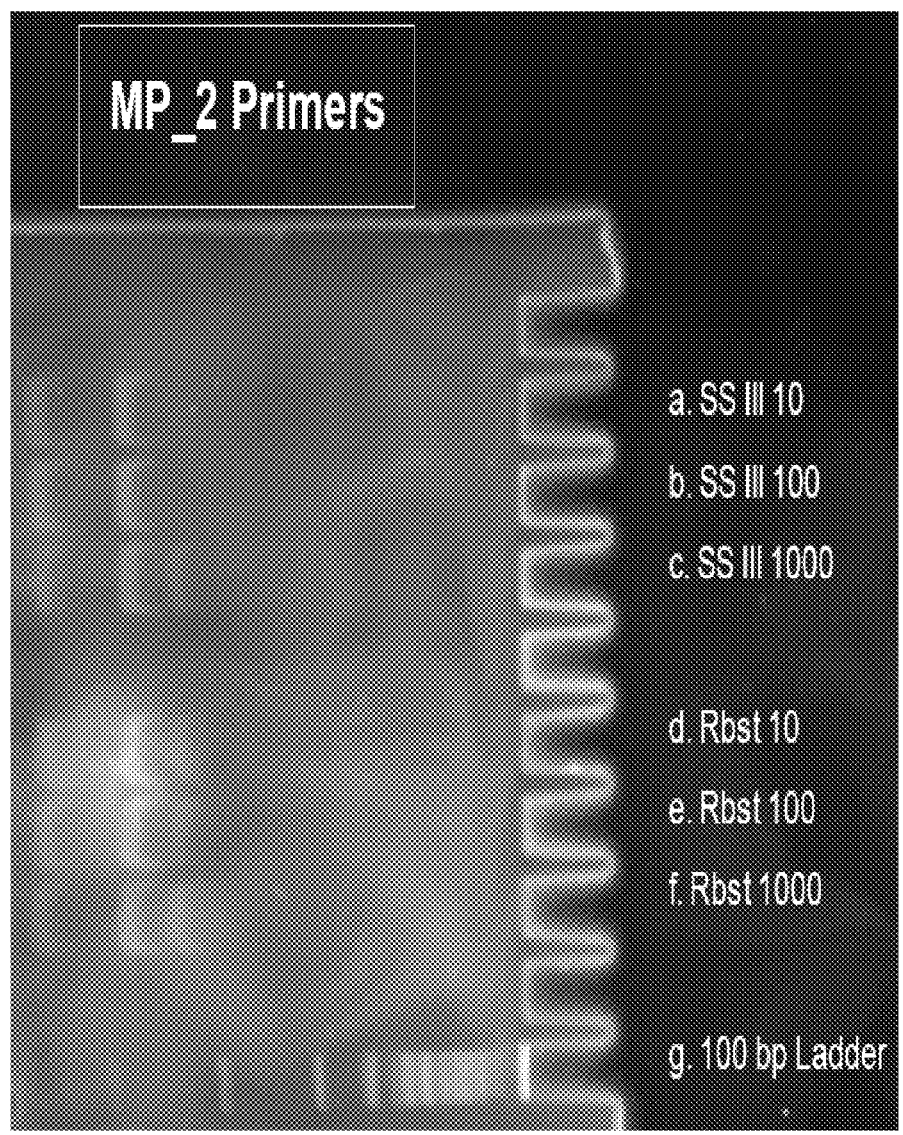
Figure 15C:
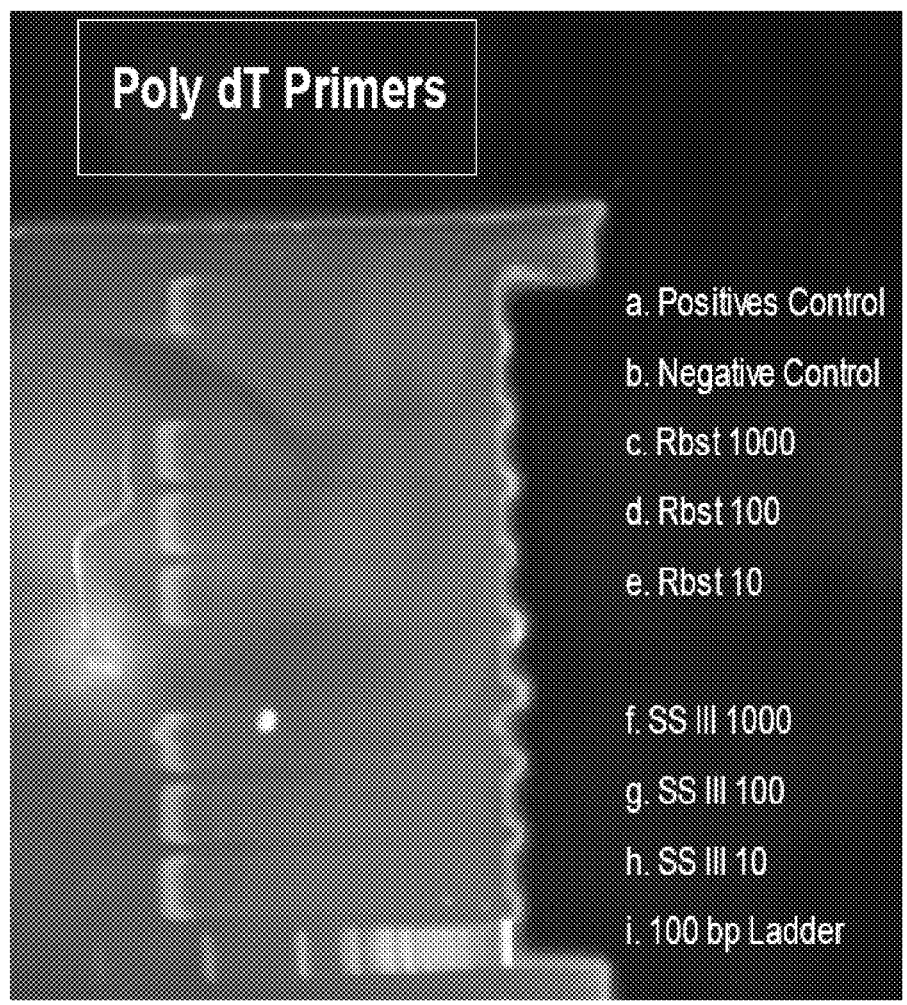

Poly dT Fork-Generating Primers Enable the Use of Variable Reverse Transcriptases:

Thermoscript™ is suggested by BioHelix to be the preferred reverse transcriptase to work with its commercial Iso-Amp II tHDA kits. To explore the compatibility of other RTs with RT-HDA reaction, Superscript (SS III), and Bst (a strand displacement polymerase that can also function as RT) were used as RT enzymes in conjunction with different primer substrates in flu RT-HDA reactions (FIG. 15). Interestingly, the result show that when the RT-HDA reaction is primed with Poly dT primers, both SS III and Bst polymerases can be used, enabling good amplification from as little as 10 copies of flu target RNA (FIG. 15, Panel C). In contrast, if the RT-HDA reaction is primed using the standard MP-2 primer, then Bst polymerases seemed to be a better RT than SS III, since SSS III-HDA amplification had amplification sensitivity of 10 copies (FIG. 4, Lane d, e, f, vs. a, b, c).

In terms of RT-HDA amplification efficiency, the use of poly T primers yielded higher quality and quantity of amplified DNA compared with the use of standard primers. This result again demonstrated that RT-HDA amplification primed by poly dT, fork-generating primers, dramatically improves the efficiency of the overall RT-HDA reaction, essentially relaxing the requirement for specific RT enzymes. More importantly, these results also demonstrate that rBst polymerase can also be used as a RT enzyme, therefore potentially reducing three enzymes, Thermopscript, helicase and rBst pol for conventional RT-HDA to two enzyme-based (helicase and rBst pol) RT-HDA.

Figure 16:
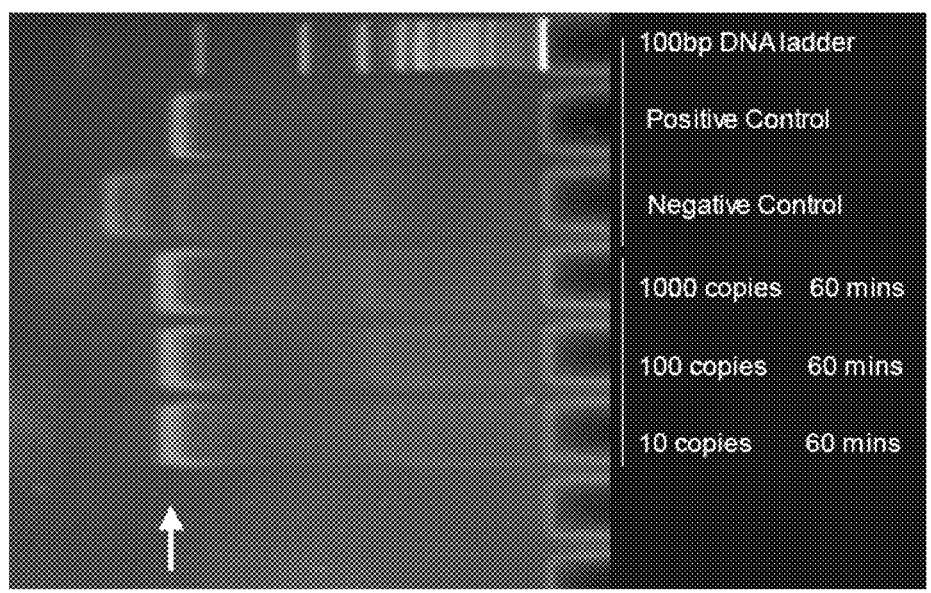
FIG. 16. Reduced assay time for one step RT-HDA reaction. The gel electrophoresis analysis was performed for the one-step RT-HDA reaction with poly dT flu primers and an rBst pol-based HDA kit. The product band is indicated by the arrow. The positive and negative control reactions, RT-HDA assay time and the copy numbers of the flu RNA templates are marked.
Figure 17:
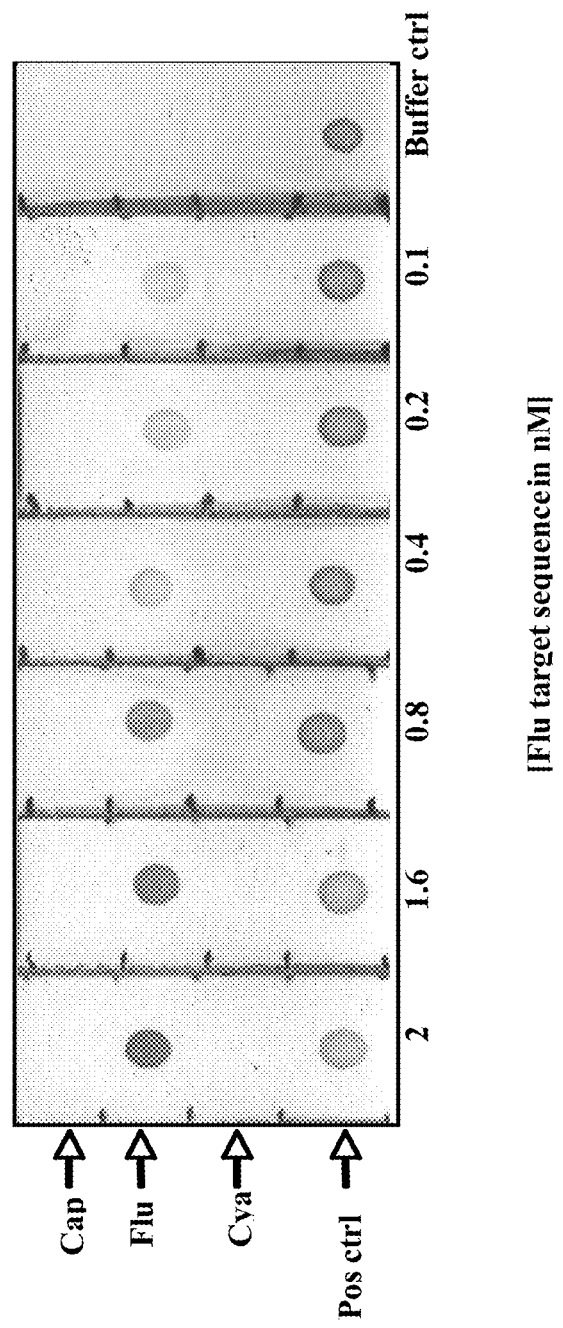
FIG. 17. Detection sensitivity of the NA lateral flow assay on synthetic Flu target sequences. Each lateral flow assay strip was imprinted with four different gene capture probes, Cap B, Flu, Cya and Positive control sequence (complementary to the Flu detection probe of the dyed microspheres). Hybridization reaction mix containing varying concentration of Flu target (from 0 to 2 nM final concentration, from right to left) and Flu detection oligonucleotide probe functionalized with blue microspheres in 1× hybridization buffer was applied on individual NA lateral flow assay, respectively, as described in Example 6.

Poly(t) Priming Results in Faster RT-HDA Reaction Times:

A time course study using poly dT primers, and rBst polymerase as a RT, in a one-step RT-HDA reaction decreases assay reaction times by between a third and a half (FIG. 16). Unlike previous assays, which require a 90 minute reaction time (Example 3, supra), the new poly dT primer-rBst pol-HDA combination enabled good amplification of as little as 10 flu RNA template copies in 60 minutes, whereas standard primer reactions yielded no discernable amplification product within this shortened time frame (FIG. 16). Moreover, based on preliminary data, it appears that a 45 minute reaction may be sufficient for this one step RT-HDA protocol.

Example 6

Lateral Flow Capture of RT-HDA Amplified Influenza a Target Sequences

Materials and Methods:

General Materials and Methods: Carboxy-coated blue microspheres (0.39 μm) were obtained from Spherotech, Inc (Lake Forest, Ill.). Oligonucleotides were purchased from IDT (Coralville, Iowa). EDAC, S-NHS, and buffer components were purchased from Fisher Scientific, Inc. The enzymes and reagents for the HDA were purchased from BioHelix, Inc (Beverly, Mass.). The nitrocellulose membrane cards with clear polyester material backing, conjugation and absorption pads were purchased from MILLIPORE Corp. (Billerica, Mass.). Isotherm DNA polymerase (rBst) and Hybridase thermostable RNaseH for rBst RT step were purchased from Epicentre (Madison, Wis.), and the other reagents (MgCl$_2$, DTT, dNTP mix and RNaseOUT) were purchased from Invitrogen (Carlsbad, Calif.). Protein concentrations were determined by the method of Bradford. RNA/DNA concentrations were determined by absorbance at 260 nm.

Primers, Capture and Detection Probes:

Shown in Table 3 are the oligonucleotides used in this Example. A "+" precedes an LNA residue. "NH2" indicates a 5' amine group modification, "Phos" indicates 3' phosphoryl.

TABLE 3

PRIMERS AND PROBES USED IN EXAMPLE 6

HDA amplification primers

| | | |
|---|---|---|
| Forward: | FluFP | 5'-AGATGAGTCTTCTAACCGAGGTCG-3' [SEQ ID NO: 22] |
| Reverse: | FluRP | 5'-Biotin/TGCAAAAACATCTTCAAGTCTCTG-3' [SEQ ID NO: 23] |

TABLE 3-continued

PRIMERS AND PROBES USED IN EXAMPLE 6

Oligonucleotides for microsphere conjugation

Bead/HDA fluJian    5'-NH$_2$C$_{12}$/TTTTTTTTTTTT/TCTATCGTC+CCGTCAGGC+CC/3Phos/-3' [SEQ ID NO: 24]

Oligonucleotides for membrane immobilization

Flu capture probe    5'-G+CCG+AGATCGCG/TTTTTTTTTTTT-3' [SEQ ID NO: 25]

Neg ctrl capture probe 1 (CapB)    5'-TACATGGTCTTCCCAGATAA/TTTTTTTTTTTTTT-3' [SEQ ID NO: 26]

Neg ctrl capture probe 2 (Cya)    5'-TGCTAGAGAATTAAATACATATA/TTTTTTTTTTTTTT-3' [SEQ ID NO: 27]

Synthetic target sequences for dipstick characterization

Flu target sequence    5'-CGCGATCTCGGCTTTGAGGGGGCCTGACGGAACGATAGAGAGAACATACGTT-3' [SEQ ID NO: 28]

Nucleic Acid Lateral Flow Assay:

The overall configuration of the sandwich-based NA lateral flow assay is illustrated in FIG. 2. Two hybridization probes were used to label and capture an influenza specific ssDNA sequence previously reverse transcribed and amplified from viral genomic RNA: one detection probe was conjugated to dyed microspheres and the other a capture probe immobilized on the nitrocellulose membrane.

Conjugation of Oligonucleotides onto Dyed Microspheres:

In this Example, a highly conserved ~100 base region at the N-terminus of segment 7, which encodes for the matrix (M) gene of Type A Flu, was amplified. To detect the amplification products using lateral flow dipstick assay, a pair of labeling and membrane capture probes were designed to be complementary to the amplified flu sequences. To label/detect the target sequence (amplification product or synthetic target template oligomer), a specific detection probe harboring an amine modification group at the 5'-end (complementary to target sequence) was covalently conjugated to the carboxylated microspheres using standard EDAC (1-ethyl-3-(3-dimethylaminopropyl) carbodiimide hydrochloride) chemistry. The gene-specific detection oligonucleotide used for covalent coupling required four components: (1) a 5'-amine modification for amide coupling to the carboxyl-polystyrene microspheres; (2) a 12-carbon spacer to extend the oligonucleotide from the microspheres to increase the accessibility of oligonucleotide to its hybridization target; (3) a 12-mer poly(dT) linker for additional flexibility of the probe to increase hybridization efficiency; and (4) a 20-23 nt hybridization sequence complementary to the 5'-end of the gene target. Briefly, a typical conjugation reaction used the following protocol. Oligonucleotide (100 µM) was dialyzed against water for 4 h (Slide-A-Lyzer®, 10K) to remove residual salt, at which time the buffer was exchanged with 0.1 M 2-(N-morpholino) ethanesulfonic acid, pH 5.0 (MES), and allowed to stir overnight at room temperature. Conjugation of the desalted oligonucleotides to the microspheres was carried out by mixing 40 µl of 5.0% (w/v) carboxylated-polystyrene blue microspheres with 400 µl of 10 µM oligonucleotides followed by a brief sonication (1 minute with output setting of 7) using Sonifier® Cell Disruptor 200 from Branson Ultrasonics Corp. (Danbury Conn.). The conjugation reaction was initiated by adding ~3 mg EDAC to the microsphere/oligonucleotide mixture, followed by a 1 h incubation with gentle rotation at room temperature. The reaction was quenched upon addition of 4 µl of a 20% (w/v) SDS solution. Excess oligonucleotides were removed by a brief centrifugation at 7000 rpm (Eppendorf® 5415C, Eppendorf, Westbury, N.Y.), followed by two subsequent washes with 0.1% (w/v) SDS. Finally, the microspheres were resuspended in 400 µl of 0.1% (w/v) SDS and stored at 4° C.

Lateral Flow Device:

The lateral flow assay strip was assembled under the manufacture's instruction and consisted of the three parts: (1) sample pad (AP22) (20 mm×300 mm, B3HN43393); (2) hiflow plus membrane cards (type 6 cm×30 cm, SHF0900225 for HF090 or other membrane card with a different flow rate), and (3) absorbent pad (AP22) (17 mm×300 mm, B4JN49233). The three components overlapped in order to ensure continuous flow of the hybridization reaction from the sample pad to the absorbent pad. In this paper, four different gene capture probes were spotted on the membrane (sequences will be reported elsewhere).

Immobilization of Capture Probes onto the Membrane by UV Crosslinking:

Capture probes/oligonucleotides were designed with a 12-mer poly (dT) linker at the 3'-end and a 20-23 nt hybridization sequence complementary to the 3' end of target sequence. Capture probes were spotted onto the nitrocellulose membrane of preassembled strips dried at room temperature for 10 minutes, then exposed to ultraviolet light (UV) to crosslink the capture probe to the membrane (UV Stratalinker 2400, Stratagene, La Jolla, Calif.). The strips were stored at room temperature for future use.

Labeling Amplification Products Prior to Lateral Flow Detection:

Labeling of amplification products were achieved in several ways prior to applying it lateral flow detection: (1) amplification mixture was undergoing a thermal denaturation (94 degree for 1 minute), or (2) enzymatic degradation (e.g. using one 5'-phosphorylated amplification primer in HDA, and exonuclease A for post-amplification digestion for 10 minutes at room temperature) prior to application to the lateral flow assay strip. (3) Labeling of amplification product can be carried out by adding dyed microspheres bearing detection probes with an inactive 3' (e.g. modified by an phosphate or thiolated group instead of a active 3' hydroxy group for primer extension). The sequence of probes had the same as described before except the primer bears an inactive phosphate group. Microsphere bearing probes (5 µl) was added to isothermal amplification reaction (40 µl).

Detection of Amplified Target Sequences:

Hybridization of the amplification product (30 µl) or the synthetic equivalent (2 µl) was achieved by mixing 10 µl of labeled microspheres with 2× hybridization buffer (1.5×SSC, 0.2% Ficoll, 0.2% Gelatin, 2% triton X-100 and 40 mM $Na_2HPO_4$, pH 7.4). Following a brief incubation period at room temperature, the mixture was applied to the sample pad of the lateral flow assay device. The blue solution was allowed to migrate through the membrane via capillary action. Upon passing the capture spot immobilized with capture probes, a sandwich complex formed among detection probe, target sequence, and capture probe resulting in a clear blue signal that was directly visualized by eye. The images scanned by Epson 2580 Photo Perfection scanner were processed by Adobe PhotoShop image analysis software. The appearance of a signal ranged from 2 to 30 minutes, and was a direct result of the particular membrane, the size and the number of microspheres and concentration of target sequence. The typical assay used for the detection of the HDA amplification product was ~5 minutes.

Results:

Several parameters of the lateral flow assay were optimized for maximal sensitivity and specificity. The variables examined were as follows: 1) nitrocellulose membranes with varying flow rates; 2) dyed microspheres with different diameters; 3) buffer conditions for hybridization of target sequence to both the oligonucleotide-conjugated microspheres and capture probe on membrane; 4) capture probe concentration on the membrane; and 5) incubation time and temperature of the initial hybridization of the target sequence to the labeled microspheres. The study indicated that the hybridization buffer with 0.75×SSC, 0.1% Ficoll, 0.1% Gelatin, 1% Triton X-100 and 20 mM $Na_2HPO_4$ would give the best hybridization signal with minimal background, and the combination of Hi-Flow Plus membrane 90 and 0.39 um microspheres provided optimal sensitivity and rapid (~5 min) detection.

Figure 18:
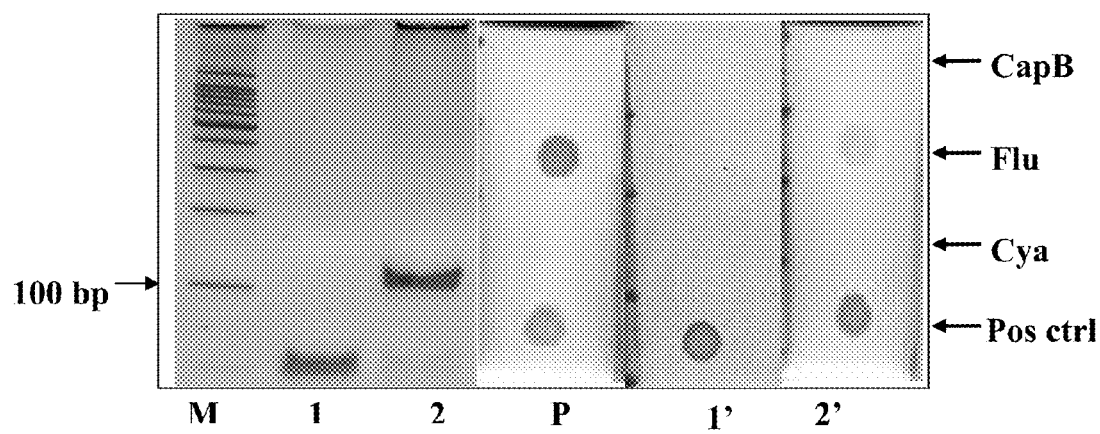
FIG. 18. Detection of Flu rBst RT-HDA products using 8% nondenaturing acrylamide gel electrophoresis and NA lateral flow detection. For each NA lateral flow assay strip, four capture oligonucleotide probes were immobilized on the membranes, CapB, Flu, Cya and Flu. In left gel image panels: M: 100 bp DNA ladder (Promega); Lane 1: no-template negative control; Lane 2: Flu RNA rBst RT-HAD amplification. Right NA lateral flow assay image panels: Lane P: Flu dipstick positive control with 2 nM Flu synthetic target synthetic target; Lane 1', NA lateral flow detection of Flu rBst RT-HDA amplification products; Lane 2', NA lateral flow detection of Flu rBst RT-HDA no-template negative controls.

Initial determination of the sensitivity and specificity of the device was accomplished with the synthetic Flu target sequence which is the single-stranded version of the expected amplification product from the rBst RT-HDA reaction (Note: the synthetic Flu target sequence was designed to contain the region of hybridization to both the detection probe and capture probe, i.e. there are no 5'- and 3'-overhangs. However, the synthetic Flu target sequence is identical to the expected region of hybridization from the HDA reaction). Under the optimal hybridization conditions, serial dilutions of the synthetic Flu target sequence were hybridized with the labeling/detecting probes and applied to the sample pad of the lateral flow device. As a negative control, two gene sequences, Cya and CapB, from the virulent bacterium *Bacillus anthracis* (Ba) were chosen to provide direct evidence for the absence of cross-reactivity with the target sequence. As depicted in FIG. 18, as few as 20 fmoles of the Flu target sequence (0.1 nM, 200 µl) were visualized, thus achieving comparable sensitivity observed from a typical homogeneous fluorescence assay (e.g. Taqman assay). In addition, the 20 fmoles of Flu is equivalent to approximately $1.2 \times 10^{10}$ copies, which was found to be an important detection limit. These results demonstrate that HDA can amplify cDNA over a billion-fold. There was no visible signal detected on the spots immobilized with CapB and Cya capture probes indicating the absence of cross-reactivity (high specificity) with the target sequence.

To detect the flu RT-HDA amplification product, the rBst RT-HDA reaction mixture was split into two aliquots and detected by both dipstick and non-denaturing PAGE/ethidium bromide staining in the presence of Flu RNA. In the absence of target RNA, only the faint appearance of primer-dimer was observed. When the rBst RT-HDA product was applied to the lateral flow device after hybridization to the labeled microspheres, the expected signal was observed on the device and, importantly, no cross-reactivity was observed with the Cya and CapB capture probes (FIG. 19).

Example 7

RT-HDA Primer, Detection Oligonucleotide and Capture Oligonucleotide Combinations for Influenza A This example provides several sets of oligonucleotide components useful in detecting the presence of seven different influenza A genes using the assay method of the invention (i.e., viral capture and RNA extraction, one-step RT-HDA, and sandwich hybridization capture of target using a lateral flow platform.

Materials and Methods:

Primers for use in the one-step RT-HDA reaction were designed in combination with coordinate detection and capture oligonucleotides using the following approach:
  a. Obtain all available sequences from multiple sources (e.g., GenBank, The Influenza Sequence Database at LANL).
  b. Perform multiple sequence alignments and develop consensus sequences at different taxa levels (e.g., different subtypes).
  c. Pick up all possible primer/probe sets along the whole molecule using Primer3 according to a set of given requirements.
  d. Introduce degenerate bases to maximize the coverage for all available strains.
  e. Rank the degenerate primer/probe sets according to multiple parameters (e.g., % coverage, degeneracy fold, # degenerate bases, native coverage, false positive rate, etc).
  f. Additional quality/robustness check on the highly ranked primer/probe sets for presence of possible hairpins using mFold and other secondary structures.
  g. Introduce locked nucleic acid (LNA) and add poly-T linkers to the primers and probes.

Results:

For each of the seven different influenza A gene targets, a set of amplification primers+capture and detection probes (oligonucleotides) were designed using the approach outlined above. Presented below are exemplary primer/probe sets for each of the designated genes. Sequences incorporating degenerate bases are shown using standard ambiguity codes. In the capture and detection probe sequences, a "+" proceeds any locked nucleic acid bases (LNA).

1. MP Gene Target:
  Degenerate Primer Pair:

```
                                     [SEQ ID NO: 29]
    5'-RCMGATCTYGAGGCTCTCATGGARTGG-3'
```

```
                                     [SEQ ID NO: 30]
    5'-GAGCGTGAAYACAAAYCCYAARATC-3'
```

LNA Capture Probe Oligonucleotide:

```
                                     [SEQ ID NO: 31]
    5'-TT+CA+CG+CT+CACTTTTTTTTTTTT-3'
```

LNA Detection Probe Oligonucleotide:

[SEQ ID NO: 32]
5'-TTTTTTTTTTTCG+AG+GACTG+CAGC-3'

2. HA Gene Target:
Degenerate Primer Pair:

[SEQ ID NO: 33]
5'-GCRAAAGCAGGGGTHYRATC-3'

[SEQ ID NO: 34]
5'-CAGAGYTTYCCRTTRTGTG-3'

LNA Capture Probe Oligonucleotide:

[SEQ ID NO: 35]
5'-GA+CAG+AG+CA+GGTTTTTTTTTTTT-3'

LNA Detection Probe Oligonucleotide:

[SEQ ID NO: 36]
5'-TTTTTTTTTTTC+CC+AAGA+CA+TA+CT-3'

3. NA Gene Target:
Degenerate Primer Pair:

[SEQ ID NO: 37]
5'-GGTGTYTGGATHGGRAGRAC-3'

[SEQ ID NO: 38]
5'-ACTCCCRCTRTATCCTGACCA-3'

LNA Capture Probe Oligonucleotide:

[SEQ ID NO: 39]
5'-T+GAAAT+GATT+TG+GGATTTTTTTTTTT-3'

LNA Detection Probe Oligonucleotide:

[SEQ ID NO: 40]
5'-TTTTTTTTTTTTG+GAA+CG+GA+CAG-3'

4. NP Gene Target:
Degenerate Primer Pair:

[SEQ ID NO: 41]
5'-GGATCAAYGAYCGRAAYTTCTGGAGRG-3'

[SEQ ID NO: 42]
5'-YTYTGTGCWGCTGTTTGRAATTTYCCT-3'

LNA Capture Probe Oligonucleotide:

[SEQ ID NO: 43]
5'-A+GA+ATGTG+CAA+CATTTTTTTTTTTT-3'

LNA Detection Probe Oligonucleotide:

[SEQ ID NO: 44]
5'-TTTTTTTTTTTGG+CG+GA+AAA+CA-3'

5. NS Gene Target:
Degenerate Primer Pair:

[SEQ ID NO: 45]
5'-GATGTCAAAAATGCRRTTGGVRTCCT-3'

[SEQ ID NO: 46]
5'-YCTCATYACYGCYTCYCCAAGCGAATC-3'

LNA Capture Probe Oligonucleotide:

[SEQ ID NO: 47]
5'-G+GAG+GA+CT+TGAATTTTTTTTTTTT-3'

LNA Detection Probe Oligonucleotide:

[SEQ ID NO: 48]
5'-TTTTTTTTTTTA+CAGTTCG+AGTCTCT-3'

6. PB1 Gene Target:
Degenerate Primer Pair:

[SEQ ID NO: 49]
5'-ATGGAYACNGTCAACAGRACACAYCA-3'

[SEQ ID NO: 50]
5'-GGYARTGGYCCATCAATYGGGTTRAGT-3'

LNA Capture Probe Oligonucleotide:

[SEQ ID NO: 51]
5'-AA+AG+GGGAAG+TGTTTTTTTTTTTT-3'

LNA Detection Probe Oligonucleotide:

[SEQ ID NO: 52]
5'-TTTTTTTTTTTCAG+AAA+CTG+GGG-3'

7. PB2 Gene Target:
Degenerate Primer Pair:

[SEQ ID NO: 53]
5'-TAYGGRCCAGCAYTRAGYATCAATGAA-3'

[SEQ ID NO: 54]
5'-TCYCGTTTYCGTTTCATYACCARYAC-3'

LNA Capture Probe Oligonucleotide:

[SEQ ID NO: 55]
5'-AG+CT+AA+TG+TGCTTTTTTTTTTTTT-3

LNA Detection Probe Oligonucleotide:

[SEQ ID NO: 56]
5'-TTTTTTTTTTTTAG+TAAC+CTTG+CA-3'

All publications, patents, and patent applications cited in this specification are herein incorporated by reference as if each individual publication or patent application were specifically and individually indicated to be incorporated by reference, with exception that U.S. Provisional Application 60/839,537, filed Aug. 22, 2006, is not specifically incorporated by reference herein.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A stepwise method for detecting the presence of an influenza virus target nucleic acid in a clinical sample, comprising:

(a) isolating influenza virus particles which contain the target nucleic acid from the clinical sample using magnetic affinity capture;

(b) releasing the target nucleic acid from the influenza virus particles;

(c) amplifying influenza target nucleic acid using reverse transcriptase in combination with helicase dependent amplification, using amplification primers specific to the influenza target nucleic acid, to generate a solution containing a DNA amplification product corresponding to the influenza target nucleic acid sequence;

(d) hybridizing a detection oligonucleotide complementary to a first sequence of the influenza target nucleic acid to the DNA amplification product, which first sequence does not overlap with the amplification primer binding regions on the influenza target nucleic acid, which detection oligonucleotide was previously coupled to a visually detectable label, to generate a solution containing labeled DNA amplification product;

(e) applying an aliquot of the solution containing the labeled DNA amplification product to a sample receiving zone of a lateral flow chromatographic device, wherein the lateral flow chromatographic device comprises a lateral flow matrix which defines a flow path and which comprises in series:
  (i) a sample receiving zone for receiving an aliquot of a fluid sample; and,
  (ii) a capture zone in lateral flow contact with said receiving zone, said capture zone comprising a microporous membrane, at least a portion of which contains at least one capture oligonucleotide immobilized thereto, which capture oligonucleotide is complementary to a second and distinct sequence of the influenza target nucleic acid;
(f) the capture oligonucleotide hybridizing directly to the second and distinct sequence of the influenza target nucleic acid; and,
(g) detecting the presence of the influenza target nucleic acid by visually detecting the label at the site of the immobilized capture oligonucleotide;
wherein the isolating, releasing, and amplifying steps are performed in a single chamber; and
wherein the method achieves a sensitivity comparable to that of a typical homogeneous fluorescence assay while the detecting step is performable by the unaided human eye without the use of instrumentation.

2. The method according to claim 1, wherein the isolation of influenza virus particles comprises (a) incubating the clinical sample with magnetic beads functionalized with at least one affinity ligand capable of binding to the influenza virus particles, and (b) separating magnetic bead-bound cells and/or particles from other elements present in the clinical sample by applying a magnetic field to the sample.

3. The method according to claim 2, wherein the affinity ligand is an antibody.

4. The method according to claim 2, which further comprises a wash step following separation of magnetic bead-bound influenza virus particles from other elements present in the clinical sample.

5. The method according to claim 1, wherein releasing the target nucleic acid from the influenza virus particles is achieved by (i) alkaline lysis followed by neutralization or (ii) heating.

6. The method according to claim 1, in which the amplification primers of step (c) comprise a 5' poly dA or poly dT sequence of between 5 and 20 bases in length.

7. The method according to claim 1, wherein labeling the DNA amplification product is achieved concurrently with amplification of target nucleic acid.

8. The method according to claim 7, in which the amplification primers have the sequences of SEQ ID NOS: 19 and 20.

9. A stepwise method for detecting the presence of an influenza virus target nucleic acid in a clinical sample, comprising:
  (a) isolating influenza virus particles which contain the target nucleic acid from the clinical sample using magnetic affinity capture;
  (b) releasing the target nucleic acid from the influenza virus particles;
  (c) amplifying influenza target nucleic acid using reverse transcriptase in combination with helicase dependant amplification, using amplification primers specific to the influenza target nucleic acid, to generate a solution containing a DNA amplification product corresponding to the influenza target nucleic acid sequence;
  (d) applying an aliquot of the solution containing the DNA amplification product to a sample receiving zone of a lateral flow chromatographic device, wherein the lateral flow chromatographic device comprises a lateral flow matrix which defines a capillary flow path and which comprises in series:
    (i) a sample receiving zone for receiving an aliquot of a fluid sample;
    (ii) a labeling zone in lateral flow contact with said sample receiving zone, wherein the labeling zone comprises a porous material containing at least one detection oligonucleotide diffusively bound thereto, which detection oligonucleotide is complementary to a first sequence of the influenza target nucleic acid and was previously coupled to a visually detectable label; and,
    (iii) a capture zone in lateral flow contact with said labeling zone, said capture zone comprising a microporous membrane, at least a portion of which contains at least one capture oligonucleotide immobilized thereto, which capture oligonucleotide is complementary to a second and distinct sequence of the influenza target nucleic acid;
  (e) allowing the solution to traverse through the labeling and capture zones, under conditions sufficient to enable the hybridization of both the first sequence and the second distinct sequence of the DNA amplification product directly to the detection and capture oligonucleotides respectively; and,
  (f) detecting the presence of the target nucleic acid by visually detecting the label at the site of the immobilized capture oligonucleotide;
wherein the isolating, releasing, and amplifying steps are performed in a single chamber; and
wherein the method achieves a sensitivity comparable to that of a typical homogeneous fluorescence assay while the detecting step is performable by the unaided human eye without the use of instrumentation.

10. The method according to claim 9, wherein releasing the target nucleic acid from the influenza virus particles is achieved by (i) alkaline lysis followed by neutralization or (ii) heating.

11. The method according to claim 9, in which the amplification primers of step (c) comprise a poly dA or poly dT sequence of between 5 and 20 bases in length.

12. The method according to claim 11, in which the amplification primers have the sequences of SEQ ID NOS: 19 and 20.

* * * * *

UNITED STATES PATENT AND TRADEMARK OFFICE
CERTIFICATE OF CORRECTION

| | | |
|---|---|---|
| PATENT NO. | : 8,980,561 B1 | Page 1 of 1 |
| APPLICATION NO. | : 11/894908 | |
| DATED | : March 17, 2015 | |
| INVENTOR(S) | : Cai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this
Seventh Day of June, 2016

Michelle K. Lee
*Director of the United States Patent and Trademark Office*